(12) United States Patent
Apte et al.

(10) Patent No.: US 10,325,685 B2
(45) Date of Patent: *Jun. 18, 2019

(54) METHOD AND SYSTEM FOR CHARACTERIZING DIET-RELATED CONDITIONS

(71) Applicant: uBiome, Inc., San Francisco, CA (US)

(72) Inventors: Zachary Apte, San Francisco, CA (US); Jessica Richman, San Francisco, CA (US); Daniel Almonacid, San Francisco, CA (US); Catalina Valdivia, San Francisco, CA (US); Rodrigo Ortiz, San Francisco, CA (US); Inti Pedroso, San Francisco, CA (US); Victoria Dumas, San Francisco, CA (US); Paz Tapia, San Francisco, CA (US); Eduardo Morales, San Francisco, CA (US)

(73) Assignee: uBiome, Inc., San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/844,139

(22) Filed: Dec. 15, 2017

(65) Prior Publication Data

US 2018/0122510 A1    May 3, 2018

Related U.S. Application Data

(63) Continuation-in-part of application No. 15/606,743, filed on May 26, 2017, which is a continuation of application No. 14/919,614, filed on Oct. 21, 2015, now Pat. No. 9,703,929, and a continuation-in-part of application No. PCT/US2016/051174, filed on Sep. 9, 2016.

(60) Provisional application No. 62/066,369, filed on Oct. 21, 2014, provisional application No. 62/087,551, filed on Dec. 4, 2014, provisional application No. 62/092,999, filed on Dec. 17, 2014, provisional application No. 62/147,376, filed on Apr. 14, 2015, provisional application No. 62/147,212, filed on Apr. 14, 2015, provisional application No. 62/147,362, filed on Apr. 14, 2015, provisional application No. 62/146,855, filed on Apr. 13, 2015, provisional application No. 62/206,654, filed on Aug. 18, 2015, provisional application No. 62/215,900, filed on Sep. 9, 2015, provisional application No. 62/215,912, filed on Sep. 9, 2015, provisional application No. 62/216,086, filed on Sep. 9, 2015, provisional application No. 62/216,049, filed on Sep. 9, 2015, provisional application No. 62/215,892, filed on Sep. 9, 2015, provisional application No. 62/216,023, filed on Sep. 9, 2015, provisional application No. 62/434,948, filed on Dec. 15, 2016, provisional application No. 62/434,952, filed on Dec. 15, 2016, provisional application No. 62/434,959, filed on Dec. 15, 2016, provisional application No. 62/434,978, filed on Dec. 15, 2016, provisional application No. 62/434,995, filed on Dec. 15, 2016, provisional application No. 62/434,999, filed on Dec. 15, 2016, provisional application No. 62/435,006, filed on Dec. 15, 2016, provisional application No. 62/435,013, filed on Dec. 15, 2016, provisional application No.

(Continued)

(51) Int. Cl.

| | |
|---|---|
| *G01N 33/48* | (2006.01) |
| *G16H 50/20* | (2018.01) |
| *G16H 10/40* | (2018.01) |
| *G16B 50/00* | (2019.01) |
| *G16H 50/70* | (2018.01) |
| *G16H 20/60* | (2018.01) |
| *G06G 7/58* | (2006.01) |

(52) U.S. Cl.
CPC ............. *G16H 50/20* (2018.01); *G16B 50/00* (2019.02); *G16H 10/40* (2018.01); *G16H 20/60* (2018.01); *G16H 50/70* (2018.01); *Y02A 90/26* (2018.01)

(58) Field of Classification Search
None
See application file for complete search history.

(56) References Cited

U.S. PATENT DOCUMENTS

| 6,033,864 A | 3/2000 | Braun et al. |
| 6,309,643 B1 | 10/2001 | Braun et al. |

(Continued)

FOREIGN PATENT DOCUMENTS

| CN | 105407728 | 3/2015 |
| EP | 2631240 | 8/2013 |

(Continued)

OTHER PUBLICATIONS

"K03100: lepB: signal peptidase I," KEGG, Aug. 7, 2012 (Aug. 7, 2012), p. 1 of 1. Retrieved from the Internet: on Jun. 12, 2016 (Jun. 12, 2016).

(Continued)

*Primary Examiner* — Eric S Dejong
(74) *Attorney, Agent, or Firm* — Kilpatrick Townsend & Stockton LLP

(57) ABSTRACT

Embodiments of a method and/or system for characterizing a diet-related condition for a user can include one or more of: generating a microbiome dataset for each of an aggregate set of biological samples associated with a population of subjects, based on sample processing of the biological samples; processing a supplementary dataset associated with one or more diet-related conditions for the set of users; and performing a diet-related characterization process for the one or more diet-related conditions, based on the supplementary dataset and/or microbiome features extracted from the microbiome dataset.

27 Claims, 11 Drawing Sheets

Related U.S. Application Data

62/522,293, filed on Jun. 20, 2017, provisional application No. 62/555,782, filed on Sep. 8, 2017, provisional application No. 62/558,489, filed on Sep. 14, 2017, provisional application No. 62/582,172, filed on Nov. 6, 2017, provisional application No. 62/582,191, filed on Nov. 6, 2017, provisional application No. 62/582,162, filed on Nov. 6, 2017.

(56) References Cited

U.S. PATENT DOCUMENTS

| | | |
|---|---|---|
| 6,632,641 B1 | 10/2003 | Brennan et al. |
| 6,861,053 B1 | 3/2005 | Lin et al. |
| D521,645 S | 5/2006 | Lyons et al. |
| 7,048,906 B2 | 5/2006 | Lin et al. |
| 7,176,002 B2 | 2/2007 | Lao et al. |
| 8,460,648 B2 | 6/2013 | Borody |
| 8,478,544 B2 | 7/2013 | Colwell et al. |
| 8,598,203 B2 | 12/2013 | Tarcic et al. |
| 8,778,131 B2 | 7/2014 | Demmig et al. |
| 8,883,264 B2 | 11/2014 | Yang et al. |
| 9,028,841 B2 | 5/2015 | Henn et al. |
| 9,149,473 B2 | 10/2015 | Ecker et al. |
| 9,433,651 B2 | 9/2016 | Jones et al. |
| 9,447,195 B2 | 9/2016 | Cordova et al. |
| 9,506,109 B2 | 11/2016 | Savelkoul et al. |
| 9,663,831 B2 | 5/2017 | Apte et al. |
| 9,710,606 B2 | 7/2017 | Apte et al. |
| 10,242,160 B2 | 3/2019 | Apte et al. |
| 2002/0012926 A1 | 1/2002 | Quake et al. |
| 2003/0190314 A1 | 10/2003 | Campbell et al. |
| 2004/0028689 A1 | 2/2004 | Borody |
| 2005/0196785 A1 | 9/2005 | Quake et al. |
| 2006/0073501 A1 | 4/2006 | Van Den Boom et al. |
| 2006/0089310 A1 | 4/2006 | Goldstein et al. |
| 2006/0177424 A1 | 8/2006 | Cobb et al. |
| 2007/0134652 A1 | 6/2007 | Slepnev et al. |
| 2007/0259337 A1 | 11/2007 | Hully et al. |
| 2008/0131556 A1 | 6/2008 | De Simone et al. |
| 2010/0035232 A1 | 2/2010 | Ecker et al. |
| 2010/0129816 A1 | 5/2010 | Savelkoul et al. |
| 2010/0172874 A1 | 7/2010 | Turnbaugh et al. |
| 2011/0027219 A1 | 2/2011 | Tarcic et al. |
| 2011/0177976 A1 | 7/2011 | Gordon et al. |
| 2012/0045771 A1 | 2/2012 | Beier et al. |
| 2012/0129794 A1 | 5/2012 | Dowd et al. |
| 2012/0149584 A1 | 6/2012 | Olle et al. |
| 2012/0252775 A1 | 10/2012 | Finegold et al. |
| 2013/0017999 A1 | 1/2013 | Fremont et al. |
| 2013/0045874 A1 | 2/2013 | Ehrlich |
| 2013/0108598 A1 | 5/2013 | Oresic et al. |
| 2013/0121968 A1 | 5/2013 | Quay |
| 2013/0184302 A1 | 7/2013 | Bortey et al. |
| 2014/0093478 A1 | 4/2014 | Turnbaugh et al. |
| 2014/0136120 A1 | 5/2014 | Colwell et al. |
| 2014/0179726 A1 | 6/2014 | Bajaj et al. |
| 2014/0199281 A1 | 7/2014 | Henn et al. |
| 2014/0315929 A1 | 10/2014 | Chiosis |
| 2014/0341853 A1 | 11/2014 | Hovanky |
| 2014/0363399 A1 | 12/2014 | Jones et al. |
| 2015/0050245 A1 | 2/2015 | Herman et al. |
| 2015/0118330 A1 | 4/2015 | Heiman et al. |
| 2015/0133391 A1 | 5/2015 | De Vlaminick et al. |
| 2015/0211055 A1 | 7/2015 | Apte et al. |
| 2015/0211078 A1 | 7/2015 | Apte et al. |
| 2015/0213193 A1 | 7/2015 | Apte et al. |
| 2015/0374761 A1 | 12/2015 | Sadowsky et al. |
| 2016/0032363 A1 | 2/2016 | Stintzi et al. |
| 2016/0040216 A1 | 2/2016 | Akins et al. |
| 2016/0110515 A1 | 4/2016 | Apte et al. |
| 2016/0138089 A1 | 5/2016 | Harris et al. |
| 2016/0224749 A1 | 8/2016 | Apte et al. |
| 2016/0228003 A1 | 8/2016 | Apte et al. |
| 2017/0039347 A1 | 2/2017 | Apte et al. |
| 2017/0053061 A1 | 2/2017 | Almonacid et al. |
| 2017/0262608 A1 | 9/2017 | Apte et al. |
| 2017/0268045 A1 | 9/2017 | Apte et al. |
| 2017/0268046 A1 | 9/2017 | Apte et al. |
| 2017/0270268 A1 | 9/2017 | Apte et al. |
| 2017/0270269 A1 | 9/2017 | Apte et al. |
| 2017/0270270 A1 | 9/2017 | Apte et al. |
| 2017/0270271 A1 | 9/2017 | Apte et al. |
| 2017/0270272 A1 | 9/2017 | Apte et al. |
| 2017/0286619 A1 | 10/2017 | Apte et al. |
| 2017/0286620 A1 | 10/2017 | Apte et al. |
| 2017/0327864 A1 | 11/2017 | Apte et al. |
| 2017/0344719 A1 | 11/2017 | Apte et al. |
| 2018/0070827 A1 | 3/2018 | Apte et al. |
| 2019/0085396 A1 | 3/2019 | Apte et al. |

FOREIGN PATENT DOCUMENTS

| | | |
|---|---|---|
| EP | 2994756 | 3/2016 |
| WO | 050513 | 4/2012 |
| WO | 142605 | 10/2012 |
| WO | 121298 | 8/2014 |
| WO | 138999 | 9/2014 |
| WO | 144092 | 9/2014 |
| WO | 145958 | 9/2014 |
| WO | 013214 | 1/2015 |
| WO | 085326 | 6/2015 |
| WO | 095241 | 6/2015 |
| WO | 103165 | 7/2015 |
| WO | 112352 | 7/2015 |
| WO | 170979 | 11/2015 |
| WO | 2015/095241 A1 | 12/2015 |
| WO | 2016/065075 A1 | 4/2016 |
| WO | 138337 | 9/2016 |
| WO | 172643 | 10/2016 |
| WO | 044902 | 3/2017 |

OTHER PUBLICATIONS

"KEGG: Aminoacyl-tRNA biosynthesis—Reference pathway," Jul. 20, 2013 (Jul. 20, 2013). Retrieved from the internet: <http://web:archive.org/web/20130720015616/http:www.genome.jp/kegg-bin/show_pathway?map=map00970&show_description=show. on Jun. 20, 2016 (Jun. 20, 2016).

Avila, Maria et al., The Oral Microbiota: Living with a Permanent Guest, DNA and Cell Biology, Nov. 8, 2009, vol. 28, No. 8.

Carroll et al. "Alterations in composition and diversity of the intestinal microbiota in patients with diarrhea-predominant irritable bowel syndrome," Feb. 20, 2012 (Feb. 29, 2012), vol. 24, pp. 1-19 [Original pp. 5215-5230] entire document.

Cho et al. "The Human Microbiome: at the Interface of Health and Disease," Nature Reviews Genetics, Apr. 1, 2012 (Apr. 1, 2012), vol. 13, pp. 260-270.

Dewhirst, Floyd et al., The Human Oral Microbiome, Journal of Bacteriology, Oct. 2010, vol. 192, No. 19, pp. 5002-5017.

Evans, Morgan, Prosthetic valve endocarditis due to *Neisseria elongata* subsp. *elongata* in a patient with Klinefelter's syndrome, Journal of Medical Microbiology, Jun. 1, 2007, vol. 56, No. 6, pp. 860-862.

Greenblum et al. "Metagenomic Systems Biology of the Human Gut Microbiome Reveals Topological Shifts Associated with Obesity and Inflammatory Bowel Disease," Proceeding of the National Academy of Sciences, Dec. 19, 2011 (Dec. 19, 2011), vol. 109, pp. 594.

Kanehisa et al. "KEGG: Kyoto encyclopedia of genes and genomes," Nucleic Acids Research, Jan. 1, 2000 (Jan. 1, 2000), vol. 28, No. 1, pp. 27-30.

Mak et al. "MetaboLyzer: A Novel Statistical Workflow for Analyzing Post Processed LC/MS Metabolomics Data," Anal Chem, Jan. 7, 2014 (Jan. 7, 2014), vol. 86, pp. 506-513.

Morgan et al. "Dysfunction of the intestinal microbiome in inflammatory bowel disease and treatment," Genome Biol. Apr. 16, 2012 (Apr. 16, 2012), vol. 13(9):R79, pp. 1-18. entire document.

Mutlu et al. "A Compositional Look at the Human Gastrointestinal Microbiome and Immune Activation Parameters in HIV Infected Subjects," PLoS Pathogens, Feb. 20, 2014 (Feb. 20, 2014), vol. 10, pp. 1-18.

(56) References Cited

OTHER PUBLICATIONS

Nakayama et al. "Aberrant Structures of Fecal Bacterial Community in Allergic Infants Profiled by 16S rRNA Gene Pyrosequencing," FEMS Immunology & Medical Microbiology, Dec. 1, 2011 (Dec. 1, 2011), vol. 63, pp. 397-406.
Ponnusamy et al. "Microbial community and metabolomic comparison of irritable bowel syndrome faeces," Feb. 17, 2011 (Feb. 17, 2011), vol. 60, pp. 817-827. entire document.
Ferreira; et al. "Distribution, Detection of Enterotoxigenic Strains and Antimicrobial Drug Susceptibility Patterns of Bacteroides Fragilis Group Diarrheic and Non-Diarrheic Feces fro Brazilian Infants," Brazillian Journal of Microbiology, Sep. 30, 2010 (Sep. 30, 2010), vol. 48, No. 11, pp. 603-611, entire document.
Verma; et al. "Real-Time Analysis of Mucosal Flora in Patients with Inflammatory Bowel Disease in India," Journal of Clinical Microbiology, Nov. 30, 2010 (Nov. 30, 2010), vol. 48, No. 11, pp. 4279-4282. Entire document.
Pozuelo; et al. "Reduction of butyrate-and methane-producing microorganisms in patients with Irritable Bowel Syndrome," Scientific Reports, Aug. 4, 2015 (Aug. 4, 2015), vol. 5, No. 12693, pp. 1-12. Entire document.
Rajilic-Stojanovic; et al. "The first 1000 cultured species of the human gastrointestinal microbiota," FEMS Microbiology Reviews, Jun. 27, 2014 (Jun. 27, 2014), vol. 38, No. 5, pp. 996-1047. Entire document.
Scarpellini; et al. "The human gut microbiota and virome: Potential therapeutic implications," Digestive and Liver Disease, Jul. 18, 2015 (Jul. 18, 2015), vol. 47, No. 12, pp. 1007-1012. Entire document.
Bornigen, et al., "Functional Profiling of the Gut Microbiome in Disease-associated Inflammation", Genome Medicine, vol. 5, No. 65, 2013, pp. 1-13.
Canadian Application No. 2,962,466, Examination Report dated Mar. 23, 2018, 4 pages.
Duncan, et al., "Human Colonic Microbiota Associated with Diet, Obesity and Weight Loss", International Journal of Obesity, vol. 32, Sep. 9, 2008, pp. 1720-1724.
European Application No. 15852829.9, Extended European Search Report dated May 14, 2018, 8 pages.
Huttenhower, et al., "Structure, Function and Diversity of the Healthy Human Microbiome", Nature, vol. 486, Jun. 14, 2012, pp. 207-214.
International Application No. PCT/US2015/056767, International Preliminary Report on Patentability dated May 4, 2017, 9 pages.
International Application No. PCT/US2015/056767, International Search Report and Written Opinion dated Jan. 11, 2016, 10 pages.
International Application No. PCT/US2016/051174, International Preliminary Report on Patentability dated Mar. 22, 2018, 19 pages.
International Application No. PCT/US2016/051174, International Search Report and Written Opinion dated Feb. 6, 2017, 22 pages.
International Application No. PCT/US2017/066836, International Search Report and Written Opinion dated Mar. 19, 2018, 13 pages.
Kinross, et al., "Gut Microbiome-host Interactions in Health and Disease", Genome Medicine, vol. 3, No. 14, 2011, pp. 1-12.
Larsen, et al., "Gut Microbiota in Human Adults with Type 2 Diabetes Differs from Non-Diabetic Adults", PLOS One, vol. 5, No. 2, e9085, Feb. 5, 2010, pp. 1-10.

Morgan, et al., "Biodiversity and Functional Genomics in the Human Microbiome", Trends Genet., vol. 29, No. 1, Jan. 2013, pp. 51-58.
Schloss, et al., "Introducing DOTUR, a Computer Program for Defining Operational Taxonomic Units and Estimating Species Richness", Applied and Environmental Microbiology, vol. 71, No. 3, Mar. 2005, pp. 1501-1506.
U.S. Appl. No. 14/919,614, Non-Final Office Action dated Jul. 14, 2016, 10 pages.
U.S. Appl. No. 14/919,614, Notice of Allowance dated May 19, 2017, 10 pages.
U.S. Appl. No. 15/606,743, Non-Final Office Action dated Dec. 19, 2017, 10 pages.
U.S. Appl. No. 15/606,743, Notice of Allowance dated Sep. 20, 2018, 5 pages.
U.S. Appl. No. 15/606,824, Final Office Action dated Sep. 20, 2018, 8 pages.
U.S. Appl. No. 15/606,824, Non-Final Office Action dated Jan. 16, 2018, 10 pages.
U.S. Appl. No. 15/606,874, Final Office Action dated Aug. 31, 2018, 8 pages.
U.S. Appl. No. 15/606,874, Non-Final Office Action dated Feb. 9, 2018, 10 pages.
U.S. Appl. No. 15/606,874, Notice of Allowance dated Jan. 17, 2019, 5 pages.
U.S. Appl. No. 15/606,909, Final Office Action dated Sep. 20, 2018, 8 pages.
U.S. Appl. No. 15/606,909, Non-Final Office Action dated Mar. 9, 2018, 10 pages.
U.S. Appl. No. 15/606,909, Notice of Allowance dated Feb. 20, 2019, 5 pages.
U.S. Appl. No. 15/606,943, Final Office Action dated Nov. 1, 2018, 7 pages.
U.S. Appl. No. 15/606,943, Non-Final Office Action dated Apr. 10, 2018, 10 pages.
U.S. Appl. No. 15/606,943, Notice of Allowance dated Mar. 8, 2019, 5 pages.
U.S. Appl. No. 15/606,975, Final Office Action dated Jun. 14, 2018, 8 pages.
U.S. Appl. No. 15/606,975, Non-Final Office Action dated Sep. 25, 2017, 10 pages.
U.S. Appl. No. 15/606,975, Notice of Allowance dated Oct. 19, 2018, 5 pages.
U.S. Appl. No. 15/621,144, Final Office Action dated Nov. 1, 2018, 7 pages.
U.S. Appl. No. 15/621,144, Non-Final Office Action dated Apr. 10, 2018, 10 pages.
U.S. Appl. No. 15/621,144, Notice of Allowance dated Mar. 8, 2019, 6 pages.
U.S. Appl. No. 15/621,152, Final Office Action dated Nov. 1, 2018, 7 pages.
U.S. Appl. No. 15/621,152, Non-Final Office Action dated Apr. 10, 2018, 10 pages.
U.S. Appl. No. 15/621,152, Notice of Allowance dated Mar. 8, 2019, 6 pages.
Uy, et al., "Effects of Gluten-Free, Dairy-Free Diet on Childhood Nephrotic Syndrome and Gut Microbiota", Pediatric Research, vol. 77, No. 1, Jan. 2015, pp. 252-255.
U.S. Appl. No. 15/606,824, "Notice of Allowance," dated Mar. 26, 2019, 6 pages.
U.S. Appl. No. 15/606,975, "Notice of Allowance," dated Apr. 3, 2019, 5 pages.

_US 10,325,685 B2_

METHOD AND SYSTEM FOR CHARACTERIZING DIET-RELATED CONDITIONS

CROSS-REFERENCE TO RELATED APPLICATIONS

This application is a continuation-in-part of U.S. application Ser. No. 15/606,743, filed 26 May 2017, which is a continuation of U.S. application Ser. No. 14/919,614, filed 21 Oct. 2015, which claims the benefit of U.S. Provisional Application Ser. No. 62/066,369, filed 21 Oct. 2014, U.S. Provisional Application Ser. No. 62/087,551, filed 4 Dec. 2014, U.S. Provisional Application Ser. No. 62/092,999, filed 17 Dec. 2014, U.S. Provisional Application Ser. No. 62/147,376, filed 14 Apr. 2015, U.S. Provisional Application Ser. No. 62/147,212, filed 14 Apr. 2015, U.S. Provisional Application Ser. No. 62/147,362, filed 14 Apr. 2015, U.S. Provisional Application Ser. No. 62/146,855, filed 13 Apr. 2015, and U.S. Provisional Application Ser. No. 62/206,654, filed 18 Aug. 2015, which are each incorporated in its entirety herein by this reference.

This application is also a continuation-in-part of PCT Application serial number PCT/US16/51174, filed 9 Sep. 2016, which claims the benefit of U.S. Provisional Application Ser. No. 62/215,900, filed 9 Sep. 2015, U.S. Provisional Application Ser. No. 62/215,912, filed 9 Sep. 2015, U.S. Provisional Application Ser. No. 62/216,086, filed 9 Sep. 2015, U.S. Provisional Application Ser. No. 62/216,049, filed 9 Sep. 2015, U.S. Provisional Application Ser. No. 62/215,892, filed 9 Sep. 2015, U.S. Provisional Application Ser. No. 62/216,023, filed 9 Sep. 2015, which are each incorporated in its entirety herein by this reference.

This application also claims the benefit of U.S. Provisional Application Ser. No. 62/434,948, filed 15 Dec. 2016, U.S. Provisional Application Ser. No. 62/434,952, filed 15 Dec. 2016, U.S. Provisional Application Ser. No. 62/434,959 filed 15 Dec. 2016, U.S. Provisional Application Ser. No. 62/434,978, filed 15 Dec. 2016, U.S. Provisional Application Ser. No. 62/434,995, filed 15 Dec. 2016, U.S. Provisional Application Ser. No. 62/434,999, filed 15 Dec. 2016, U.S. Provisional Application Ser. No. 62/435,006, filed 15 Dec. 2016, and U.S. Provisional Application Ser. No. 62/435,013, filed 15 Dec. 2016, which are each herein incorporated in their entireties by this reference.

This application also claims the benefit of U.S. Provisional Application Ser. No. 62/522,293, filed 20 Jun. 2017, U.S. Provisional Application Ser. No. 62/555,782, filed 8 Sep. 2017, U.S. Provisional Application Ser. No. 62/558,489 filed 14 Sep. 2017, U.S. Provisional Application Ser. No. 62/582,172, filed 6 Nov. 2017, U.S. Provisional Application Ser. No. 62/582,191, filed 6 Nov. 2017, and U.S. Provisional Application Ser. No. 62/582,162, filed 6 Nov. 2017, which are each herein incorporated in their entireties by this reference.

TECHNICAL FIELD

This invention relates generally to the field of microbiology and more specifically to a new and useful method and system for characterizing and/or treating diet-related conditions associated with microorganisms.

BACKGROUND

A microbiome is an ecological community of commensal, symbiotic, and pathogenic microorganisms that are associated with an organism. The human microbiome includes over 10 times more microbial cells than human cells, but characterization of the human microbiome is still in nascent stages due to limitations in sample processing techniques, genetic analysis techniques, and resources for processing large amounts of data. Nonetheless, the microbiome is suspected to play at least a partial role in a number of health/disease-related states (e.g., preparation for childbirth, diabetes, auto-immune disorders, gastrointestinal disorders, rheumatoid disorders, neurological disorders, etc.). Given the profound implications of the microbiome in affecting a subject's health, efforts related to the characterization of the microbiome, the generation of insights from the characterization, and the generation of therapeutics configured to rectify states of dysbiosis should be pursued. Current methods and systems for analyzing the microbiomes of humans and providing therapeutic measures based on gained insights have, however, left many questions unanswered. In particular, methods for characterizing certain health conditions and therapies (e.g., probiotic therapies) tailored to specific subjects based upon microbiome composition and/or functional features have not been viable due to limitations in current technologies.

As such, there is a need in the field of microbiology for a new and useful method and system for characterizing health conditions in an individualized and population-wide manner.

DESCRIPTION OF THE EMBODIMENTS

The following description of the embodiments of the invention is not intended to limit the invention to these embodiments, but rather to enable any person skilled in the art to make and use this invention.

1. Overview

Figure 1A:
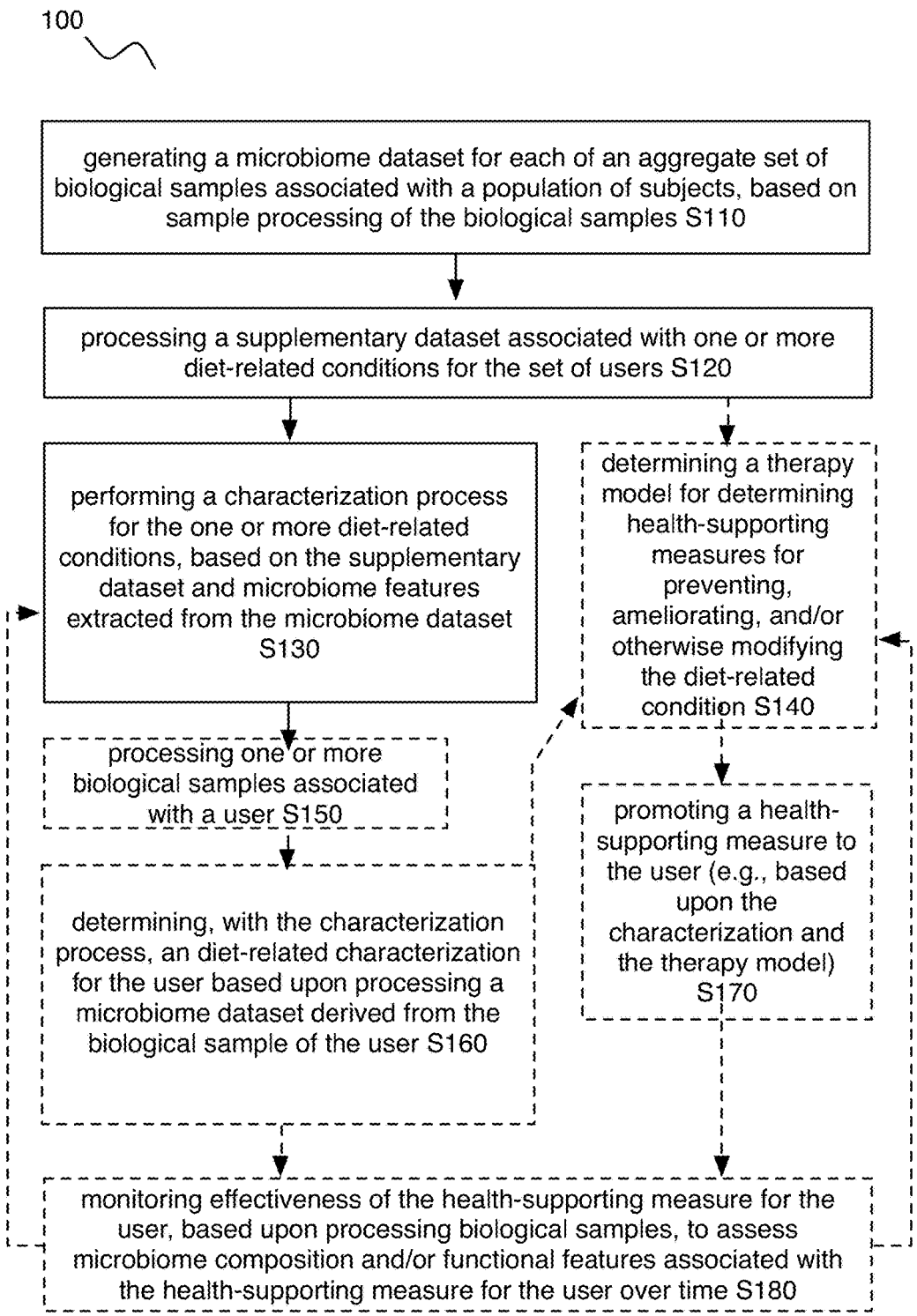
FIGS. 1A-1B are flowchart representations of variations of an embodiment of a method.
Figure 1B:
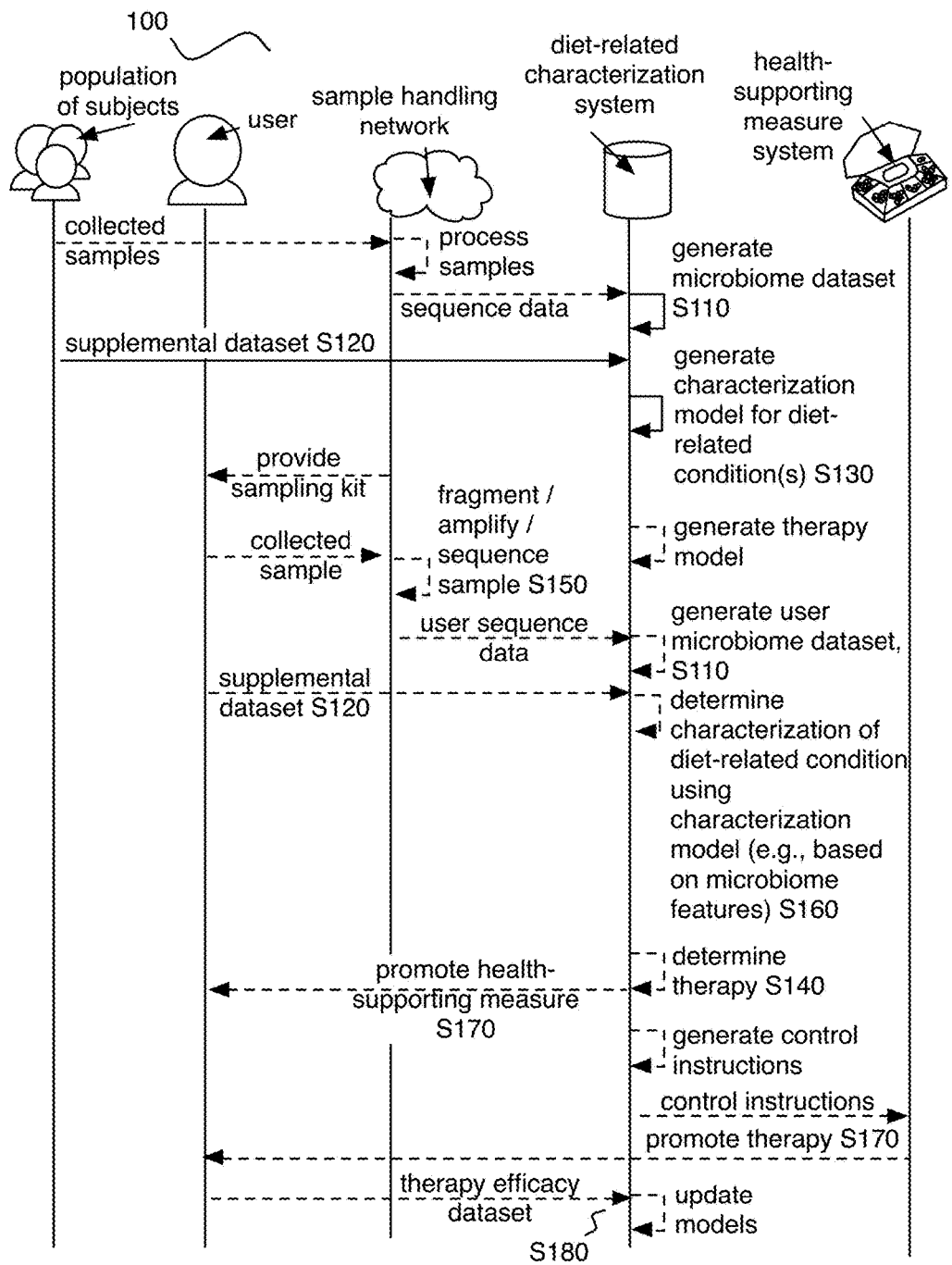

As shown in FIG. 1, an embodiment of a method 100 for characterizing a diet-related condition for a user can include one or more of: generating a microbiome dataset (e.g., microorganism sequence dataset, microbiome composition diversity dataset, microbiome functional diversity dataset, etc.) for each of an aggregate set of biological samples associated with a population of subjects, based on sample processing of the biological samples S110; processing a supplementary dataset associated with (e.g., informative of; describing; indicative of; etc.) one or more diet-related conditions for the set of users S120; and performing a characterization process for the one or more diet-related conditions, based on the supplementary dataset and microbiome features (e.g., microbiome composition diversity features; microbiome functional diversity features; etc.) extracted from the microbiome dataset S130. Embodiments of the method 100 can additionally or alternatively include one or more of: determining a therapy model for determining therapies for supporting, improving, ameliorating, and/or otherwise modifying one or more diet-related conditions S140; processing one or more biological samples from a user (e.g., subject) S150; determining, with the characterization process, a diet-related characterization for the user based upon processing a microbiome dataset (e.g., user microorganism sequence dataset, microbiome composition dataset, microbiome functional diversity dataset, etc.) derived from the biological sample of the user S160; promoting a health-supporting measure for the diet-related condition to the user (e.g., based upon the diet-related characterization and/or a therapy model) S170; monitoring effectiveness of the health-supporting measure for the user, based upon processing biological samples, to assess microbiome composition and/or functional features associated with the health-supporting measure for the user over time S180; and/or any other suitable operations.

Embodiments of the method 100 and/or system 200 can preferably generate and promote characterizations and/or health-supporting measures for diet-related conditions, which can be associated with any one or more of: diet-related behaviors, dietary restrictions, health-condition associated diets, self-elected diets, eating disorders, and/or any other suitable aspect related to dietary or appetite affecting conditions. In variations, diet-related conditions can include any one or more of: vegetarian diets, vegan diets, omnivorous diets, raw meat diets, low carb diets, dairy free diets/diets for those with dairy allergies, gluten free diets, pescataria diets, raw food diets, diets for those who are at various stages of diabetes/pre-diabetes, lactose and fermented food tolerant diets, diets associated with eating-related disorders (e.g., obesity, etc.), fad diets (e.g., high protein diets, liquid diets, detox diets, South Beach diet, Mediterranea diets, Atkins diet, Paleo diet, Volumetric diets, etc.), ketogenic diets, and any other suitable diet-related condition. The method 100 can additionally or alternatively compare and contrast microbiome-derived or associated features across different subjects (e.g., human subjects, non-human subjects, etc.), in relation to different categories of diets, as described in more detail below. The method 100 can additionally or alternatively generate associations between diets and health conditions (i.e.: diabetes type) in a health-supporting and/or improving manner.

additionally or alternatively, the method 100 and/or system 200 can include a combination analysis that includes a Concordance Score (CS) for comparing 2 (or more) different set of treatments and/or condition, wherein a first treatment is compared with a second treatment (i.e., trait 1: diabetes type 2 v/s control; trait 2, not_dairy v/s Omnivore diet) and by using statistical and/or bioinformatics analysis can be obtained a single score (i.e., value between 0 and 1). Such as score can be calculated by measures of agreement of the microbiome statistical association with each trait. In a particular but not limited example of a CS calculation method, CS corresponds to the ratio of agreement and disagreement (#agreements/(#agreements+#disagreements)) which can be further improved, but not limited to, by placing this estimator within a Bayesian framework with a Beta distribution prior with specific parameters, for instance leading to a so called flat prior, leading ((#agreements+1)/(#agreements+#disagreements+2)), known to have better asymptotic statistical properties. In an example of this method, the CS can be calculated by counting the agreements as the number of taxa associated with both conditions that show the same direction of effect (i.e., increased on controls or cases) and number disagreements as the number of taxa associated with both conditions that show the different direction of effect (i.e., trait 1: increased in controls and trait 2: increased in cases).

This Concordance Score (CS) reflects the extent to which the microbiome patterns associated with each trait correlate to each other, wherein the correlation between both traits can be direct or inverse. More specifically, depending on the CS can indicate the relationship between the condition groups of each traits and their impact direction of the microbiome profiles. Thus, a CS>0.5 indicates a direct, positive correlation or positive relationship between the condition groups of each trait. Similarly, a CS<0.5 indicates an inverse concordance between both conditions for Trait 1 and Trait 2. A "direct concordance" indicates that taxa associated show the same direction or that the effects follow the same pattern for both conditions in present analysis (Trait 1 and Trait 2); and on the contrary, an "inverse concordance" indicates that associated taxa relevant for both conditions follows opposite patterns. As an application for this methodology, can be provide a personalized diagnostic and/or treatment tool for a user or a set of users with a health condition or specific condition associated with diet, including mediating the modulation of microbiota (i.e: gut microbiota) by the change of diet of food habits to improve health conditions symptoms or treatment for a specific health condition. As an specific example, the application of the CS to a single individual can be exemplified by the case on which the focal individual wishes to reduce his/her risk or reduce the impact of symptoms, improve the recovery process, avoid relapse of his/her conditions, e.g, Type 2 Diabetes, and a dietary intervention can be suggested by considering the CS between Type 2 Diabetes and different dietary options. Important, due to comorbid conditions or other reasons the focal individual may not which to proceed with any dietary intervention. The CS method can provide alternative dietary interventions. This can be selected among those described in the following tables:

TABLE 1

The table provides Concordance Score between traits calculated using statistical analyses that considered individual taxa abundances on their statistical association pattern with each trait.

| Trait1 (condition vs control) | Trait2 (condition vss control) | Site | Concordance Score |
|---|---|---|---|
| Type 2 Diabetes vs Control | Halal vs Omnivore | mouth | 0.182 |
| Type 2 Diabetes vs Control | Low Carb vs Omnivore | gut | 0.464 |
| Type 2 Diabetes vs Control | Low Carb vs Omnivore | mouth | 0.286 |
| Type 2 Diabetes vs Control | Low Carb vs Vegetarian | mouth | 0.200 |
| Type 2 Diabetes vs Control | Low Carb vs Vegetarian | gut | 0.542 |
| Type 2 Diabetes vs Control | No Red Meat vs Omnivore | gut | 0.333 |
| Type 2 Diabetes vs Control | No Red Meat vs Omnivore | mouth | 0.500 |
| Type 2 Diabetes vs Control | Dairy Free vs Omnivore | gut | 0.483 |
| Type 2 Diabetes vs Control | Dairy Free vs Omnivore | genital | 0.114 |

TABLE 1-continued

The table provides Concordance Score between traits calculated using statistical analyses that considered individual taxa abundances on their statistical association pattern with each trait.

| Trait1 (condition vs control) | Trait2 (condition vss control) | Site | Concordance Score |
|---|---|---|---|
| Type 2 Diabetes vs Control | Dairy Free vs Omnivore | nose | 0.079 |
| Type 2 Diabetes vs Control | Dairy Free vs Omnivore | skin | 0.049 |
| Type 2 Diabetes vs Control | Dairy Free vs Vegetarian | genital | 0.237 |
| Type 2 Diabetes vs Control | Dairy Free vs Vegetarian | gut | 0.318 |
| Type 2 Diabetes vs Control | Dairy Free vs Vegetarian | mouth | 0.344 |
| Type 2 Diabetes vs Control | Dairy Free vs Vegetarian | nose | 0.240 |
| Type 2 Diabetes vs Control | Dairy Free vs Vegetarian | skin | 0.220 |
| Type 2 Diabetes vs Control | Dairy Free vs Vegetarian | mouth | 0.209 |
| Type 2 Diabetes vs Control | Paleo vs Omnivore | gut | 0.385 |
| Type 2 Diabetes vs Control | Paleo vs Omnivore | mouth | 0.094 |
| Type 2 Diabetes vs Control | Pescetarian vs Omnivore | gut | 0.341 |
| Type 2 Diabetes vs Control | Raw vs Omnivore | gut | 0.444 |
| Type 2 Diabetes vs Control | Raw vs Omnivore | skin | 0.333 |
| Type 2 Diabetes vs Control | Vegan vs Omnivore | gut | 0.339 |
| Type 2 Diabetes vs Control | Vegan vs Omnivore | mouth | 0.500 |
| Type 2 Diabetes vs Control | Vegan vs Omnivore | gut | 0.374 |

TABLE 2

The table provides Concordance Score between traits calculated using statistical analyses that considered individual taxa abundances and presence/absence combined information on their statistical association pattern with each trait.

| Trait1 (condition vs control) | Trait2 (condition vss control) | Site | Concordance Score |
|---|---|---|---|
| Type 2 Diabetes vs Control | Halal vs Omnivore | gut | 0.632 |
| Type 2 Diabetes vs Control | Kosher vs Omnivore | gut | 0.800 |
| Type 2 Diabetes vs Control | Low Carb vs Omnivore | genital | 0.250 |
| Type 2 Diabetes vs Control | Low Carb vs Omnivore | gut | 0.546 |
| Type 2 Diabetes vs Control | Low Carb vs Omnivore | mouth | 0.500 |
| Type 2 Diabetes vs Control | Low Carb vs Vegetarian | mouth | 0.667 |
| Type 2 Diabetes vs Control | Low Carb vs Vegetarian | genital | 0.667 |
| Type 2 Diabetes vs Control | Low Carb vs Vegetarian | gut | 0.527 |
| Type 2 Diabetes vs Control | No Red Meat vs Omnivore | gut | 0.333 |
| Type 2 Diabetes vs Control | No Red Meat vs Omnivore | mouth | 0.800 |
| Type 2 Diabetes vs Control | Dairy Free vs Omnivore | gut | 0.525 |
| Type 2 Diabetes vs Control | Dairy Free vs Omnivore | genital | 0.160 |
| Type 2 Diabetes vs Control | Dairy Free vs Omnivore | nose | 0.089 |
| Type 2 Diabetes vs Control | Dairy Free vs Omnivore | skin | 0.076 |
| Type 2 Diabetes vs Control | Dairy Free vs vegetarian | genital | 0.255 |
| Type 2 Diabetes vs Control | Dairy Free vs vegetarian | gut | 0.309 |
| Type 2 Diabetes vs Control | Dairy Free vs vegetarian | mouth | 0.372 |
| Type 2 Diabetes vs Control | Dairy Free vs vegetarian | nose | 0.274 |
| Type 2 Diabetes vs Control | Dairy Free vs vegetarian | skin | 0.253 |
| Type 2 Diabetes vs Control | Paleo vs Omnivore | gut | 0.429 |
| Type 2 Diabetes vs Control | Paleo vs Omnivore | mouth | 0.118 |
| Type 2 Diabetes vs Control | Pescetarian vs Omnivore | gut | 0.385 |
| Type 2 Diabetes vs Control | Raw vs Omnivore | gut | 0.456 |
| Type 2 Diabetes vs Control | Raw vs Omnivore | genital | 0.667 |
| Type 2 Diabetes vs Control | Vegan vs Omnivore | gut | 0.413 |
| Type 2 Diabetes vs Control | Vegan vs Omnivore | genital | 0.667 |
| Type 2 Diabetes vs Control | Vegan vs Omnivore | skin | 0.333 |
| Type 2 Diabetes vs Control | Vegan vs Omnivore | gut | 0.428 |

In this example, in the case on which the focal individual follow a omnivore diet the CS (based on the relative abundance as indicated on Table 1) indicates that to ameliorate Type 2 Diabetes the individuals should select one or a combination of the following dietary styles no red meat, vegan, pescetarian, vegenarian, paleo, raw, low carb, not dairy and should discourage one or a combination of the following dietary styles Halal and Kosher.

Embodiments of the method 100 and/or system 200 can be implemented for a single subject for whom microbiome characterization and/or microbiome modulation with therapeutics is of interest, and can additionally or alternatively be implemented for a population of subjects (e.g., including the subject, excluding the subject), where the population of subjects can include patients dissimilar to and/or similar to the subject (e.g., in health condition, in dietary needs, in demographic features, etc.). Thus, information derived from the population of subjects can be used to provide additional insight into connections between behaviors of a subject and effects on the subject's microbiome, due to aggregation of data from a population of subjects. In a variation, an aggregate set of biological samples is preferably received from a wide variety of subjects, collectively including subjects of one or more of: different demographics (e.g., genders, ages, marital statuses, ethnicities, nationalities, socioeconomic statuses, sexual orientations, etc.), different health conditions (e.g., health and disease states), different living situations (e.g., living alone, living with pets, living with a significant other, living with children, etc.), different dietary habits (e.g., omnivorous, vegetarian, vegan, sugar consumption, acid consumption, caffeine consumption, etc.), different behavioral tendencies (e.g., levels of physical activity, drug use, alcohol use, etc.), different levels of mobility (e.g., related to distance traveled within a given time period), and/or any other suitable trait that has an effect on microbiome composition and/or functional features. As such, as the number of subjects increases, the predictive power of processes implemented in portions of the method 100 increases, in relation to characterizing a variety of subjects based upon their microbiomes. However, the method 100 can involve generation of characterization and therapies derived from biological sample data from any other suitable group of subjects.

Data described herein (e.g., sequence data, microbiome composition features, microbiome functional features, diet-related characterizations, therapy determinations, etc.) can be associated with any suitable temporal indicators (e.g., seconds, minutes, hours, days, weeks, etc.) including one or more: temporal indicators indicating when the data was collected (e.g., temporal indicators indicating when a sample was collected; etc.), determined, transmitted, received, and/or otherwise processed; temporal indicators providing context to content described by the data (e.g., temporal indicators associated with diet-related characterizations, such as where the diet-related characterization describes the diet-related conditions and/or user microbiome status a particular time; etc.); changes in temporal indicators (e.g., changes in diet-related characterizations over time, such as in response to consumed health-supporting measures; latency between sample collection and sample analysis; etc.); and/or any other suitable indicators related to time.

Additionally or alternatively, parameters, metrics, inputs, outputs, and/or other suitable data can be associated with value types including: scores (e.g., microbiome diversity scores; risk scores for diet-related conditions; microbiome composition diversity scores; microbiome functional diversity scores; etc.), binary values (e.g., presence or absence of a microbiome feature; presence or absence of a diet-related condition; etc.), classifications (e.g., diet-related condition classifications; behavioral classifications; demographic classifications; etc.), confidence levels (e.g., associated with microorganism sequence datasets; with microbiome diversity scores; with other diet-related characterizations; etc.), values along a spectrum, and/or any other suitable types of values. Any suitable types of data described herein can be used as inputs (e.g., for different models described herein), generated as outputs (e.g., of different models), and/or manipulated in any suitable manner for any suitable components associated with the method 100 and/or system 200.

One or more instances and/or portions of the method 100 and/or processes described herein can be performed asynchronously (e.g., sequentially), concurrently (e.g., multiplex sample processing, such as multiplex amplification of microorganism nucleic acid fragments corresponding to target sequences associated with diet-related conditions; computationally determining microbiome datasets, microbiome features, and/or diet-related conditions in parallel for a plurality of users, such as concurrently on different threads for parallel computing to improve system processing ability; etc.), in temporal relation to a trigger event (e.g., performance of a portion of the method 100), and/or in any other suitable order at any suitable time and frequency by and/or using one or more instances of the system 200, components, and/or entities described herein. For example, the method 100 can include generating a microorganism sequence dataset based on processing microorganism nucleic acids of a biological sample with a bridge amplification substrate of a next generation sequencing platform of a sample handling system, and determining microbiome composition diversity features and microbiome functional diversity features at computing devices operable to communicate with the next generation sequencing platform.

Figure 2:
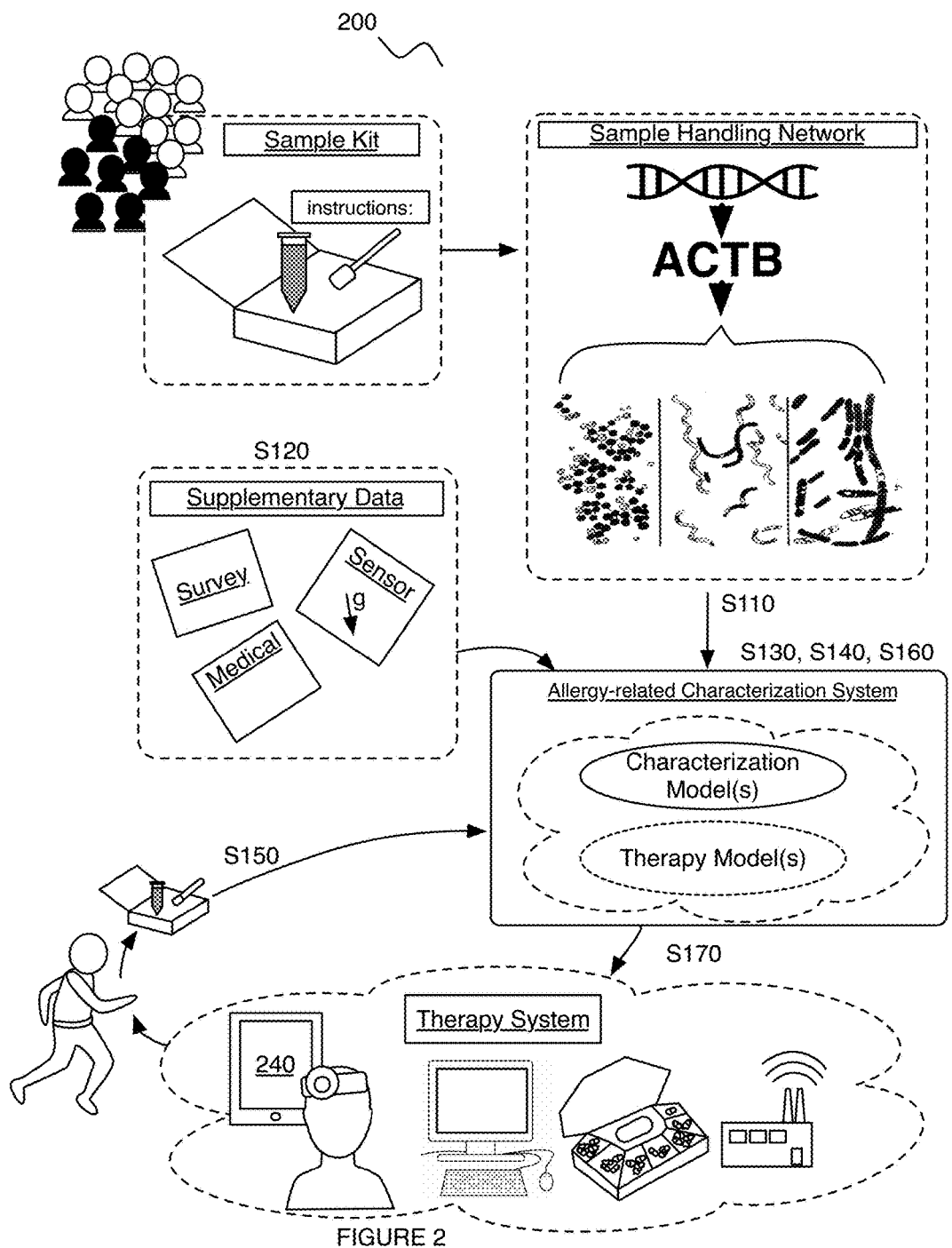
FIG. 2 depicts embodiments of a method and system.

As shown in FIG. 2, embodiments of the system 200 can include any one or more of: a handling system (e.g., a sample handling system, etc.) operable to collect biological samples (e.g., collected by users and included in containers including pre-processing reagents; etc.) from one or more users (e.g., a human subject, patient, animal subject, environmental ecosystem, care provider, etc.), the handling system including a sequencing platform (e.g., next-generation sequencing platform) operable to determine a microorganism sequence dataset for the one or more users from the biological samples; a diet-related characterization system operable to: determine user microbiome features (e.g., microbiome composition features; microbiome functional features; diversity features; relative abundance ranges; etc.) based on the microorganism sequence dataset, and determine diet-related characterizations based on the user microbiome features; and/or a treatment system operable to promote a therapy for one or more diet-related conditions based on the diet-related characterization. However, the method 100 and/or system 200 can be configured in any suitable manner.

2. Benefits.

Microbiome analysis can enable accurate and efficient characterization and/or therapy provision for diet-related conditions caused by and/or otherwise associated with microorganisms. The technology can overcome several challenges faced by conventional approaches in characterizing and/or promoting therapies for a condition. First, conventional approaches can require patients to visit one or more care providers to receive a characterization and/or a health-supporting recommendation for a diet-related condition, which can amount to inefficiencies and health-risks associated with the amount of time elapsed before diagnosis and/or treatment. Second, conventional genetic sequencing and analysis technologies for human genome sequencing can be incompatible and/or inefficient when applied to the microbiome (e.g., where the human microbiome can include over 10 times more microbial cells than human cells; where optimal sample processing techniques can differ, such as for reducing amplification bias; where different approaches to diet-related characterizations can be employed; where the types of conditions and correlations can differ; where sequence reference databases can differ; where the microbiome can vary across different body regions of the user; etc.). Third, the onset of sequencing technologies (e.g., next-generation sequencing) has given rise to technological issues (e.g., data processing and analysis issues for the plethora of generated sequence data; issues with processing a plurality of biological samples in a multiplex manner; information display issues; therapy prediction issues, therapy provision issues, etc.) that would not exist but for the unprecedented advances in speed and data generation associated with sequencing genetic material. Specific examples of the method 100 and/or system 200 can confer technologically-rooted solutions to at least the challenges described above.

First, the technology can confer improvements in computer-related technology (e.g., modeling associated with characterizing and/or promoting therapies for diet-related conditions; improving computational efficiency in storing, retrieving, and/or processing microorganism-related data for diet-related conditions; computational processing associated with biological sample processing; etc.) by facilitating computer performance of functions not previously performable. For example, the technology can computationally generate diet-related characterizations and/or recommended health-supporting measures associated with microbiome analysis based on techniques (e.g., leveraging microorganism taxonomic databases, etc.) that are recently viable due to advances in sample processing techniques and sequencing technology.

Second, the technology can confer improvements in processing speed, diet-related characterization accuracy, microbiome-related therapy determination and promotion, and/or other suitable aspects in relation to diet-related conditions. For example, the technology can generate and apply feature-selection rules (e.g., microbiome diversity feature-selection rules for composition, function, etc.) to select an optimized subset of features (e.g., microbiome composition diversity features such as reference relative abundance features indicative of healthy ranges of taxonomic groups associated with diet-related conditions; user relative abundance features that can be compared to reference relative abundance features correlated with diet-related conditions and/or therapy responses; etc.) out of a vast potential pool of features (e.g., extractable from the plethora of microbiome data such as sequence data) for generating and/or applying characterization models and/or therapy models. The potential size of microbiomes (e.g., human microbiomes, animal microbiomes, etc.) can translate into a plethora of data, giving rise to questions of how to process and analyze the vast array of data to generate actionable microbiome insights in relation to diet-related conditions. However, the feature-selection rules and/or other suitable computer-implementable rules can enable one or more of: shorter generation and execution times (e.g., for generating and/or applying models; for determining diet-related characterizations and/or associated therapies; etc.); optimized sample processing techniques (e.g., improving transformation of microorganism nucleic acids from biological samples through using primer types, other biomolecules, and/or other sample processing components identified through computational analysis of taxonomic groups, sequences, and/or other suitable data associated with diet-related conditions, such as while optimizing for improving specificity, reducing amplification bias, and/or other suitable parameters; etc.); model simplification facilitating efficient interpretation of results; reduction in overfitting; network effects associated with generating, storing, and applying microbiome characterizations for a plurality of users over time in relation to diet-related conditions (e.g., through collecting and processing an increasing amount of microbiome-related data associated with an increasing number of users to improve predictive power of the diet-related characterizations and/or therapy determinations; etc.), improvements in data storage and retrieval (e.g., storing specific models, microorganism sequences, features, diet-related characterizations, and/or other suitable data in association with a user and/or set of users to improve delivery of personalized characterizations and/or health-supporting measures for the diet-related conditions, etc.), and/or other suitable improvements to technological areas.

Third, the technology can transform entities (e.g., users, biological samples, treatment systems including medical devices, etc.) into different states or things. For example, the technology can transform a biological sample into components able to be sequenced and analyzed for characterizing users in relation to diet-related conditions. In another example, the technology can identify therapies to promote to a subject to modify a microbiome composition (e.g., composition diversity), microbiome function (e.g., functional diversity) and/or other microbiome-related aspects associated with the diet-related conditions, thereby transforming the microbiome and/or health of the patient. In another example, the technology can control health-supporting systems to promote health-supporting measures (e.g., by generating control instructions for the health-supporting system to execute), thereby transforming the health-supporting system.

Fourth, the technology can amount to an inventive distribution of functionality across a network including a sample handling system, a diet-related characterization system, and a plurality of users, where the sample handling system can handle substantially concurrent processing of biological samples (e.g., in a multiplex manner) from the plurality of users, which can be leveraged by the diet-related characterization system in generating personalized characterizations and/or health-supporting measures (e.g., customized to the user's microbiome such as in relation to the user's dietary behavior, probiotics-associated behavior, medical history, demographics, other behaviors, preferences, etc.) for diet-related conditions.

Fifth, the technology can improve the technical fields of at least microbiome-related digital medicine, digital medicine generally, genetic sequencing, modeling (e.g., of diet-related conditions associated with microbiomes; etc.) and/or other relevant fields. Sixth, the technology can leverage specialized computing devices (e.g., devices associated with the sample handling system, such as next-generation sequencing platforms; diet-related characterization systems; treatment systems; etc.) in determining and processing microbiome datasets in relation to diet-related characterization and/or therapy provision. The technology can, however, provide any other suitable benefit(s) in the context of using non-generalized computer systems for diet-related characterization and/or microbiome modulation.

3.1 Generating a Microbiome Dataset.

Block S110 recites: generating a microbiome dataset (e.g., microorganism sequence dataset, microbiome composition diversity dataset, microbiome functional diversity dataset, etc.) for each of an aggregate set of biological samples associated with a population of users (e.g., subjects), based on sample processing of the biological samples. Block S110 functions to process each of an aggregate set of biological samples, in order to determine compositional and/or functional aspects associated with the microbiome of each of a population of subjects. Compositional and functional aspects can include compositional aspects at the microorganism level, including parameters related to distribution of microorganisms across different groups of kingdoms, phyla, classes, orders, families, genera, species, subspecies, strains, and/or any other suitable infraspecies taxon (e.g., as measured in total abundance of each group, relative abundance of each group, total number of groups represented, etc.). Compositional and functional aspects can also be represented in terms of operational taxonomic units (OTUs). Compositional and functional aspects can additionally or alternatively include compositional aspects at the genetic level (e.g., regions determined by multilocus sequence typing, 16S sequences, 18S sequences, ITS sequences, other genetic markers, other phylogenetic markers, etc.). Compositional and functional aspects can include the presence or absence or the quantity of genes associated with specific functions (e.g. enzyme activities, transport functions, immune activities, etc.). Outputs of Block S110 can thus be used to provide features of interest for the characterization process of Block S130, wherein the features can be microorganism-based (e.g., presence of a genus of bacteria), genetic-based (e.g., based upon representation of specific genetic regions and/or sequences) and/or functional-based (e.g., presence of a specific catalytic activity).

In one variation, Block S110 can include assessment and/or processing based upon phylogenetic markers derived from bacteria and/or archaea in relation to gene families associated with one or more of: ribosomal protein S2, ribosomal protein S3, ribosomal protein S5, ribosomal protein S7, ribosomal protein S8, ribosomal protein S9, ribosomal protein S10, ribosomal protein S11, ribosomal protein S12/S23, ribosomal protein S13, ribosomal protein S15P/S13e, ribosomal protein S17, ribosomal protein S19, ribosomal protein L1, ribosomal protein L2, ribosomal protein L3, ribosomal protein L4/Lie, ribosomal protein L5, ribosomal protein L6, ribosomal protein L10, ribosomal protein L11, ribosomal protein L14b/L23e, ribosomal protein L15, ribosomal protein L16/L10E, ribosomal protein L18P/L5E, ribosomal protein L22, ribosomal protein L24, ribosomal protein L25/L23, ribosomal protein L29, translation elongation factor EF-2, translation initiation factor IF-2, metalloendopeptidase, ffh signal recognition particle protein, phenylalanyl-tRNA synthetase beta subunit, phenylalanyl-tRNA synthetase alpha subunit, tRNA pseudouridine synthase B, Porphobilinogen deaminase, ribosomal protein L13, phosphoribosylformylglycinamidine cyclo-ligase, and ribonuclease HII. Additionally or alternatively, markers can include target sequences (e.g., sequences associated with a microorganism taxonomic group; sequences associated with functional aspects; sequences correlated with diet-related conditions; sequences indicative of user responsiveness to different therapies; sequences that are invariant across a population and/or any suitable set of subjects, such as to facilitate multiplex amplification using a primer type sharing a primer sequence; conserved sequences; sequences including mutations, polymorphisms; nucleotide sequences; amino acid sequences; etc.), proteins (e.g., serum proteins, antibodies, etc.), peptides, carbohydrates, lipids, other nucleic acids, whole cells, metabolites, natural products, genetic predisposition biomarkers, diagnostic biomarkers, prognostic biomarkers, predictive biomarkers, other molecular biomarkers, gene expression markers, imaging biomarkers, and/or other suitable markers. However, the markers can include any other suitable marker(s) associated with microbiome composition, microbiome functionality, and/or diet-related conditions.

Characterizing the microbiome composition and/or functional features for each of the aggregate set of biological samples thus preferably includes a combination of sample processing techniques (e.g., wet laboratory techniques), including, but not limited to, amplicon sequencing (i.e 16S, 18S, ITS), unique molecule identifiers (UMIs), 3 step PCR, CRISPR, metagenomic approaches, metatranscriptomics, use of random primers, and computational techniques (e.g., utilizing tools of bioinformatics) to quantitatively and/or qualitatively characterize the microbiome and functional features associated with each biological sample from a subject or population of subjects.

In variations, sample processing in Block S110 can include any one or more of: lysing a biological sample, disrupting membranes in cells of a biological sample, separation of undesired elements (e.g., RNA, proteins) from the biological sample, purification of nucleic acids (e.g., DNA) in a biological sample, amplification of nucleic acids from the biological sample, further purification of amplified nucleic acids of the biological sample, and sequencing of amplified nucleic acids of the biological sample. In an example, Block S110 can include: collecting biological samples from a set of users (e.g., biological samples collected by the user with a sampling kit including a sample container, etc.), where the biological samples include microorganism nucleic acids associated with the diet-related condition (e.g., microorganism nucleic acids including target sequences correlated with a diet-related condition; etc.). In another example, Block S110 can include providing a set of sampling kits to a set of users, each sampling kit of the set of sampling kits including a sample container (e.g., including pre-processing reagents, such as lysing reagents; etc.) operable to receive a biological sample from a user of the set of users.

In variations, lysing a biological sample and/or disrupting membranes in cells of a biological sample preferably includes physical methods (e.g., bead beating, nitrogen decompression, homogenization, sonication), which omit certain reagents that produce bias in representation of certain bacterial groups upon sequencing. Additionally or alternatively, lysing or disrupting in Block S110 can involve chemical methods (e.g., using a detergent, using a solvent, using a surfactant, etc.). Additionally or alternatively, lysing or disrupting in Block S110 can involve biological methods. In variations, separation of undesired elements can include removal of RNA using RNases and/or removal of proteins using proteases. In variations, purification of nucleic acids can include one or more of: precipitation of nucleic acids from the biological samples (e.g., using alcohol-based precipitation methods), liquid-liquid based purification techniques (e.g., phenol-chloroform extraction), chromatography-based purification techniques (e.g., column adsorption), purification techniques involving use of binding moiety-bound particles (e.g., magnetic beads, buoyant beads, beads with size distributions, ultrasonically responsive beads, etc.) configured to bind nucleic acids and configured to release nucleic acids in the presence of an elution environment (e.g., having an elution solution, providing a pH shift, providing a temperature shift, etc.), and any other suitable purification techniques.

In variations, amplification of purified nucleic acids preferably includes one or more of: polymerase chain reaction (PCR)-based techniques (e.g., solid-phase PCR, RT-PCR, qPCR, multiplex PCR, touchdown PCR, nanoPCR, nested PCR, hot start PCR, etc.), helicase-dependent amplification (HDA), loop mediated isothermal amplification (LAMP), self-sustained sequence replication (3SR), nucleic acid sequence based amplification (NASBA), strand displacement amplification (SDA), rolling circle amplification (RCA), ligase chain reaction (LCR), and any other suitable amplification technique. In amplification of purified nucleic acids, the primers used are preferably selected to prevent or minimize amplification bias, as well as configured to amplify nucleic acid regions/sequences (e.g., of the 16S region, the 18S region, the ITS region, etc.) that are informative taxonomically, phylogenetically, for diagnostics, for formulations (e.g., for probiotic formulations), and/or for any other suitable purpose. Thus, universal primers (e.g., a F27-R338 primer set for 16S RNA, a F515-R806 primer set for 16S RNA, etc.) configured to avoid amplification bias can be used in amplification. Primers used in variations of Block S110 can additionally or alternatively include incorporated barcode sequences and or UMIs (reference patent) specific to each biological sample, which can facilitate identification of biological samples post-amplification. Primers used in variations of Block S110 can additionally or alternatively include adaptor regions configured to cooperate with sequencing techniques involving complementary adaptors (e.g., Illumina Sequencing). Additionally or alternatively, Block S110 can implement any other step configured to facilitate processing (e.g., using a Nextera kit). In a specific example, performing amplification and/or sample processing operations can be in a multiplex manner (e.g., for a single biological sample, for a plurality of biological samples across multiple users; etc.). In another specific example, performing amplification can include normalization steps to balance libraries and detect all amplicons in a mixture independent of the amount of starting material, such as 3 step PCR, bead based normalization, etc.

In variations, sequencing of purified nucleic acids can include methods involving targeted amplicon sequencing, metatranscriptomic sequencing and/or metagenomic sequencing, implementing techniques including one or more of: sequencing-by-synthesis techniques (e.g., Illumina sequencing), capillary sequencing techniques (e.g., Sanger sequencing), pyrosequencing techniques, and nanopore sequencing techniques (e.g., using an Oxford Nanopore technique).

In a specific example, amplification and sequencing of nucleic acids from biological samples of the set of biological samples includes: solid-phase PCR involving bridge amplification of DNA fragments of the biological samples on a substrate with oligo adapters, wherein amplification involves primers having a forward index sequence (e.g., corresponding to an Illumina forward index for MiSeq/NextSeq/HiSeq platforms), a forward barcode sequence, a transposase sequence (e.g., corresponding to a transposase binding site for MiSeq/NextSeq/HiSeq platforms), a linker (e.g., a zero, one, or two-base fragment configured to reduce homogeneity and improve sequence results), an additional random base, UMIs, a sequence for targeting a specific target region (e.g., 16S region, 18S region, ITS region), a reverse index sequence (e.g., corresponding to an Illumina revers index for MiSeq/HiSeq platforms), and a reverse barcode sequence. In the specific example, sequencing comprises Illumina sequencing (e.g., with a HiSeq platform, with a MiSeq platform, with a NextSeq platform, etc.) using a sequencing-by-synthesis technique.

In variations, primers (e.g., of a primer type corresponding to a primer sequence; etc.) used in Block S110 and/or other suitable portions of the method 100 can include primers associated with protein genes (e.g., coding for conserved protein gene sequences across a plurality of taxa, such as to enable multiplex amplification for a plurality of targets and/or taxa; etc.). Primers can additionally or alternatively be associated with diet-related conditions, microbiome composition features (e.g., identified primers compatible with a genetic target corresponding to microbiome composition features associated with a group of taxa correlated with a diet-related condition; genetic sequences from which relative abundance features are derived etc.), functional diversity features, supplementary features, and/or other suitable features and/or data. Primers (and/or other suitable molecules, markers, and/or biological material described herein) can possess any suitable size (e.g., sequence length, number of base pairs, conserved sequence length, variable region length, etc.). Additionally or alternatively, any suitable number of primers can be used in sample processing for performing characterizations (e.g., diet-related characterizations; etc.), improving sample processing (e.g., through reducing amplification bias, etc.), and/or for any suitable purposes. The primers can be associated with any suitable number of targets, sequences, taxa, conditions, and/or other suitable aspects. Primers used in Block S110 and/or other suitable portions of the method 100 can be selected through processes described in Block S110 (e.g., primer selection based on parameters used in generating the taxonomic database) and/or any other suitable portions of the method 100. In an example, Block S110 can include: identifying a primer type for a microorganism nucleic acid sequence associated with the diet-related condition (e.g., a primer type for a primer operable to amplify microorganism nucleic acid sequences correlated with a diet-related condition; etc.); and generating the microorganism sequence dataset based on the primer type and the microorganism nucleic acids (e.g., using primers of the primer type for amplification of microorganism nucleic acids; and sequencing the amplified nucleic acids to generate the microorganism sequence dataset; etc.). In a specific example, Block S110 can include: fragmenting the microorganism nucleic acids; and performing multiplex amplification with the fragmented microorganism nucleic acids based on the fragmented microorganism nucleic acids and the identified primer type associated with the diet-related condition. Additionally or alternatively, primers (and/or processes associated with primers) can include and/or be analogous to that described in U.S. application Ser. No. 14/919, 614, filed 21 Oct. 2015 and/or U.S. application Ser. No. 15/240,919, filed 18 Aug. 2016, which are each herein incorporated in their entireties by this reference. However, identification and/or usage of primers can be configured in any suitable manner.

Some variations of sample processing can include further purification of amplified nucleic acids (e.g., PCR products) prior to sequencing, which functions to remove excess amplification elements (e.g., primers, dNTPs, enzymes, salts, etc.). In examples, additional purification can be facilitated using any one or more of: purification kits, buffers, alcohols, pH indicators, chaotropic salts, nucleic acid binding filters, centrifugation, and any other suitable purification technique.

In variations, computational processing in Block S110 can include any one or more of: identification of microbiome-derived sequences (e.g., as opposed to subject sequences and contaminants), alignment and mapping of microbiome-derived sequences (e.g., alignment of fragmented sequences using one or more of single-ended alignment, ungapped alignment, gapped alignment, pairing), and generating features derived from compositional and/or functional aspects of the microbiome associated with a biological sample.

Identification of microbiome-derived sequences can include mapping of sequence data from sample processing to a subject reference genome (e.g., provided by the Genome Reference Consortium), in order to remove subject genome-derived sequences. Unidentified sequences remaining after mapping of sequence data to the subject reference genome can then be further clustered into operational taxonomic units (OTUs) based upon sequence similarity and/or reference-based approaches (e.g., using VAMPS, using MG-RAST, using QIIME databases), aligned (e.g., using a genome hashing approach, using a Needleman-Wunsch algorithm, using a Smith-Waterman algorithm), and mapped to reference bacterial genomes (e.g., provided by the National Center for Biotechnology Information), using an alignment algorithm (e.g., Basic Local Alignment Search Tool, FPGA accelerated alignment tool, BWT-indexing with BWA, BWT-indexing with SOAP, BWT-indexing with Bowtie, etc.). Mapping of unidentified sequences can additionally or alternatively include mapping to reference archaeal genomes, viral genomes and/or eukaryotic genomes. Furthermore, mapping of taxons can be performed in relation to existing databases, and/or in relation to custom-generated databases.

Upon identification of represented groups of microorganisms of the microbiome associated with a biological sample, generating features derived from compositional and functional aspects of the microbiome associated with a biological sample can be performed. In one variation, generating features can include generating features based upon multilocus sequence typing (MSLT), in order to identify markers useful for characterization in subsequent blocks of the method 100. Additionally or alternatively, generated features can include generating features that describe the presence or absence of certain taxonomic groups of microorganisms, and/or ratios between exhibited taxonomic groups of microorganisms. Additionally or alternatively, generating features can include generating features describing one or more of: quantities of represented taxonomic groups, networks of represented taxonomic groups, correlations in representation of different taxonomic groups, interactions between different taxonomic groups, products produced by different taxonomic groups, interactions between products produced by different taxonomic groups, ratios between dead and alive microorganisms (e.g., for different represented taxonomic groups, based upon analysis of RNAs), phylogenetic distance (e.g., in terms of Kantorovich-Rubinstein distances, Wasserstein distances etc.), any other suitable taxonomic group-related feature(s), any other suitable genetic or functional feature(s).

Additionally or alternatively, generating features can include generating features describing relative abundance of different microorganism groups, for instance, using a sparCC approach, using Genome Relative Abundance and Average size (GAAS) approach and/or using a Genome Relative Abundance using Mixture Model theory (GRAMMy) approach that uses sequence-similarity data to perform a maximum likelihood estimation of the relative abundance of one or more groups of microorganisms. Additionally or alternatively, generating features can include generating statistical measures of taxonomic variation, as derived from abundance metrics. Additionally or alternatively, generating features can include generating features derived from relative abundance factors (e.g., in relation to changes in abundance of a taxon, which affects abundance of other taxons). Additionally or alternatively, generating features can include generation of qualitative features describing presence of one or more taxonomic groups, in isolation and/or in combination. Additionally or alternatively, generating features can include generation of features related to genetic markers (e.g., representative 16S, 18S, and/or ITS sequences) characterizing microorganisms of the microbiome associated with a biological sample. Additionally or alternatively, generating features can include generation of features related to functional associations of specific genes and/or organisms having the specific genes. Additionally or alternatively, generating features can include generation of features related to pathogenicity of a taxon and/or products attributed to a taxon. Block S120 can, however, include generation of any other suitable feature(s) derived from sequencing and mapping of nucleic acids of a biological sample. For instance, the feature(s) can be combinatory (e.g. involving pairs, triplets), correlative (e.g., related to correlations between different features), and/or related to changes in features (i.e., temporal changes, changes across sample sites, etc., spatial changes, etc.). However, processing biological samples, generating a microbiome dataset, and/or other aspects associated with Block S110 can be performed in any suitable manner.

3.2 Processing a Supplementary Dataset.

Block S120 recites: processing (e.g., receiving, collecting, transforming, etc.) a supplementary dataset associated with (e.g., informative of; describing; indicative of; etc.) one or more diet-related conditions for the set of users. Block S120 functions to acquire additional data associated with one or more subjects of the set of subjects, which can be used to train and/or validate the diet-related characterization process generated in Block S130. In Block S120, the supplementary dataset preferably includes survey-derived data, but can additionally or alternatively include any one or more of: contextual data derived from sensors, medical data (e.g., current and historical medical data), and any other suitable type of data. In variations of Block S120 including reception of survey-derived data, the survey-derived data preferably provides physiological, demographic, and behavioral information in association with a subject. Physiological information can include information related to physiological features (e.g., height, weight, body mass index, body fat percent, body hair level, etc.). Demographic information can include information related to demographic features (e.g., gender, age, ethnicity, marital status, number of siblings, socioeconomic status, sexual orientation, etc.). Behavioral information can include information related to one or more of: health conditions (e.g., health and disease states), living situations (e.g., living alone, living with pets, living with a significant other, living with children, etc.), dietary habits (e.g., omnivorous, vegetarian, vegan, sugar consumption, acid consumption, etc.), behavioral tendencies (e.g., levels of physical activity, drug use, alcohol use, etc.), different levels of mobility (e.g., related to distance traveled within a given time period), different levels of sexual activity (e.g., related to numbers of partners and sexual orientation), and any other suitable behavioral information. Survey-derived data can include quantitative data and/or qualitative data that can be converted to quantitative data (e.g., using scales of severity, mapping of qualitative responses to quantified scores, etc.).

In facilitating reception of survey-derived data, Block S130 can include providing one or more surveys to a subject of the population of subjects, or to an entity associated with a subject of the population of subjects. Surveys can be provided in person (e.g., in coordination with sample provision and reception from a subject), electronically (e.g., during account setup by a subject, at an application executing at an electronic device of a subject, at a web application accessible through an internet connection, etc.), and/or in any other suitable manner.

Additionally or alternatively, portions of the supplementary dataset can be derived from sensors associated with the subject(s) (e.g., sensors of wearable computing devices, sensors of mobile devices, biometric sensors associated with the user, etc.). As such, Block S130 can include receiving one or more of: physical activity- or physical action-related data (e.g., accelerometer and gyroscope data from a mobile device or wearable electronic device of a subject), environmental data (e.g., temperature data, elevation data, climate data, light parameter data, etc.), patient nutrition or diet-related data (e.g., data from food establishment check-ins, data from spectrophotometric analysis, etc.), biometric data (e.g., data recorded through sensors within the patient's mobile computing device, data recorded through a wearable or other peripheral device in communication with the patient's mobile computing device), location data (e.g., using GPS elements), and any other suitable data. In variations, sensor data can include data sampled at one or more: optical sensors (e.g., image sensors, light sensors, etc.), audio sensors, temperature sensors, volatile compound sensors, weight sensors, humidity sensors, depth sensors, location sensors (GPS receivers; etc.), inertial sensors (e.g., accelerators, gyroscope, magnetometer, etc.), biometric sensors (e.g., heart rate sensors, fingerprint sensors, bio-impedance sensors, etc.), pressure sensors, flow sensors, power sensors (e.g., Hall effect sensors), and/or or any other suitable sensor.

Additionally or alternatively, portions of the supplementary dataset can be derived from medical record data and/or clinical data of the subject(s). As such, portions of the supplementary dataset can be derived from one or more electronic health records (EHRs) of the subject(s).

Additionally or alternatively, the supplementary dataset of Block S120 can include any other suitable diagnostic information (e.g., clinical diagnosis information), which can be combined with analyses derived from features to support characterization of subjects in subsequent blocks of the method 100. For instance, information derived from a colonoscopy, biopsy, blood test, diagnostic imaging, survey-related information, and any other suitable test can be used to supplement Block S120.

Additionally or alternatively, the supplementary dataset can include health supporting measure-related data including one or more of: dietary regimens, exercise regimens, health-supporting regimens related to specific diets, types of therapies, recommended therapies, therapies used by the user, therapy adherence, etc. For example, the supplementary dataset can include user adherence (e.g., medication adherence, probiotic adherence, physical exercise adherence, dietary adherence, etc.) to a recommended therapy. However, processing supplementary datasets can be performed in any suitable manner.

3.3 Performing a Characterization Process.

Block S130 recites: performing a characterization process for the one or more diet-related conditions, based on the supplementary dataset and microbiome features (e.g., microbiome composition diversity features; microbiome functional diversity features; etc.) extracted from the microbiome dataset. Block S130 functions to identify features and/or feature combinations that can be used to characterize subjects or groups based upon their microbiome composition and/or functional features. As such, the characterization process can be used as an assessment tool that can characterize a subject (e.g., in terms of behavioral traits, in terms of medical conditions, in terms of demographic traits, etc.) based upon their microbiome composition and/or functional features, in relation to one or more of their health condition states, behavioral traits, medical conditions, demographic traits, and any other suitable traits. Such characterization can then be used to suggest or provide personalized health supporting measures by way of the therapy model of Block S140.

In performing the characterization process, Block S130 can use computational methods (e.g., statistical methods, machine learning methods, artificial intelligence methods, bioinformatics methods, etc.) to characterize a subject as exhibiting features characteristic of a group of subjects with a health condition.

In one variation, characterization can be based upon features derived from a statistical analysis (e.g., an analysis of probability distributions) of similarities and/or differences between a first group of subjects exhibiting a target state (e.g., a diet-related state) and a second group of subjects not exhibiting the target state (e.g., a control state, another diet-related state). In implementing this variation, one or more of a Kolmogorov-Smirnov (KS) test, a permutation test, a Cramér-von Mises test, and any other statistical test (e.g., t-test, z-test, chi-squared test, test associated with distributions, etc.) can be used. In particular, one or more such statistical hypothesis tests can be used to assess a set of features having varying degrees of abundance in a first group of subjects exhibiting a target state (i.e., a first diet-related state) and a second group of subjects not exhibiting the target state (i.e., having a control state, having another diet-related state). In more detail, the set of features assessed can be constrained based upon percent abundance and/or any other suitable parameter pertaining to diversity in association with the first group of subjects and the second group of subjects, in order to increase or decrease confidence in the characterization. In a specific implementation of this example, a feature can be derived from a taxon of bacteria that is abundant in a certain percentage of subjects of the first group and subjects of the second group, wherein a relative abundance of the taxon between the first group of subjects and the second group of subjects can be determined from the KS test, with an indication of significance (e.g., in terms of p-value). Thus, an output of Block S130 can comprise a normalized relative abundance value (e.g., 25% greater abundance of a taxon in sick subjects vs. healthy subjects) with an indication of significance (e.g., a p-value of 0.0013). Variations of feature generation can additionally or alternatively implement or be derived from functional features or metadata features (e.g., non-bacterial markers). Additionally or alternatively, any suitable microbiome features can be derived based on statistical analyses (e.g., applied to a microorganism sequence dataset and/or other suitable microbiome dataset, etc.) including any one or more of: a prediction analysis, multi hypothesis testing, a random forest test, and principal component analysis.

In performing the characterization process, Block S130 can additionally or alternatively transform input data from at least one of the microbiome composition diversity dataset and microbiome functional diversity dataset into feature vectors that can be tested for efficacy in predicting characterizations of the population of subjects. Data from the supplementary dataset can be used to provide indication of one or more characterizations of a set of characterizations, wherein the characterization process is trained with a training dataset of candidate features and candidate classifications to identify features and/or feature combinations that have high degrees (or low degrees) of predictive power in accurately predicting a classification. As such, refinement of the characterization process with the training dataset identifies feature sets (e.g., of subject features, of combinations of features) having high correlation with specific classifications of subjects.

In variations, feature vectors (and/or any suitable set of features) effective in predicting classifications of the characterization process can include features related to one or more of: microbiome diversity metrics (e.g., in relation to distribution across taxonomic groups, in relation to distribution across archaeal, bacterial, viral, and/or eukaryotic groups), presence of taxonomic groups in one's microbiome, representation of specific genetic sequences (e.g., 16S sequences) in one's microbiome, relative abundance of taxonomic groups in one's microbiome, microbiome resilience metrics (e.g., in response to a perturbation determined from the supplementary dataset), abundance of genes that encode proteins or RNAs with given functions (enzymes, transporters, proteins from the immune system, hormones, interference RNAs, etc.) and any other suitable features derived from the microbiome diversity dataset and/or the supplementary dataset. In variations, microbiome features can be associated with (e.g., include, correspond to, typify, etc.) at least one of: presence of a microbiome feature from the microbiome features, absence of the microbiome features from the microbiome features, relative abundance of different taxonomic groups associated with the diet-related condition; a ratio between at least two microbiome features associated with the different taxonomic groups, interactions between the different taxonomic groups, and phylogenetic distance between the different taxonomic groups. In a specific example, microbiome features can include one or more relative abundance characteristics associated with at least one of the microbiome composition diversity features (e.g., relative abundance associated with different taxa, etc.) and the microbiome functional diversity features (e.g., relative abundance of sequences corresponding to different functional features; etc.). Relative abundance characteristics and/or other suitable microbiome features (and/or other suitable data described herein) can be extracted and/or otherwise determined based on: a normalization, a feature vector derived from at least one of linear latent variable analysis and non-linear latent variable analysis, linear regression, non-linear regression, a kernel method, a feature embedding method, a machine learning method, and a statistical inference method. Additionally or alternatively, combinations of features can be used in a feature vector, where features can be grouped and/or weighted in providing a combined feature as part of a feature set. For example, one feature or feature set can include a weighted composite of the number of represented classes of bacteria in one's microbiome, presence of a specific genus of bacteria in one's microbiome, representation of a specific 16S sequence in one's microbiome, and relative abundance of a first phylum over a second phylum of bacteria. However, the feature vectors can additionally or alternatively be determined in any other suitable manner.

Figure 3:
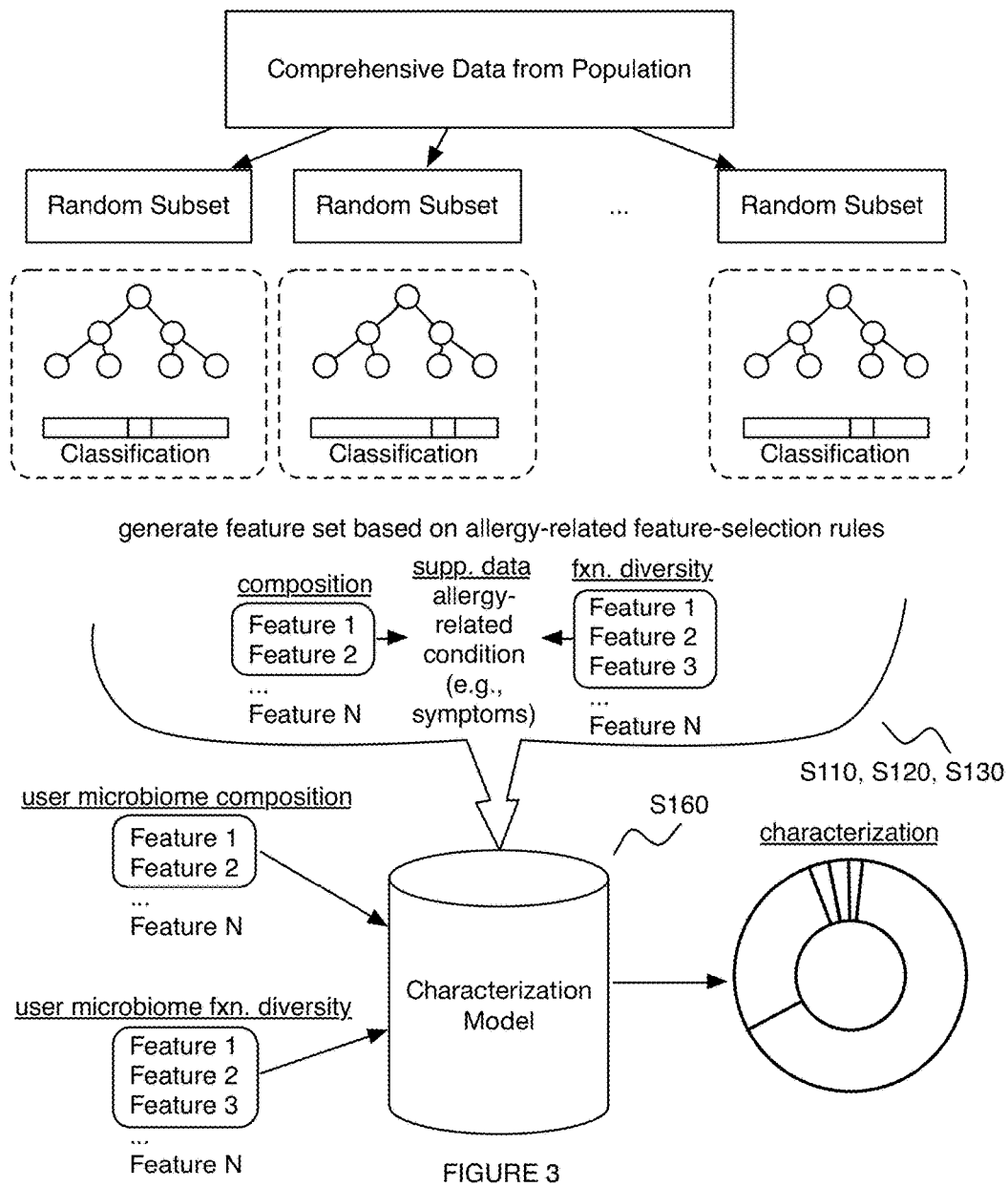
FIG. 3 depicts a variation of a process for generation of a characterization model in an embodiment of a method.

As shown in FIG. 3, in one such alternative variation of Block S130, the characterization process can be generated and trained according to a random forest predictor (RFP) algorithm that combines bagging (e.g., bootstrap aggregation) and selection of random sets of features from a training dataset to construct a set of decision trees, T, associated with the random sets of features. In using a random forest algorithm, N cases from the set of decision trees are sampled at random with replacement to create a subset of decision trees, and for each node, m prediction features are selected from all of the prediction features for assessment. The prediction feature that provides the best split at the node (e.g., according to an objective function) is used to perform the split (e.g., as a bifurcation at the node, as a trifurcation at the node). By sampling many times from a large dataset, the strength of the characterization process, in identifying features that are strong in predicting classifications can be increased substantially. In this variation, measures to prevent bias (e.g., sampling bias) and/or account for an amount of bias can be included during processing to increase robustness of the model.

Additionally or alternatively, Block S130 (e.g., extracting microbiome features; generating characterization models for diet-related conditions; etc.) and/or other suitable portions of the method 100 (e.g., determining a diet-related characterization; determining and/or providing a therapy; etc.) can employ data processing approaches including any one or more of: performing pattern recognition on data (e.g., identifying correlations between diet-related conditions and microbiome features; etc.), fusing data from multiple sources (e.g., generating characterization models based on microbiome data and/or supplementary data from a plurality of users associated with one or more diet-related conditions; etc.), combination of values (e.g., averaging values, etc.), compression, conversion (e.g., digital-to-analog conversion, analog-to-digital conversion), performing statistical estimation on data (e.g. ordinary least squares regression, non-negative least squares regression, principal components analysis, ridge regression, etc.), wave modulation, normalization, updating (e.g., of characterization models and/or therapy models based on processed biological samples over time; etc.), ranking (e.g., microbiome features; therapies; etc.), weighting (e.g., microbiome features; etc.), validating, filtering (e.g., for baseline correction, data cropping, etc.), noise reduction, smoothing, filling (e.g., gap filling), aligning, model fitting, binning, windowing, clipping, transformations, mathematical operations (e.g., derivatives, moving averages, summing, subtracting, multiplying, dividing, etc.), data association, multiplexing, demultiplexing, interpolating, extrapolating, clustering, image processing techniques, other signal processing operations, other image processing operations, visualizing, and/or any other suitable processing operations. However, data processing for facilitating any suitable portions of the method 100 can be performed in any suitable manner.

In a variation, Block S130 and/or other portions of the method 100 can include applying computer-implemented rules (e.g., models, feature selection rules, etc.) to process population-level data, but can additionally or alternatively include applying computer-implemented rules to process microbiome-related data on a demographic-specific basis (e.g., subgroups sharing a demographic feature such as diet-relation conditions therapy regiments, dietary regiments, physical activity regiments, ethnicity, age, gender, weight, sleeping behaviors, etc.), condition-specific basis (e.g., subgroups exhibiting a specific diet-related condition, a combination of diet-related conditions, triggers for the diet-related conditions, associated symptoms, etc.), a sample type-specific basis (e.g., applying different computer-implemented rules to process microbiome data derived from different collection sites; etc.), a user basis (e.g., different computer-implemented rules for different users; etc.) and/or any other suitable basis. As such, Block S130 can include assigning users from the population of users to one or more subgroups; and applying different computer-implemented rules for determining features (e.g., the set of feature types used; the types of characterization models generated from the features; etc.) for the different subgroups. However, applying computer-implemented rules can be performed in any suitable manner.

In another variation, Block S130 can include processing (e.g., generating, training, updating, executing, storing, etc.) one or more characterization models (e.g., diet-related condition characterization models, etc.) for one or more diet-related conditions. The characterization models preferably leverage microbiome features as inputs, and preferably output diet-related characterizations and/or any suitable components thereof; but characterization models can use and suitable inputs to generate any suitable outputs. In an example, Block S130 can include transforming the supplementary data, the microbiome composition diversity features, and the microbiome functional diversity features into a characterization model (e.g., training a diet-related characterization model based on the supplementary data and microbiome features; etc.) for the diet-related condition. In another example, the method 100 can include: determining a population microorganism sequence dataset (e.g., including microorganism sequence outputs for different users of the population; etc.) for a population of users associated with one or more diet-related conditions, based on a set of samples from the population of users (e.g., and/or based on one or more primer types associated with the diet-related condition; etc.); collecting a supplementary dataset associated with diagnosis of the one or more diet-related conditions for the population of subjects; and generating the diet-related condition characterization model based on the population microorganism sequence dataset and the supplementary dataset.

Figure 8A:
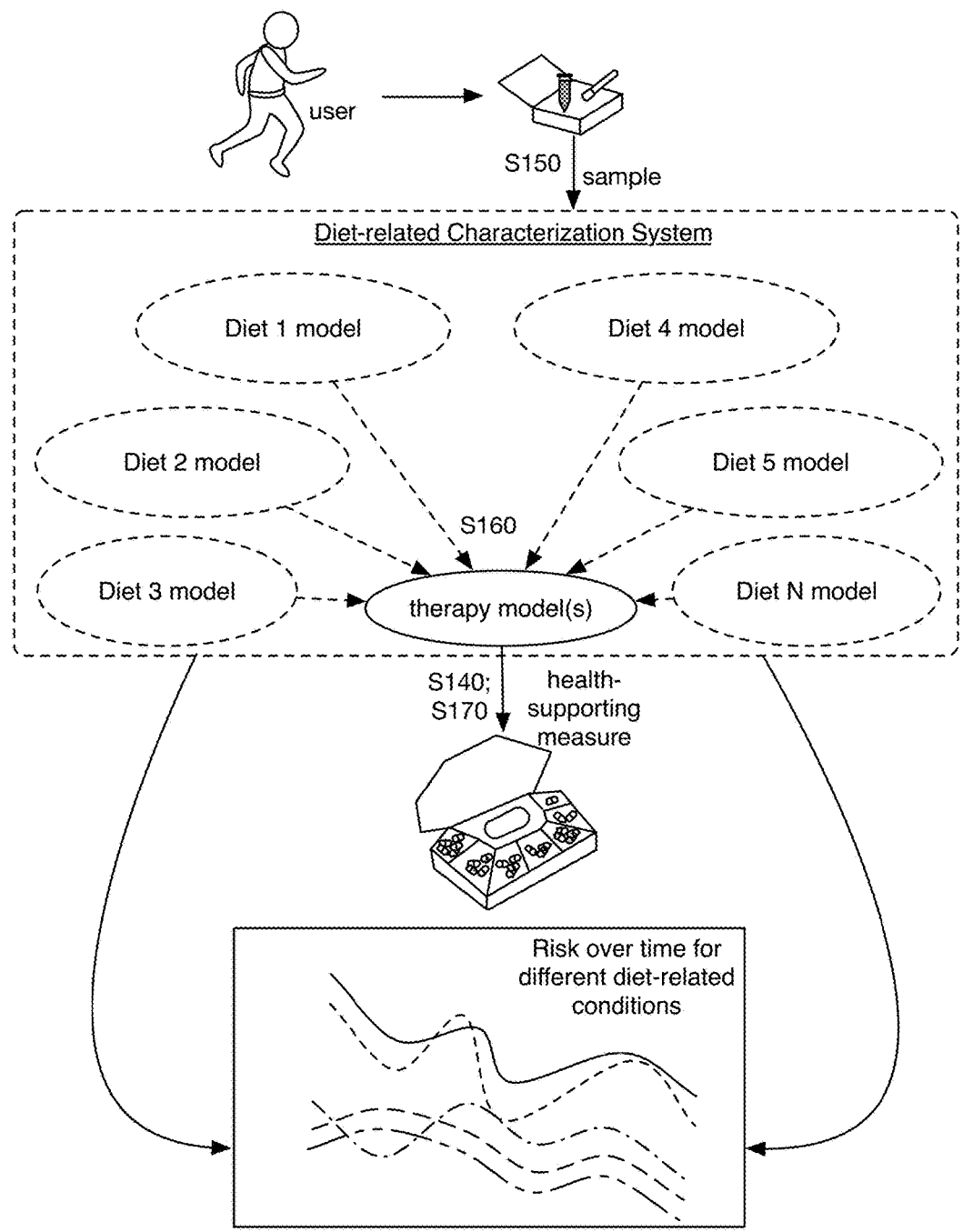
FIGS. 8A-8B depicts variations of performing characterization processes with diet-related models.
Figure 8B:
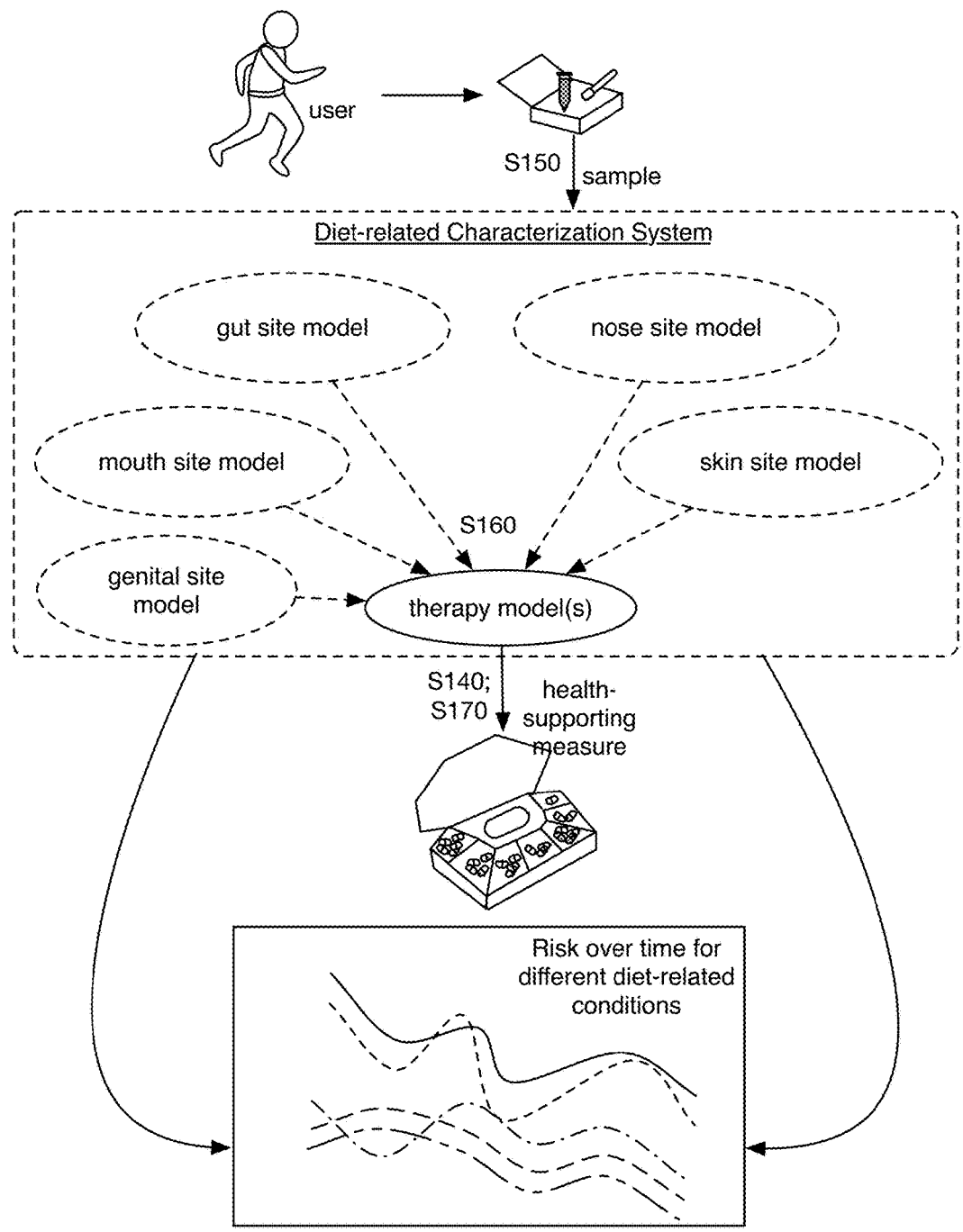

In another variation, as shown in FIGS. 8A-8B, different diet-related characterization models and/or other suitable models (e.g., generated with different algorithms, with different sets of features, with different input and/or output types, applied in different manners such as in relation to time, frequency, component applying the model, etc.) can be generated for different demographic groups (e.g., a first characterization model for users on a dietary regimen including food items associated with the diet-related condition, and a second characterization model for users on a different dietary regimen; different models based on physical activity level; different models based on age, gender, weight, height, ethnicity; etc.), different physiological sites (e.g., a gut site model, a nose site model, a skin site model, a mouth site model, a genitals site model, etc.), diet-related conditions (e.g., different characterization models for users with different diet-related conditions; etc.), individual users, supplementary data (e.g., models incorporating features derived from biometric sensor data and/or survey response data vs. models independent of supplementary data, etc.), and/or other suitable criteria.

In variations, determining diet-related characterizations and/or any other suitable characterizations for conditions associated with microorganisms can include determining diet-related characterizations in relation to specific physiological sites (e.g., gut, healthy gut, skin, nose, mouth, genitals, other suitable physiological sites, other sample collection sites, etc.), such as through any one or more of: determining a diet-related characterization based on a diet-related characterization model derived based on site-specific data (e.g., defining correlations between a diet-related condition and microbiome features associated with one or more physiological sites); determining a diet-related characterization based on a user biological sample collected at one or more physiological sites, and/or any other suitable site-related processes. In examples, machine learning approaches (e.g., classifiers, deep learning algorithms), statistical tests, dimension reduction approaches, and/or other suitable approaches (e.g., described herein) can be applied in determining site-related (e.g., physiological site-related, etc.) characterizations, other suitable characterizations, therapies, and/or any other suitable outputs. However, the method 100 can include determining any suitable site-related (e.g., site-specific) outputs, and/or performing any suitable portions of the method 100 (e.g., collecting samples, processing samples, determining therapies) with site-specificity and/or other site-relatedness in any suitable manner.

However, performing a characterization process S130 can be performed in any suitable manner.

3.3.A Characterization Process: Vegetarian and Vegan Diets Vs. Omnivorous and Raw Meat Diets.

In a variation, Block S130 can include performing a diet condition characterization process (e.g., determining and/or applying a diet characterization model; etc.) for one or more users, in relation to at least one of two diet sets: vegetarian & vegan diets vs omnivorous & raw meat diets. In an example, a characterization process (e.g., of Block S130; based upon statistical analyses and/or other suitable approaches described herein; etc.) can identify a set of microbiome features (e.g., microbiome composition features, microbiome function features, etc.) with correlations (e.g., positive correlations, negative correlations, correlations of greatest magnitude, etc.) with at least one of the above diet conditions. In another example, performing a diet condition characterization process can facilitate identifications of one or more health-supporting measures operable to have a positive effect or maintaining effect for subjects with at least one of the above diets (e.g., based upon a random forest predictor algorithm trained with a training dataset derived from a subset of the population of subjects, and validated with a validation dataset derived from a subset of the population of subjects). In particular, at least one of the above dietary conditions can be a lifestyle behavior chosen by the subject, characterized by limited ingestion of some foods or ingestion of some foods only (e.g., no red meat diet, vegetable-only diet, no dietary restriction, etc.) or otherwise associated with a particular dietary regimen (e.g., Vegan diet, Vegetarian diet, Omnivorous diet, etc.) that the subject incorporates as a dietary habit for at least a set time of period that the subject incorporates. The dietary condition can also be associated also with physiological changes that have an effect on the individuals health or health goals (i.e: loss of weight, improvement of concentration, etc.), wherein physiological changes can be associated with an improvement in the health state of a subject that can be measured by medical history (i.e: medical interview), laboratory analysis (i.e: blood sample test, biopsy, etc.), physical measurements (i.e: body mass index, percent body fat, etc.), exercise achievements and any other suitable manner or medical equipment-associated assessment that measures differences in body components levels, metabolic factors, and health conditions (e.g., within a period of time).

Performing the characterization process of the at least one of two diet sets (i.e., vegetarian & vegan diets vs omnivorous & raw meat diets) can be based on microbiome features (e.g., microbiome composition features) associated with (e.g., derived from, informative of, correlated with, etc.) one or more (e.g. in any suitable combination) of the following taxons: *Odoribacter splanchnicus* (species), *Alistipes putredinis* (species), *Collinsella aerofaciens* (species), *Parabacteroides distasonis* (species), *Flavonifractor plautii* (species), *Dorea formicigenerans* (species), *Clostridium* (genus), *Odoribacter* (genus), *Bilophila* (genus), *Parabacteroides* (genus), *Dorea* (genus), *Phascolarctobacterium* (genus), *Anaerostipes* (genus), *Butyricimonas* (genus), *Oscillospira* (genus), Porphyromonadaceae (family), Desulfovibrionaceae (family), Sutterellaceae (family), Acidaminococcaceae (family), Coriobacteriaceae (family), Bifidobacteriaceae (family), Oscillospiraceae (family), Pasteurellaceae (family), Desulfovibrionales (order), Burkholderiales (order), Coriobacteriales (order), Lactobacillales (order), Deltaproteobacteria (class) Betaproteobacteria (class), Bacilli (class), and Proteobacteria_1224 (phylum).

Additionally or alternatively, performing the characterization process of the at least one of two diet sets (i.e., vegetarian & vegan diets vs omnivorous & raw meat diets) can be based on microbiome features (e.g., microbiome function features) associated with one or more of (e.g., such as in relation to a corresponding sample site): [D] Cell cycle control functions, cell division functions, chromosome partitioning functions (COG2), [R] General function prediction only functions (COG2), Phosphatidylinositol signaling system functions (KEGG3), Other transporters functions (KEGG3), K07024-associated functions (KEGG4), K03545-associated functions (KEGG4), K04043-associated functions (KEGG4), and/or any other suitable function-related features.

Determining a diet-related characterization of a user can include characterizing a user with the at least one of two diet sets (i.e., vegetarian & vegan diets vs omnivorous & raw meat diets) based upon one or more of the above microbiome features and/or other suitable features described herein, such as in an additional or alternative manner to typical methods of diagnosis or characterization. However, features used in the diet characterization process can include any other suitable features (e.g., features useful for diagnostics), and performing the characterization process for the at least one of two diet sets (i.e., vegetarian & vegan diets vs omnivorous & raw meat diets) can be performed in any suitable manner.

3.3.B Characterization Process: Low Carbohydrate Diets Vs Omnivorous & Raw Meat Diets.

In another variation, Block S130 can include performing a diet condition characterization process (e.g., determining and/or applying a diet characterization model; etc.) for one or more users, in relation to at least one of two diet sets: low carbohydrate diets vs omnivorous & raw meat diets. In an example, a characterization process (e.g., of Block S130; based upon statistical analyses and/or other suitable approaches described herein; etc.) can identify a set of microbiome features (e.g., microbiome composition features, microbiome function features, etc.) with correlations (e.g., positive correlations, negative correlations, correlations of greatest magnitude, etc.) with at least one of the above diet conditions. In another example, performing a diet condition characterization process can facilitate identifications of one or more health-supporting measures operable to have a positive effect or maintaining effect for subjects with at least one of the above diets (e.g., based upon a random forest predictor algorithm trained with a training dataset derived from a subset of the population of subjects, and validated with a validation dataset derived from a subset of the population of subjects). In particular, at least one of the above dietary conditions can be a lifestyle behavior chosen by the subject, characterized by limited ingestion of some foods or ingestion of some foods only (e.g., no red meat diet, vegetable-only diet, no dietary restriction, etc.) or otherwise associated with a particular dietary regimen (e.g., Vegan diet, Vegetarian diet, Omnivorous diet, etc.) that the subject incorporates as a dietary habit for at least a set time of period that the subject incorporates. The dietary condition can also be associated also with physiological changes that have an effect on the individuals health or health goals (i.e: loss of weight, improvement of concentration, etc.), wherein physiological changes can be associated with an improvement in the health state of a subject that can be measured by medical history (i.e: medical interview), laboratory analysis (i.e: blood sample test, biopsy, etc.), physical measurements (i.e: body mass index, percent body fat, etc.), exercise achievements and any other suitable manner or medical equipment-associated assessment that measures differences in body components levels, metabolic factors, and health conditions (e.g., within a period of time).

Performing the characterization process of the at least one of two diet sets (i.e., low carbohydrate diets vs omnivorous & raw meat diets) can be based on microbiome features (e.g., microbiome composition features) associated with (e.g., derived from, informative of, correlated with, etc.) one or more (e.g. in any suitable combination) of the following taxons: *Blautia luti* (species), *Blautia wexlereae* (species), *Blautia obeum* (species), *Sutterella wadsworthensis* (species), *Bifidobacterium longum* (species), *Collinsella aerofaciens* (species), *Bifidobacterium* (genus), *Roseburia* (genus), *Moryella* (genus), *Odoribacter* (genus), *Bacteroides* (genus), Bifidobacteriaceae (family), Ruminococcaceae (family), Desulfovibrionaceae (family), Clostridiaceae (family), Bacteroidaceae (family), Bifidobacteriales (order), Bacteroidales (order), Desulfovibrionales (order), Clostridiales (order), Bacteroidia (class), Deltaproteobacteria (class), Clostridia (class), Bacteroidetes (phylum), Firmicutes (phylum), and Actinobacteria (phylum).

Additionally or alternatively, performing the characterization process of the at least one of two diet sets (i.e., low carbohydrate diets vs omnivorous & raw meat diets) can be based on microbiome features (e.g., microbiome function features) associated with one or more of (e.g., such as in relation to a corresponding sample site): Metabolism functions (KEGG2), Transport and Catabolism functions (KEGG2), Glycan Biosynthesis and Metabolism functions (KEGG2), Cellular Processes and Signaling functions (KEGG2), Poorly Characterized functions (KEGG2), Environmental Adaptation functions (KEGG2), Translation functions (KEGG2), Neurodegenerative Diseases functions (KEGG2), Huntington's disease functions (KEGG3), MAPK signaling pathway—yeast functions (KEGG3), Lipopolysaccharide biosynthesis proteins functions (KEGG3), Membrane and intracellular structural molecules functions (KEGG3), Cell motility and secretion functions (KEGG3), Penicillin and cephalosporin biosynthesis functions (KEGG3), Pores ion channels functions (KEGG3), D-Alanine metabolism functions (KEGG3), Geraniol degradation functions (KEGG3), Lipoic acid metabolism functions (KEGG3), Nitrogen metabolism functions (KEGG3), Amino acid metabolism functions (KEGG3), Taurine and hypotaurine metabolism functions (KEGG3), Ribosome Biogenesis functions (KEGG3), Peroxisome functions (KEGG3), Thiamine metabolism functions (KEGG3), Biosynthesis and biodegradation of secondary metabolites functions (KEGG3), Aminoacyl-tRNA biosynthesis functions (KEGG3), Plant-pathogen interaction functions (KEGG3), Cellular antigensv (KEGG3), Type II diabetes mellitus functions (KEGG3), Energy metabolism functions (KEGG3), Citrate cycle functions (TCA cycle) (KEGG3), Cytoskeleton proteins functions (KEGG3), Glycosphingolipid biosynthesis—globo series functions (KEGG3), Photosynthesis functions (KEGG3), Other glycan degradation functions (KEGG3), Drug metabolism—cytochrome P450 functions (KEGG3), Inorganic ion transport and metabolism functions (KEGG3), Photosynthesis proteins functions (KEGG3), Peptidoglycan biosynthesis functions (KEGG3), Protein folding and associated processing functions (KEGG3), Biotin metabolism functions (KEGG3), Aminobenzoate degradation functions (KEGG3), Metabolism of xenobiotics by cytochrome P450 functions (KEGG3), Phosphatidylinositol signaling system functions (KEGG3), Retinol metabolism functions (KEGG3), Nicotinate and nicotinamide metabolism functions (KEGG3), Polycyclic aromatic hydrocarbon degradation functions (KEGG3), and/or other suitable function-related aspects.

Determining a diet-related characterization of a user can include characterizing a user with the at least one of two diet sets (i.e., low carbohydrate diets vs omnivorous & raw meat diets) based upon one or more of the above microbiome features and/or other suitable features described herein, such as in an additional or alternative manner to typical methods of diagnosis or characterization. However, features used in the diet characterization process can include any other suitable features (e.g., features useful for diagnostics), and performing the characterization process for the at least one of two diet sets (i.e. low carbohydrate diets vs omnivorous & raw meat diets) can be performed in any suitable manner.

3.3.C Characterization Process: Low Carbohydrate Diets Vs Vegetarian and Vegan Diets.

In another variation, Block S130 can include performing a diet condition characterization process (e.g., determining and/or applying a diet characterization model; etc.) for one or more users, in relation to at least one of two diet sets: low carbohydrate diets vs vegetarian and vegan diets. In an example, a characterization process (e.g., of Block S130; based upon statistical analyses and/or other suitable approaches described herein; etc.) can identify a set of microbiome features (e.g., microbiome composition features, microbiome function features, etc.) with correlations (e.g., positive correlations, negative correlations, correlations of greatest magnitude, etc.) with at least one of the above diet conditions. In another example, performing a diet condition characterization process can facilitate identifications of one or more health-supporting measures operable to have a positive effect or maintaining effect for subjects with at least one of the above diets (e.g., based upon a random forest predictor algorithm trained with a training dataset derived from a subset of the population of subjects, and validated with a validation dataset derived from a subset of the population of subjects). In particular, at least one of the above dietary conditions can be a lifestyle behavior chosen by the subject, characterized by limited ingestion of some foods or ingestion of some foods only (e.g., no red meat diet, vegetable-only diet, no dietary restriction, etc.) or otherwise associated with a particular dietary regimen (e.g., Vegan diet, Vegetarian diet, Omnivorous diet, etc.) that the subject incorporates as a dietary habit for at least a set time of period that the subject incorporates. The dietary condition can also be associated also with physiological changes that have an effect on the individuals health or health goals (i.e: loss of weight, improvement of concentration, etc.), wherein physiological changes can be associated with an improvement in the health state of a subject that can be measured by medical history (i.e: medical interview), laboratory analysis (i.e: blood sample test, biopsy, etc.), physical measurements (i.e: body mass index, percent body fat, etc.), exercise achievements and any other suitable manner or medical equipment-associated assessment that measures differences in body components levels, metabolic factors, and health conditions (e.g., within a period of time).

Performing the characterization process of the at least one of two diet sets (i.e., low carbohydrate diets vs vegetarian and vegan diets) can be based on microbiome features (e.g., microbiome composition features) associated with (e.g., derived from, informative of, correlated with, etc.) one or more (e.g. in any suitable combination) of the following taxons: *Odoribacter splanchnicus* (species), *Alistipes putredinis* (species), *Flavonifractor plautii* (species), *Phascolarctobacterium faecium* (species), *Bifidobacterium longum* (species), *Parabacteroides distasonis* (species), *Blautia luti* (species), *Sutterella wadsworthensis* (species), *Bacteroides vulgatus* (species), *Bacteroides finegoldii* (species), *Blautia wexlereae* (species), *Blautia obeum* (species), *Bifidobacterium* (genus), *Odoribacter* (genus), *Bilophila* (genus), *Phascolarctobacterium* (genus), *Roseburia* (genus), *Parabacteroides* (genus), *Moryella* (genus), *Intestinimonas* (genus), *Butyricimonas* (genus), *Alistipes* (genus), *Oscillospira* (genus), *Sarcina* (genus), *Flavonifractor* (genus), *Veillonella* (genus), *Clostridium* (genus), *Faecalibacterium* (genus), *Anaerostipes* (genus), *Bacteroides* (genus), *Parasutterella* (genus), Bifidobacteriaceae (family), Desulfovibrionaceae (family), Porphyromonadaceae (family), Sutterellaceae (family), Acidaminococcaceae (family), Rikenellaceae (family), Bacteroidaceae (family), Ruminococcaceae (family), Oscillospiraceae (family), Lactobacillaceae (family), Bifidobacteriales (order), Desulfovibrionales (order), Burkholderiales (order), Clostridiales (order), Bacteroidales (order), Pasteurellales (order), Verrucomicrobiales (order), Selenomonadales (order), Deltaproteobacteria (class), Betaproteobacteria (class), Clostridia (class), Bacteroidia (class), Verrucomicrobiae (class), Negativicutes (class), Proteobacteria (phylum), Firmicutes (phylum), Bacteroidetes (phylum), and Verrucomicrobia (phylum).

Additionally or alternatively, performing the characterization process of the at least one of two diet sets (i.e., low carbohydrate diets vs vegetarian and vegan diets) can be based on microbiome features (e.g., microbiome function features) associated with one or more of (e.g., such as in relation to a corresponding sample site): Transport and Catabolism (KEGG2), Metabolism (KEGG2), Excretory System (KEGG2), Neurodegenerative Diseases (KEGG2), Cancers (KEGG2), Endocrine System (KEGG2), Cellular Processes and Signaling (KEGG2), Glycan Biosynthesis and Metabolism (KEGG2), Phosphatidylinositol signaling system (KEGG3), Amyotrophic lateral sclerosis (ALS) (KEGG3), Huntington's disease (KEGG3), D-Alanine metabolism (KEGG3), Other transporters (KEGG3), Glycosaminoglycan degradation (KEGG3), Glycosphingolipid biosynthesis—ganglio series (KEGG3), Lipoic acid metabolism (KEGG3), Lipopolysaccharide biosynthesis (KEGG3), Amino acid metabolism (KEGG3), Lipopolysaccharide biosynthesis proteins (KEGG3), Glycosphingolipid biosynthesis—globo series (KEGG3), Lysosome (KEGG3), Bisphenol degradation (KEGG3), Penicillin and cephalosporin biosynthesis (KEGG3), Ribosome Biogenesis (KEGG3), Cell motility and secretion (KEGG3), Proximal tubule bicarbonate reclamation (KEGG3), Phenylalanine metabolism (KEGG3), Peroxisome (KEGG3), Pantothenate and CoA biosynthesis (KEGG3), Biotin metabolism (KEGG3), Sphingolipid metabolism (KEGG3), Electron transfer carriers (KEGG3), Other glycan degradation (KEGG3), Membrane and intracellular structural molecules (KEGG3), Ubiquitin system (KEGG3), Inorganic ion transport and metabolism (KEGG3), Phosphonate and phosphinate metabolism (KEGG3), Thiamine metabolism (KEGG3), Toluene degradation (KEGG3), Renal cell carcinoma (KEGG3), Nitrogen metabolism (KEGG3), Photosynthesis (KEGG3), Photosynthesis proteins (KEGG3), Pentose and glucuronate interconversions (KEGG3), Drug metabolism—cytochrome P450 (KEGG3), Adipocytokine signaling pathway (KEGG3), PPAR signaling pathway (KEGG3), Cysteine and methionine metabolism (KEGG3), Aminoacyl-tRNA biosynthesis (KEGG3), Pathways in cancer (KEGG3), Type II diabetes mellitus (KEGG3), Cellular antigens (KEGG3), Pores ion channels (KEGG3), Amino acid related enzymes (KEGG3), Protein processing in endoplasmic reticulum (KEGG3), Metabolism of xenobiotics by cytochrome P450 (KEGG3), Linoleic acid metabolism (KEGG3), and/or other suitable function-related aspects.

Determining a diet-related characterization of a user can include characterizing a user with the at least one of two diet sets (i.e., low carbohydrate diets vs vegetarian and vegan diets) based upon one or more of the above microbiome features and/or other suitable features described herein, such as in an additional or alternative manner to typical methods of diagnosis or characterization. However, features used in the diet characterization process can include any other suitable features (e.g., features useful for diagnostics), and performing the characterization process for the at least one of two diet sets (i.e. low carbohydrate diets vs vegetarian and vegan diets) can be performed in any suitable manner.

3.3.D Characterization Process: Gluten-Free and Dairy-Free Diets Vs Omnivorous Diets.

In another variation, Block S130 can include performing a diet condition characterization process (e.g., determining and/or applying a diet characterization model; etc.) for one or more users, in relation to at least one of two diet sets: gluten-free and dairy-free diets vs omnivorous diets. In an example, a characterization process (e.g., of Block S130; based upon statistical analyses and/or other suitable approaches described herein; etc.) can identify a set of microbiome features (e.g., microbiome composition features, microbiome function features, etc.) with correlations (e.g., positive correlations, negative correlations, correlations of greatest magnitude, etc.) with at least one of the above diet conditions. In another example, performing a diet condition characterization process can facilitate identifications of one or more health-supporting measures operable to have a positive effect or maintaining effect for subjects with at least one of the above diets (e.g., based upon a random forest predictor algorithm trained with a training dataset derived from a subset of the population of subjects, and validated with a validation dataset derived from a subset of the population of subjects). In particular, at least one of the above dietary conditions can be a lifestyle behavior chosen by the subject, characterized by limited ingestion of some foods or ingestion of some foods only (e.g., no red meat diet, vegetable-only diet, no dietary restriction, etc.) or otherwise associated with a particular dietary regimen (e.g., Vega diet, Vegetaria diet, Omnivorous diet, etc.) that the subject incorporates as a dietary habit for at least a set time of period that the subject incorporates. The dietary condition can also be associated also with physiological changes that have an effect on the individuals health or health goals (i.e: loss of weight, improvement of concentration, etc.), wherein physiological changes can be associated with an improvement in the health state of a subject that can be measured by medical history (i.e: medical interview), laboratory analysis (i.e: blood sample test, biopsy, etc.), physical measurements (i.e: body mass index, percent body fat, etc.), exercise achievements and any other suitable manner or medical equipment-associated assessment that measures differences in body components levels, metabolic factors, and health conditions (e.g., within a period of time).

Performing the characterization process of the at least one of two diet sets (i.e., gluten-free and dairy-free diets vs omnivorous diets) can be based on microbiome features (e.g., microbiome composition features) associated with (e.g., derived from, informative of, correlated with, etc.) one or more (e.g. in any suitable combination) of the following taxons: *Collinsella aerofaciens* (species), *Blautia luti* (species), *Bifidobacterium longum* (species), *Alistipes putredinis* (species), *Faecalibacterium prausnitzii* (species), *Flavonifractor plautii* (species), *Streptococcus thermophilus* (species), *Bacteroides vulgatus* (species), *Subdoligranulum variabile* (species), *Parabacteroides distasonis* (species), *Barnesiella intestinihominis* (species), *Roseburia hominis* (species), *Bacteroides thetaiotaomicron* (species), *Odoribacter splanchnicus* (species), *Bacteroides caccae* (species), *Parabacteroides merdae* (species), *Roseburia inulinivorans* (species), *Bacteroides nordii* (species), *Blautia faecis* (species), *Erysipelatoclostridium ramosum* (species), *Bacteroides fragilis* (species), *Blautia wexlereae* (species), *Blautia obeum* (species), *Bifidobacterium* (genus), *Moryella* (genus), *Dorea* (genus), *Collinsella* (genus), *Lachnospira* (genus), *Oscillospira* (genus), *Subdoligranulum* (genus), *Streptococcus* (genus), *Sutterella* (genus), *Pseudobutyrivibrio* (genus), *Intestinimonas* (genus), *Clostridium* (genus), *Dialister* (genus), *Lactobacillus* (genus), *Phascolarctobacterium* (genus), *Bacteroides* (genus), *Faecalibacterium* (genus), *Marvinbryantia* (genus), *Hespellia* (genus), *Roseburia* (genus), *Acetitomaculum* (genus), *Intestinibacter* (genus), *Finegoldia*_150022 (genus), Bifidobacteriaceae (family), Coriobacteriaceae (family), Streptococcaceae (family), Veillonellaceae (family), Prevotellaceae (family), Ruminococcaceae (family), Acidaminococcaceae (family), Enterobacteriaceae (family), Bacteroidaceae (family), Lactobacillaceae (family), Desulfovibrionaceae (family), Clostridiales Family XI. Incertae Sedis (family), Peptostreptococcaceae (family), Erysipelotrichaceae (family), Bifidobacteriales (order), Selenomonadales (order), Coriobacteriales (order), Enterobacteriales (order), Desulfovibrionales (order), Bacteroidales (order), Erysipelotrichales (order), Lactobacillales (order), Actinobacteria (class), Negativicutes (class), Deltaproteobacteria (class), Bacteroidia (class), Gammaproteobacteria (class), Erysipelotrichia (class), Bacilli (class), Betaproteobacteria (class), Actinobacteria (phylum), Bacteroidetes (phylum), Firmicutes (phylum), and Euryarchaeota (phylum).

Additionally or alternatively, performing the characterization process of the at least one of two diet sets (i.e., gluten-free and dairy-free diets vs omnivorous diets) can be based on microbiome features (e.g., microbiome function features) associated with one or more of (e.g., such as in relation to a corresponding sample site): Metabolism (KEGG2), Carbohydrate Metabolism (KEGG2), Enzyme Families (KEGG2), Translation (KEGG2), Genetic Information Processing (KEGG2), Environmental Adaptation (KEGG2), Immune System Diseases (KEGG2), Lipid Metabolism (KEGG2), Transport and Catabolism (KEGG2), Energy Metabolism (KEGG2), Xenobiotics Biodegradation and Metabolism (KEGG2), Replication and Repair (KEGG2), Nucleotide Metabolism (KEGG2), Signaling Molecules and Interaction (KEGG2), Neurodegenerative Diseases (KEGG2), Cell Motility (KEGG2), Poorly Characterized (KEGG2), Metabolism of Other Amino Acids (KEGG2), Glycan Biosynthesis and Metabolism (KEGG2), Cellular Processes and Signaling (KEGG2), Nervous System (KEGG2), ABC transporters (KEGG3), Alanine, aspartate and glutamate metabolism (KEGG3), Amino acid metabolism (KEGG3), Amino acid related enzymes (KEGG3), Amino sugar and nucleotide sugar metabolism (KEGG3), Aminoacyl-tRNA biosynthesis (KEGG3), Aminobenzoate degradation (KEGG3), Bacterial chemotaxis (KEGG3), Base excision repair (KEGG3), Benzoate degradation (KEGG3), Biosynthesis and biodegradation of secondary metabolites (KEGG3), Butanoate metabolism (KEGG3), Carbohydrate digestion and absorption (KEGG3), Carbohydrate metabolism (KEGG3), Carbon fixation in photosynthetic organisms (KEGG3), Carbon fixation pathways in prokaryotes (KEGG3), Cellular antigens (KEGG3), Chromosome (KEGG3), Citrate cycle (TCA cycle) (KEGG3), Cysteine and methionine metabolism (KEGG3), Cytoskeleton proteins (KEGG3), D-Alanine metabolism (KEGG3), DNA repair and recombination proteins (KEGG3), DNA replication (KEGG3), DNA replication proteins (KEGG3), Energy metabolism (KEGG3), Epithelial cell signaling in *Helicobacter pylori* infection (KEGG3), Ethylbenzene degradation (KEGG3), Fatty acid biosynthesis (KEGG3), Fatty acid metabolism (KEGG3), Fructose and mannose metabolism (KEGG3), Galactose metabolism (KEGG3), General function prediction only (KEGG3), Geraniol degradation (KEGG3), Glutamatergic synapse (KEGG3), Glutathione metabolism (KEGG3), Glycerophospholipid metabolism (KEGG3), Glycosphingolipid biosynthesis—globo series (KEGG3), Glyoxylate and dicarboxylate metabolism (KEGG3), Histidine metabolism (KEGG3), Homologous recombination (KEGG3), Huntington's disease (KEGG3), Inositol phosphate metabolism (KEGG3), Ion channels (KEGG3), Limonene and pinene degradation (KEGG3), Lipid biosynthesis proteins (KEGG3), Lipid metabolism (KEGG3), Lipoic acid metabolism (KEGG3), Lipopolysaccharide biosynthesis proteins (KEGG3), Lysine biosynthesis (KEGG3), Lysine degradation (KEGG3), MAPK signaling pathway—yeast (KEGG3), Membrane and intracellular structural molecules (KEGG3), Mismatch repair (KEGG3), Naphthalene degradation (KEGG3), Nicotinate and nicotinamide metabolism (KEGG3), Nitrogen metabolism (KEGG3), Nucleotide excision repair (KEGG3), Nucleotide metabolism (KEGG3), Other glycan degradation (KEGG3), Other ion-coupled transporters (KEGG3), Other transporters (KEGG3), Others (KEGG3), Oxidative phosphorylation (KEGG3), Penicillin and cephalosporin biosynthesis (KEGG3), Pentose and glucuronate interconversions (KEGG3), Pentose phosphate pathway (KEGG3), Peptidases (KEGG3), Peptidoglycan biosynthesis (KEGG3), Peroxisome (KEGG3), Phosphonate and phosphinate metabolism (KEGG3), Photosynthesis (KEGG3), Plant-pathogen interaction (KEGG3), Polycyclic aromatic hydrocarbon degradation (KEGG3), Polyketide sugar unit biosynthesis (KEGG3), Pores ion channels (KEGG3), Primary immunodeficiency (KEGG3), Propanoate metabolism (KEGG3), Protein export (KEGG3), Protein kinases (KEGG3), Purine metabolism (KEGG3), Pyrimidine metabolism (KEGG3), Pyruvate metabolism (KEGG3), RNA polymerase (KEGG3), RNA transport (KEGG3), Replication, recombination and repair proteins (KEGG3), Restriction enzyme (KEGG3), Riboflavin metabolism (KEGG3), Ribosome (KEGG3), Ribosome Biogenesis (KEGG3), Ribosome biogenesis in eukaryotes (KEGG3), Secretion system (KEGG3), Selenocompound metabolism (KEGG3), Sphingolipid metabolism (KEGG3), Streptomycin biosynthesis (KEGG3), Sulfur metabolism (KEGG3), Taurine and hypotaurine metabolism (KEGG3), Terpenoid backbone biosynthesis (KEGG3), Tetracycline biosynthesis (KEGG3), Thiamine metabolism (KEGG3), Transcription factors (KEGG3), Transcription machinery (KEGG3), Translation factors (KEGG3), Translation proteins (KEGG3), Tryptophan metabolism (KEGG3), Tuberculosis (KEGG3), Type I diabetes mellitus (KEGG3), Type II diabetes mellitus (KEGG3), Valine, leucine and isoleucine degradation (KEGG3), beta-Alanine metabolism (KEGG3), and/or any other suitable functional feature.

Determining a diet-related characterization of a user can include characterizing a user with the at least one of two diet sets (i.e., gluten-free and dairy-free diets vs omnivorous diets) based upon one or more of the above microbiome features and/or other suitable features described herein, such as in an additional or alternative manner to typical methods of diagnosis or characterization. However, features used in the diet characterization process can include any other suitable features (e.g., features useful for diagnostics), and performing the characterization process for the at least one of two diet sets (i.e. gluten-free and dairy-free diets vs omnivorous diets) can be performed in any suitable manner.

3.3.E Characterization Process: Gluten-Free and Dairy-Free Diets Vs Vegetarian Diets.

In another variation, Block S130 can include performing a diet condition characterization process (e.g., determining and/or applying a diet characterization model; etc.) for one or more users, in relation to at least one of two diet sets: gluten-free and dairy-free diets vs vegetarian diets. In an example, a characterization process (e.g., of Block S130; based upon statistical analyses and/or other suitable approaches described herein; etc.) can identify a set of microbiome features (e.g., microbiome composition features, microbiome function features, etc.) with correlations (e.g., positive correlations, negative correlations, correlations of greatest magnitude, etc.) with at least one of the above diet conditions. In another example, performing a diet condition characterization process can facilitate identifications of one or more health-supporting measures operable to have a positive effect or maintaining effect for subjects with at least one of the above diets (e.g., based upon a random forest predictor algorithm trained with a training dataset derived from a subset of the population of subjects, and validated with a validation dataset derived from a subset of the population of subjects). In particular, at least one of the above dietary conditions can be a lifestyle behavior chosen by the subject, characterized by limited ingestion of some foods or ingestion of some foods only (e.g., no red meat diet, vegetable-only diet, no dietary restriction, etc.) or otherwise associated with a particular dietary regimen (e.g., Vegan diet, Vegetarian diet, Omnivorous diet, etc.) that the subject incorporates as a dietary habit for at least a set time of period that the subject incorporates. The dietary condition can also be associated also with physiological changes that have an effect on the individuals health or health goals (i.e: loss of weight, improvement of concentration, etc.), wherein physiological changes can be associated with an improvement in the health state of a subject that can be measured by medical history (i.e: medical interview), laboratory analysis (i.e: blood sample test, biopsy, etc.), physical measurements (i.e: body mass index, percent body fat, etc.), exercise achievements and any other suitable manner or medical equipment-associated assessment that measures differences in body components levels, metabolic factors, and health conditions (e.g., within a period of time).

Performing the characterization process of the at least one of two diet sets (i.e., gluten-free and dairy-free diets vs vegetarian diets) can be based on microbiome features (e.g., microbiome composition features) associated with (e.g., derived from, informative of, correlated with, etc.) one or more (e.g. in any suitable combination) of the following taxons: *Flavonifractor plautii* (species), *Bifidobacterium longum* (species), *Parabacteroides distasonis* (species), *Blautia luti* (species), *Bacteroides vulgatus* (species), *Adlercreutzia equolifaciens* (species), *Odoribacter splanchnicus* (species), *Dialister propionicifaciens* (species), *Streptococcus thermophilus* (species), *Collinsella aerofaciens* (species), *Blautia wexlereae* (species), *Blautia obeum* (species), *Bifidobacterium* (genus), *Moryella* (genus), *Intestinimonas* (genus), *Oscillospira* (genus), *Dialister* (genus), *Odoribacter* (genus), *Bilophila* (genus), *Bacteroides* (genus), *Parabacteroides* (genus), *Faecalibacterium* (genus), *Parasutterella* (genus), *Adlercreutzia* (genus), *Streptococcus* (genus), *Butyricimonas* (genus), *Hespellia* (genus), *Clostridium* (genus), *Alistipes* (genus), Bifidobacteriaceae (family), Veillonellaceae (family), Oscillospiraceae (family), Porphyromonadaceae (family), Streptococcaceae (family), Bacteroidaceae (family), Clostridiales Family XIII. Incertae Sedis (family), Desulfovibrionaceae (family), Ruminococcaceae (family), Sutterellaceae (family), Lactobacillaceae (family), Rikenellaceae (family), Bifidobacteriales (order), Desulfovibrionales (order), Bacteroidales (order), Burkholderiales (order), Clostridiales (order), Selenomonadales (order), Actinobacteria (class), Deltaproteobacteria (class), Bacteroidia (class), Clostridia (class), Betaproteobacteria (class), Negativicutes (class), Actinobacteria (phylum), Bacteroidetes (phylum), Firmicutes (phylum), and Proteobacteria (phylum).

Additionally or alternatively, performing the characterization process of the at least one of two diet sets (i.e., gluten-free and dairy-free diets vs vegetarian diets) can be based on microbiome features (e.g., microbiome function features) associated with one or more of (e.g., such as in relation to a corresponding sample site): Metabolism (KEGG2), Carbohydrate Metabolism (KEGG2), Translation (KEGG2), Genetic Information Processing (KEGG2), Transport and Catabolism (KEGG2), Neurodegenerative Diseases (KEGG2), Lipid Metabolism (KEGG2), Xenobiotics Biodegradation and Metabolism (KEGG2), Nervous System (KEGG2), Endocrine System (KEGG2), Energy Metabolism (KEGG2), Amino acid metabolism (KEGG3), Amino acid related enzymes (KEGG3), Aminoacyl-tRNA biosynthesis (KEGG3), Aminobenzoate degradation (KEGG3), Amyotrophic lateral sclerosis (ALS) (KEGG3), Ascorbate and aldarate metabolism (KEGG3), Biosynthesis and biodegradation of secondary metabolites (KEGG3), Bisphenol degradation (KEGG3), Butanoate metabolism (KEGG3), Carbohydrate metabolism (KEGG3), Carbon fixation pathways in prokaryotes (KEGG3), Cellular antigens (KEGG3), Chromosome (KEGG3), Citrate cycle (TCA cycle) (KEGG3), Cysteine and methionine metabolism (KEGG3), D-Alanine metabolism (KEGG3), Electron transfer carriers (KEGG3), Energy metabolism (KEGG3), Fructose and mannose metabolism (KEGG3), Geraniol degradation (KEGG3), Glutamatergic synapse (KEGG3), Glycerophospholipid metabolism (KEGG3), Glycosaminoglycan degradation (KEGG3), Glycosphingolipid biosynthesis—ganglio series (KEGG3), Glycosphingolipid biosynthesis—globo series (KEGG3), Glyoxylate and dicarboxylate metabolism (KEGG3), Huntington's disease (KEGG3), Inositol phosphate metabolism (KEGG3), Lipoic acid metabolism (KEGG3), Lipopolysaccharide biosynthesis (KEGG3), Lipopolysaccharide biosynthesis proteins (KEGG3), Lysosome (KEGG3), Membrane and intracellular structural molecules (KEGG3), Naphthalene degradation (KEGG3), Nicotinate and nicotinamide metabolism (KEGG3), Nitrogen metabolism (KEGG3), Other glycan degradation (KEGG3), Other transporters (KEGG3), Others (KEGG3), Oxidative phosphorylation (KEGG3), PPAR signaling pathway (KEGG3), Penicillin and cephalosporin biosynthesis (KEGG3), Pentose and glucuronate interconversions (KEGG3), Peptidoglycan biosynthesis (KEGG3), Peroxisome (KEGG3), Phenylalanine metabolism (KEGG3), Phosphatidylinositol signaling system (KEGG3), Phosphonate and phosphinate metabolism (KEGG3), Photosynthesis (KEGG3), Photosynthesis proteins (KEGG3), Pores ion channels (KEGG3), Protein processing in endoplasmic reticulum (KEGG3), Proximal tubule bicarbonate reclamation (KEGG3), Pyruvate metabolism (KEGG3), RNA polymerase (KEGG3), Replication, recombination and repair proteins (KEGG3), Ribosome (KEGG3), Ribosome Biogenesis (KEGG3), Sphingolipid metabolism (KEGG3), Terpenoid backbone biosynthesis (KEGG3), Thiamine metabolism (KEGG3), Transcription machinery (KEGG3), Translation proteins (KEGG3), Type I diabetes mellitus (KEGG3), Type II diabetes mellitus (KEGG3), and/or any other suitable functional features.

Determining a diet-related characterization of a user can include characterizing a user with the at least one of two diet sets (i.e., gluten-free and dairy-free diets vs vegetarian diets) based upon one or more of the above microbiome features and/or other suitable features described herein, such as in an additional or alternative manner to typical methods of diagnosis or characterization. However, features used in the diet characterization process can include any other suitable features (e.g., features useful for diagnostics), and performing the characterization process for the at least one of two diet sets (i.e. gluten-free and dairy-free diets vs vegetarian diets) can be performed in any suitable manner.

3.3.F Characterization Process: Diabetes-Associated Diet and Behavior.

In another variation, Block S130 can include performing a diet condition characterization process (e.g., determining and/or applying a diet characterization model; etc.) for one or more users, in relation to diabetes-associated diets and behavior (e.g., halal diets associated with diabetes, omnivorous diets associated with diabetes, low-carb diets associated with diabetes, vegetarian diets associated with diabetes, non-dairy diets associated with diabetes, gluten free diets associated with diabetes, vegan diets associated with diabetes, etc.). In an example, a characterization process (e.g., of Block S130; based upon statistical analyses and/or other suitable approaches described herein; etc.) can identify a set of microbiome features (e.g., microbiome composition features, microbiome function features, etc.) with correlations (e.g., positive correlations, negative correlations, correlations of greatest magnitude, etc.) with at least one of the above diet conditions. In another example, performing a diet condition characterization process can facilitate identifications of one or more health-supporting measures operable to have a positive effect or maintaining effect for subjects with at least one of the above diets (e.g., based upon a random forest predictor algorithm trained with a training dataset derived from a subset of the population of subjects, and validated with a validation dataset derived from a subset of the population of subjects). In particular, Diabetes (e.g., type 2 diabetes) in this first variation is a lifelong condition that causes a person's blood sugar level to become too high characterized by the body's inability to produce enough insulin, or the body's cells to not react to insulin, and diagnosed by laboratory analysis (i.e: blood-samples analysis), and wherein subjects with diabetes are subject to diet and/or behavioral changes.

Performing the characterization process of the diabetes-associated diet and behavior can be based on microbiome features (e.g., microbiome composition features) associated with (e.g., derived from, informative of, correlated with, etc.) one or more (e.g. in any suitable combination) of the following taxons: *Blautia* sp. YHC-4 (species), *Flavonifractor plautii* (species), *Faecalibacterium prausnitzii* (species), *Parabacteroides distasonis* (species), *Blautia luti* (species), *Blautia wexlerae* (species), *Blautia obeum* (species), *Bacteroides uniformis* (species), *Bacteroides finegoldii* (species), *Bacteroides fragilis* (species), *Bacteroides vulgatus* (species), *Subdoligranulum variabile* (species), *Kluyvera* (genus), *Bilophila* (genus), *Moryella* (genus), *Faecalibacterium* (genus), *Subdoligranulum* (genus), *Bacteroides* (genus), *Roseburia* (genus), *Enterobacter* (genus), *Eggerthella* (genus), *Parabacteroides* (genus), *Intestinibacter* (genus), *Anaerotruncus* (genus), *Marvinbryantia* (genus), *Erysipelatoclostridium* (genus), *Dorea* (genus), *Sarcina* (genus), *Akkermansia* (genus), *Anaerostipes* (genus), *Megasphaera* (genus), *Lachnospira* (genus), Enterobacteriaceae (family), Ruminococcaceae (family), Desulfovibrionaceae (family), Bacteroidaceae (family), Lactobacillaceae (family), Porphyromonadaceae (family), Oscillospiraceae (family), Peptostreptococcaceae (family), Verrucomicrobiaceae (family), Enterobacteriales (order), Clostridiales (order), Bacteroidales (order), Desulfovibrionales (order), Verrucomicrobiales (order), Erysipelotrichales (order), Selenomonadales (order), Gammaproteobacteria (class), Clostridia (class), Bacteroidia (class), Deltaproteobacteria (class), Verrucomicrobiae (class), Erysipelotrichia (class), Negativicutes (class), Firmicutes (phylum), Bacteroidetes (phylum) and Proteobacteria (phylum) and Verrucomicrobia (phylum).

Additionally or alternatively, performing the characterization process of the diabetes-associated diet and behavior can be based on taxons associated with one or more sample sites (e.g., gut, nose, skin, genital, mouth, etc.): Acidobacteria (phylum), Actinobacteria (phylum), Bacteroidetes (phylum), Basidiomycota (phylum), *Candidatus* Saccharibacteria (phylum), Chloroflexi (phylum), Cyanobacteria (phylum), *Deinococcus-Thermus* (phylum), Euryarchaeota (phylum), Fibrobacteres (phylum), Firmicutes (phylum), Fusobacteria (phylum), Gemmatimonadetes (phylum), Lentisphaerae (phylum), Planctomycetes (phylum), Proteobacteria (phylum), Spirochaetes (phylum), Streptophyta (phylum), Synergistetes (phylum), Tenericutes (phylum), Verrucomicrobia (phylum), Acidobacteriia (class), Actinobacteria (class), Alphaproteobacteria (class), Anaerolineae (class), Bacilli (class), Bacteroidia (class), Betaproteobacteria (class), Clostridia (class), Cytophagia (class), Deinococci (class), Deltaproteobacteria (class), Epsilonproteobacteria (class), Erysipelotrichia (class), Exobasidiomycetes (class), Fibrobacteria (class), Flavobacteriia (class), Fusobacteriia (class), Gammaproteobacteria (class), Gemmatimonadetes (class), Lentisphaeria (class), Methanobacteria (class), Methanomicrobia (class), Mollicutes (class), Negativicutes (class), Opitutae (class), Planctomycetia (class), Spartobacteria (class), Sphingobacteriia (class), Spirochaetia (class), Synergistia (class), Thermomicrobia (class), Verrucomicrobiae (class), Acidimicrobiales (order), Actinomycetales (order), Aeromonadales (order), Anaerolineales (order), Anaeroplasmatales (order), Bacillales (order), Bacteroidales (order), Bifidobacteriales (order), Burkholderiales (order), Campylobacterales (order), Cardiobacteriales (order), Caulobacterales (order), Clostridiales (order), Coriobacteriales (order), Cytophagales (order), Deinococcales (order), Desulfovibrionales (order), Enterobacteriales (order), Erysipelotrichales (order), Fibrobacterales (order), Flavobacteriales (order), Fusobacterales (order), Gemmatimonadales (order), Hydrogenophilales (order), Lactobacillales (order), Malasseziales (order), Methanobacteriales (order), Mycoplasmatales (order), Myxococcales (order), Neisseriales (order), Oceanospirillales (order), Pasteurellales (order), Planctomycetales (order), Pleurocapsales (order), Pseudomonadales (order), Puniceicoccales (order), Rhizobiales (order), Rhodobacterales (order), Rhodocyclales (order), Rhodospirillales (order), Selenomonadales (order), Solanales (order), Solirubrobacterales (order), Sphingobacteriales (order), Sphingomonadales (order), Spirochaetales (order), Synergistales (order), Thermales (order), Thermoanaerobacterales (order), Verrucomicrobiales (order), Xanthomonadales (order), Acetobacteraceae (family), Acidaminococcaceae (family), Actinomycetaceae (family), Aerococcaceae (family), Aeromonadaceae (family), Alcaligenaceae (family), Anaerolineaceae (family), Anaeroplasmataceae (family), Aurantimonadaceae (family), Bacillaceae (family), Bacteroidaceae (family), Beijerinckiaceae (family), Bifidobacteriaceae (family), Bradyrhizobiaceae (family), Brevibacteriaceae (family), Brucellaceae (family), Burkholderiaceae (family), Caldicoprobacteraceae (family), Campylobacteraceae (family), Cardiobacteriaceae (family), Carnobacteriaceae (family), Catabacteriaceae (family), Caulobacteraceae (family), Cellulomonadaceae (family), Christensenellaceae (family), Clostridiaceae (family), Clostridiales Family XI. Incertae Sedis (family), Clostridiales Family XIII. Incertae Sedis (family), Comamonadaceae (family), Coriobacteriaceae (family), Corynebacteriaceae (family), Cytophagaceae (family), Deinococcaceae (family), Dermabacteraceae (family), Dermacoccaceae (family), Desulfovibrionaceae (family), Dietziaceae (family), Enterobacteriaceae (family), Enterococcaceae (family), Erysipelotrichaceae (family), Erythrobacteraceae (family), Eubacteriaceae (family), Fibrobacteraceae (family), Flavobacteriaceae (family), Fusobacteriaceae (family), Geodermatophilaceae (family), Halomonadaceae (family), Hydrogenophilaceae (family), Hyphomicrobiaceae (family), Iamiaceae (family), Intrasporangiaceae (family), Lachnospiraceae (family), Lactobacillaceae (family), Leptotrichiaceae (family), Leuconostocaceae (family), Malasseziaceae (family), Methanobacteriaceae (family), Methylobacteriaceae (family), Microbacteriaceae (family), Micrococcaceae (family), Moraxellaceae (family), Mycobacteriaceae (family), Mycoplasmataceae (family), Neisseriaceae (family), Nocardiaceae (family), Nocardioidaceae (family), Oscillospiraceae (family), Oxalobacteraceae (family), Pasteurellaceae (family), Patulibacteraceae (family), Peptococcaceae (family), Peptostreptococcaceae (family), Phyllobacteriaceae (family), Planctomycetaceae (family), Planococcaceae (family), Polyangiaceae (family), Porphyromonadaceae (family), Prevotellaceae (family), Promicromonosporaceae (family), Propionibacteriaceae (family), Pseudomonadaceae (family), Pseudonocardiaceae (family), Rhizobiaceae (family), Rhodobacteraceae (family), Rhodocyclaceae (family), Rhodospirillaceae (family), Rikenellaceae (family), Ruminococcaceae (family), Solanaceae (family), Solirubrobacteraceae (family), Sphingobacteriaceae (family), Sphingomonadaceae (family), Staphylococcaceae (family), Streptococcaceae (family), Streptomycetaceae (family), Succinivibrionaceae (family), Sutterellaceae (family), Synergistaceae (family), Thermaceae (family), Thermoanaerobacteraceae (family), Veillonellaceae (family), Verrucomicrobiaceae (family), Victivallaceae (family), Xanthobacteraceae (family), Xanthomonadaceae (family), *Abiotrophia* (genus), *Acetanaerobacterium* (genus), *Acetitomaculum* (genus), *Achromobacter* (genus), *Acidaminococcus* (genus), *Acidiphilium* (genus), *Acinetobacter* (genus), *Actinobacillus* (genus), *Actinobaculum* (genus), *Actinomyces* (genus), *Adlercreutzia* (genus), *Aerococcus* (genus), *Aeromicrobium* (genus), *Aggregatibacter* (genus), *Akkermansia* (genus), *Albidovulum* (genus), *Alistipes* (genus), *Alkanindiges* (genus), *Allisonella* (genus), *Alloiococcus* (genus), *Alloprevotella* (genus), *Alloscardovia* (genus), *Altererythrobacter* (genus), *Alysiella* (genus), *Amaricoccus* (genus), *Aminobacter* (genus), *Anaerobacter* (genus), *Anaerococcus* (genus), *Anaerofilum* (genus), *Anaerofustis* (genus), *Anaeroglobus* (genus), *Anaeroplasma* (genus), *Anaerosporobacter* (genus), *Anaerostipes* (genus), *Anaerotruncus* (genus), *Anaerovorax* (genus), *Aquabacterium* (genus), *Aquipuribacter* (genus), *Arcanobacterium* (genus), *Arthrobacter* (genus), *Asaccharospora* (genus), *Asteroleplasma* (genus), *Atopobium* (genus), *Aureimonas* (genus), *Bacillus* (genus), *Bacteroides* (genus), *Barnesiella* (genus), *Bergeyella* (genus), *Bifidobacterium* (genus), *Bilophila* (genus), *Blastocatella* (genus), *Blastococcus* (genus), *Blautia* (genus), *Bosea* (genus), *Brachybacterium* (genus), *Bradyrhizobium* (genus), *Brevibacterium* (genus), *Brevundimonas* (genus), *Brooklawnia* (genus), *Burkholderia* (genus), *Butyricicoccus* (genus), *Butyricimonas* (genus), *Butyrivibrio* (genus), *Caldicopro-*

*bacter* (genus), *Campylobacter* (genus), *Candidatus Methanomethylophilus* (genus), *Candidatus Saccharimonas* (genus), *Candidatus Soleaferrea* (genus), *Candidatus Stoquefichus* (genus), *Capnocytophaga* (genus), *Cardiobacterium* (genus), *Catabacter* (genus), *Catenibacterium* (genus), *Catonella* (genus), *Caulobacter* (genus), *Cellulomonas* (genus), *Centipeda* (genus), *Chitinophaga* (genus), *Christensenella* (genus), *Chryseobacterium* (genus), *Chthoniobacter* (genus), *Citrobacter* (genus), *Cloacibacillus* (genus), *Cloacibacterium* (genus), *Clostridium* (genus), *Cobetia* (genus), *Collinsella* (genus), *Comamonas* (genus), *Coprobacillus* (genus), *Coprobacter* (genus), *Corynebacterium* (genus), *Cronobacter* (genus), *Curtobacterium* (genus), *Defluviimonas* (genus), *Deinococcus* (genus), *Delftia* (genus), *Dermabacter* (genus), *Desulfovibrio* (genus), *Devosia* (genus), *Dialister* (genus), *Dielma* (genus), *Dietzia* (genus), *Dolosigranulum* (genus), *Dorea* (genus), *Eggerthella* (genus), *Eikenella* (genus), *Eisenbergiella* (genus), *Enterobacter* (genus), *Enterococcus* (genus), *Enterorhabdus* (genus), *Epulopiscium* (genus), *Eremococcus* (genus), *Erysipelatoclostridium* (genus), *Eubacterium* (genus), *Facklamia* (genus), *Faecalibacterium* (genus), *Fastidiosipila* (genus), *Ferruginibacter* (genus), *Fibrobacter* (genus), *Filifactor* (genus), *Finegoldia* (genus), *Flavobacterium* (genus), *Flavonifractor* (genus), *Frigoribacterium* (genus), *Fusicatenibacter* (genus), *Fusobacterium* (genus), *Gallicola* (genus), *Gardnerella* (genus), *Gelria* (genus), *Gemella* (genus), *Geobacillus* (genus), *Globicatella* (genus), *Gordonibacter* (genus), *Granulicatella* (genus), *Haematobacter* (genus), *Haemophilus* (genus), *Hafnia* (genus), *Helcococcus* (genus), *Herbaspirillum* (genus), *Herbiconiux* (genus), *Hespellia* (genus), *Holdemania* (genus), *Howardella* (genus), *Hydrogenoanaerobacterium* (genus), *Hydrogenophilus* (genus), *Hymenobacter* (genus), *Iamia* (genus), *Intestinibacter* (genus), *Intestinimonas* (genus), *Janibacter* (genus), *Jatrophihabitans* (genus), *Johnsonella* (genus), *Jonquetella* (genus), *Kingella* (genus), *Klebsiella* (genus), *Kluyvera* (genus), *Knoellia* (genus), *Kocuria* (genus), *Kytococcus* (genus), *Lachnoanaerobaculum* (genus), *Lachnospira* (genus), *Lactobacillus* (genus), *Lactococcus* (genus), *Lactonifactor* (genus), *Lautropia* (genus), *Leptotrichia* (genus), *Leuconostoc* (genus), *Luteimonas* (genus), *Luteolibacter* (genus), *Lysinibacillus* (genus), *Lysobacter* (genus), *Malassezia* (genus), *Mannheimia* (genus), *Marvinbryantia* (genus), *Megamonas* (genus), *Megasphaera* (genus), *Meiothermus* (genus), *Methanobrevibacter* (genus), *Methanomassiliicoccus* (genus), *Methanosphaera* (genus), *Methylobacterium* (genus), *Microbacterium* (genus), *Micrococcus* (genus), *Microvirga* (genus), *Mitsuokella* (genus), *Mobiluncus* (genus), *Modestobacter* (genus), *Mogibacterium* (genus), *Moraxella* (genus), *Morganella* (genus), *Moryella* (genus), *Mucilaginibacter* (genus), *Murdochiella* (genus), *Mycobacterium* (genus), *Mycoplasma* (genus), *Negativicoccus* (genus), *Neisseria* (genus), *Nocardioides* (genus), *Novosphingobium* (genus), *Ochrobactrum* (genus), *Odoribacter* (genus), *Oligella* (genus), *Olsenella* (genus), *Oribacterium* (genus), *Oscillibacter* (genus), *Oscillospira* (genus), *Pantoea* (genus), *Papillibacter* (genus), *Parabacteroides* (genus), *Paraprevotella* (genus), *Parasporobacterium* (genus), *Parasutterella* (genus), *Parvibacter* (genus), *Parvimonas* (genus), *Pasteurella* (genus), *Patulibacter* (genus), *Paucibacter* (genus), *Pedobacter* (genus), *Pelomonas* (genus), *Peptoclostridium* (genus), *Peptococcus* (genus), *Peptoniphilus* (genus), *Peptostreptococcus* (genus), *Phascolarctobacterium* (genus), *Phyllobacterium* (genus), *Planomicrobium* (genus), *Polaromonas* (genus), *Porphyromonas* (genus), *Prevotella* (genus), *Propionibacterium* (genus), *Propionimicrobium* (genus), *Proteiniclasticum* (genus), *Proteus* (genus), *Pseudobutyrivibrio* (genus), *Pseudoclavibacter* (genus), *Pseudoflavonifractor* (genus), *Pseudolabrys* (genus), *Pseudomonas* (genus), *Pseudorhodoferax* (genus), *Pseudoxanthomonas* (genus), *Psychrobacter* (genus), *Pyramidobacter* (genus), *Rahnella* (genus), *Ralstonia* (genus), *Raoultella* (genus), *Rathayibacter* (genus), *Rhizobium* (genus), *Rhodobacter* (genus), *Rhodococcus* (genus), *Rhodopseudomonas* (genus), *Rikenella* (genus), *Robinsoniella* (genus), *Romboutsia* (genus), *Roseburia* (genus), *Roseomonas* (genus), *Rothia* (genus), *Rubellimicrobium* (genus), *Salinibacterium* (genus), *Sarcina* (genus), *Scardovia* (genus), *Segetibacter* (genus), *Selenomonas* (genus), *Senegalimassilia* (genus), *Shinella* (genus), *Shuttleworthia* (genus), *Skermanella* (genus), *Slackia* (genus), *Sneathia* (genus), *Solobacterium* (genus), *Sorangium* (genus), *Sphingobacterium* (genus), *Sphingobium* (genus), *Sphingomonas* (genus), *Spirosoma* (genus), *Sporobacter* (genus), *Staphylococcus* (genus), *Stenotrophomonas* (genus), *Stomatobaculum* (genus), *Streptobacillus* (genus), *Streptococcus* (genus), *Streptomyces* (genus), *Subdoligranulum* (genus), *Succiniclasticum* (genus), *Succinivibrio* (genus), *Sutterella* (genus), *Synergistes* (genus), *Syntrophococcus* (genus), *Taibaiella* (genus), *Tannerella* (genus), *Terrisporobacter* (genus), *Tessaracoccus* (genus), *Thalassospira* (genus), *Thermomonas* (genus), *Thermus* (genus), *Trichococcus* (genus), *Trueperella* (genus), *Turicella* (genus), *Turicibacter* (genus), *Ureaplasma* (genus), *Vagococcus* (genus), *Varibaculum* (genus), *Variovorax* (genus), *Veillonella* (genus), *Victivallis* (genus), *Weissella* (genus), *Xanthomonas* (genus), *Abiotrophia defectiva* (species), *Achromobacter xylosoxidans* (species), *Acidaminococcus fermentans* (species), *Acidaminococcus intestini* (species), *Acidaminococcus* sp. D21 (species), *Acinetobacter* sp. 423D (species), *Acinetobacter* sp. 511B (species), *Acinetobacter* sp. 8A12N5 (species), *Acinetobacter* sp. C-S-PDA7 (species), *Acinetobacter* sp. RE 51 (species), *Acinetobacter* sp. STE (species), *Acinetobacter* sp. WB22-23 (species), *Actinobacillus porcinus* (species), *Actinobaculum massiliense* (species), *Actinobaculum schaalii* (species), *Actinobaculum urinale* (species), *Actinomyces dentalis* (species), *Actinomyces europaeus* (species), *Actinomyces* genomosp. C1 (species), *Actinomyces gerencseriae* (species), *Actinomyces graevenitzii* (species), *Actinomyces massiliensis* (species), *Actinomyces neuii* (species), *Actinomyces odontolyticus* (species), *Actinomyces radingae* (species), *Actinomyces* sp. (species), *Actinomyces* sp. ICM47 (species), *Actinomyces* sp. ICM54 (species), *Actinomyces* sp. oral strain B19SC (species), *Actinomyces* sp. oral strain Hal-1065 (species), *Actinomyces* sp. oral taxon 170 (species), *Actinomyces* sp. oral taxon 175 (species), *Actinomyces* sp. oral taxon 178 (species), *Actinomyces* sp. oral taxon 448 (species), *Actinomyces* sp. S6-Spd3 (species), *Actinomyces* sp. S9 PR-21 (species), *Actinomyces* sp. ZSY-1 (species), *Adlercreutzia equolifaciens* (species), *Aerococcus christensenii* (species), *Aerococcus sanguinicola* (species), *Aerococcus* sp. B43(2010) (species), *Aerococcus urinae* (species), *Aeromicrobium* sp. PDD-24b-9 (species), *Aggregatibacter aphrophilus* (species), *Aggregatibacter segnis* (species), *Akkermansia muciniphila* (species), *Albidovulum inexpectatum* (species), *Alistipes finegoldii* (species), *Alistipes indistinctus* (species), *Alistipes massiliensis* (species), *Alistipes putredinis* (species), *Alistipes shahii* (species), *Alistipes* sp. 627 (species), *Alistipes* sp. EBA6-25c12 (species), *Alistipes* sp. HGB5 (species), *Alistipes* sp. NML05A004 (species), *Alistipes* sp. RMA 9912 (species), *Alkanindiges illinoisensis* (species), *Allisonella histaminiformans* (species), *Alloiococcus otitis* (species),

*Alloprevotella rava* (species), *Alloprevotella tannerae* (species), *Alloscardovia omnicolens* (species), *Anaerococcus hydrogenalis* (species), *Anaerococcus lactolyticus* (species), *Anaerococcus murdochii* (species), *Anaerococcus octavius* (species), *Anaerococcus prevotii* (species), *Anaerococcus* sp. 8404299 (species), *Anaerococcus* sp. 8405254 (species), *Anaerococcus* sp. 9401487 (species), *Anaerococcus* sp. 9402080 (species), *Anaerococcus* sp. PH9 (species), *Anaerococcus* sp. S9 PR-5 (species), *Anaerococcus tetradius* (species), *Anaerococcus vaginalis* (species), *Anaerofustis stercorihominis* (species), *Anaeroglobus geminatus* (species), *Anaerosporobacter mobilis* (species), *Anaerostipes butyraticus* (species), *Anaerostipes caccae* (species), *Anaerostipes hadrus* (species), *Anaerostipes* sp. 3_2_56FAA (species), *Anaerostipes* sp. 494a (species), *Anaerostipes* sp. 5_1_63FAA (species), *Anaerotruncus colihominis* (species), *Anaerotruncus* sp. NML 070203 (species), *Anaerovibrio* sp. 765 (species), *Aquabacterium* sp. Aqua2 (species), *Aquipuribacter hungaricus* (species), *Arcanobacterium* sp. NML 06501 (species), *Arthrobacter albus* (species), *Arthrobacter* sp. LM27(2011) (species), *Asaccharospora irregularis* (species), *Atopobium parvulum* (species), *Atopobium rimae* (species), *Atopobium* sp. DMCT15023 (species), *Atopobium* sp. FO209 (species), *Atopobium* sp. HHRM1715 (species), *Atopobium* sp. ICM57 (species), *Atopobium vaginae* (species), *Aureimonas altamirensis* (species), *Bacillus niacini* (species), *Bacillus pocheonensis* (species), *Bacillus* sp. DHT-33 (species), *Bacteroides acidifaciens* (species), *Bacteroides barnesiae* (species), *Bacteroides caccae* (species), *Bacteroides clarus* (species), *Bacteroides coprocola* (species), *Bacteroides dorei* (species), *Bacteroides eggerthii* (species), *Bacteroides faecis* (species), *Bacteroides finegoldii* (species), *Bacteroides fluxus* (species), *Bacteroides fragilis* (species), *Bacteroides gallinarum* (species), *Bacteroides intestinalis* (species), *Bacteroides massiliensis* (species), *Bacteroides nordii* (species), *Bacteroides ovatus* (species), *Bacteroides plebeius* (species), *Bacteroides salyersiae* (species), *Bacteroides* sp. 2_2_4 (species), *Bacteroides* sp. 35AE37 (species), *Bacteroides* sp. AR20 (species), *Bacteroides* sp. AR29 (species), *Bacteroides* sp. CB57 (species), *Bacteroides* sp. D-2 (species), *Bacteroides* sp. D20 (species), *Bacteroides* sp. D22 (species), *Bacteroides* sp. DJF_B097 (species), *Bacteroides* sp. EBA5-17 (species), *Bacteroides* sp. J1511 (species), *Bacteroides* sp. S-17 (species), *Bacteroides* sp. SLC1-38 (species), *Bacteroides* sp. TP-5 (species), *Bacteroides* sp. XB12B (species), *Bacteroides* sp. XB44A (species), *Bacteroides stercorirosoris* (species), *Bacteroides stercoris* (species), *Bacteroides thetaiotaomicron* (species), *Bacteroides uniformis* (species), *Bacteroides vulgatus* (species), *Barnesiella intestinihominis* (species), *Barnesiella* sp. 177 (species), *Bergeyella* sp. AF14 (species), *Bifidobacterium adolescentis* (species), *Bifidobacterium animalis* (species), *Bifidobacterium bifidum* (species), *Bifidobacterium choerinum* (species), *Bifidobacterium gallicum* (species), *Bifidobacterium kashiwanohense* (species), *Bifidobacterium longum* (species), *Bifidobacterium merycicum* (species), *Bifidobacterium pseudocatenulatum* (species), *Bifidobacterium pullorum* (species), *Bifidobacterium* sp. (species), *Bifidobacterium* sp. 120 (species), *Bifidobacterium* sp. MSX5B (species), *Bifidobacterium stercoris* (species), *Bilophila* sp. 4_1_30 (species), *Bilophila wadsworthia* (species), *Blautia faecis* (species), *Blautia glucerasea* (species), *Blautia hansenii* (species), *Blautia hydrogenotrophica* (species), *Blautia luti* (species), *Blautia producta* (species), *Blautia* sp. Ser5 (species), *Blautia* sp. Ser8 (species), *Blautia* sp. YHC-4 (species), *Blautia stercoris* (species), *Blautia wexlerae* (species), *Brachybacterium* sp. NIO-27 (species), *Bradyrhizobium* sp. 68A4SAPT (species), *Brevibacterium massiliense* (species), *Brevibacterium paucivorans* (species), *Brevibacterium pityocampae* (species), *Brevundimonas faecalis* (species), *Brevundimonas* sp. Ci19 (species), *Brevundimonas* sp. FXJ8.080 (species), *Burkholderia* sp. S32 (species), *Butyricicoccus pullicaecorum* (species), *Butyricimonas* sp. 214-4 (species), *Butyricimonas* sp. JCM 18676 (species), *Butyricimonas* sp. JCM 18677 (species), *Butyricimonas synergistica* (species), *Butyricimonas virosa* (species), *Butyrivibrio crossotus* (species), *Campylobacter concisus* (species), *Campylobacter gracilis* (species), *Campylobacter hominis* (species), *Campylobacter showae* (species), *Campylobacter* sp. 10_1_50 (species), *Campylobacter* sp. FOBRC14 (species), *Campylobacter* sp. FOBRC15 (species), *Campylobacter sputorum* (species), *Campylobacter ureolyticus* (species), *Capnocytophaga granulosa* (species), *Capnocytophaga leadbetteri* (species), *Capnocytophaga* sp. AHN9576 (species), *Capnocytophaga* sp. AHN9756 (species), *Capnocytophaga* sp. CM59 (species), *Capnocytophaga* sp. HS5_2W_I24 (species), *Capnocytophaga* sp. oral taxon 329 (species), *Capnocytophaga* sp. oral taxon 335 (species), *Capnocytophaga* sp. oral taxon 336 (species), *Capnocytophaga* sp. oral taxon 338 (species), *Capnocytophaga sputigena* (species), *Cardiobacterium valvarum* (species), *Catenibacterium mitsuokai* (species), *Catonella morbi* (species), *Caulobacter* sp. (species), *Centipeda periodontii* (species), *Christensenella minuta* (species), *Chryseobacterium hominis* (species), *Chryseobacterium* sp. bk_19 (species), *Chryseobacterium* sp. CH9 (species), *Chryseobacterium* sp. TP-S110w-C25 (species), *Citrobacter amalonaticus* (species), *Citrobacter* sp. BW4 (species), *Cloacibacillus evryensis* (species), *Cloacibacillus porcorum* (species), *Cobetia* sp. AP-MSU 3 (species), *Collinsella aerofaciens* (species), *Collinsella intestinalis* (species), *Collinsella* sp. GD3 (species), *Collinsella tanakaei* (species), *Coprobacillus* sp. D6 (species), *Coprobacter fastidiosus* (species), *Corynebacterium argentoratense* (species), *Corynebacterium atypicum* (species), *Corynebacterium canis* (species), *Corynebacterium durum* (species), *Corynebacterium epidermidicanis* (species), *Corynebacterium freiburgense* (species), *Corynebacterium glucuronolyticum* (species), *Corynebacterium mastitidis* (species), *Corynebacterium matruchotii* (species), *Corynebacterium* sp. (species), *Corynebacterium* sp. canine oral taxon 423 (species), *Corynebacterium* sp. NML 97-0186 (species), *Corynebacterium* sp. NML96-0085 (species), *Corynebacterium spheniscorum* (species), *Corynebacterium ulcerans* (species), *Corynebacterium vitaeruminis* (species), *Cronobacter sakazakii* (species), *Delftia* sp. BN-SKY3 (species), *Dermabacter hominis* (species), *Dermabacter* sp. HFH0086 (species), *Desulfovibrio desulfuricans* (species), *Desulfovibrio piger* (species), *Desulfovibrio* sp. (species), *Desulfovibrio* sp. 6_1_46AFAA (species), *Desulfovibrio* sp. G11 (species), *Dialister invisus* (species), *Dialister micraerophilus* (species), *Dialister pneumosintes* (species), *Dialister propionicifaciens* (species), *Dialister* sp. E2_20 (species), *Dialister* sp. S7MSR5 (species), *Dialister succinatiphilus* (species), *Dielma fastidiosa* (species), *Dietzia* sp. ISA13 (species), *Dolosigranulum pigrum* (species), *Dorea formicigenerans* (species), *Dorea longicatena* (species), *Eggerthella lenta* (species), *Eggerthella sinensis* (species), *Eggerthella* sp. HGA1 (species), *Eisenbergiella tayi* (species), *Enterobacter asburiae* (species), *Enterobacter* sp. BS2-1 (species), *Enterococcus durans* (species), *Enterococcus faecalis* (species), *Enterococcus raffinosus* (species), *Enterococcus* sp. C6I11 (species), *Enterococcus* sp. SI-4 (species), *Eremococ-* cus coleocola (species), Erysipelatoclostridium ramosum (species), Eubacterium callanderi (species), Eubacterium sp. SA11 (species), Facklamia hominis (species), Facklamia languida (species), Facklamia sp. 1440-97 (species), Faecalibacterium prausnitzii (species), Faecalibacterium sp. canine oral taxon 147 (species), Fastidiosipila sanguinis (species), Filifactor alocis (species), Finegoldia magna (species), Finegoldia sp. S8 F7 (species), Finegoldia sp. S9 AA1-5 (species), Flavobacterium ceti (species), Flavonifractor plautii (species), Fretibacterium fastidiosum (species), Fusicatenibacter saccharivorans (species), Fusobacterium equinum (species), Fusobacterium necrogenes (species), Fusobacterium nucleatum (species), Fusobacterium periodonticum (species), Fusobacterium sp. AS2 (species), Fusobacterium sp. CM1 (species), Fusobacterium sp. CM21 (species), Fusobacterium sp. CM22 (species), Fusobacterium sp. CM55 (species), Fusobacterium ulcerans (species), Fusobacterium varium (species), Gardnerella vaginalis (species), Gemella morbillorum (species), Gemella sanguinis (species), Gemella sp. 933-88 (species), Gemella sp. oral strain C24KA (species), Globicatella sulfidifaciens (species), Gordonibacter pamelaeae (species), Granulicatella adiacens (species), Granulicatella elegans (species), Haematobacter massiliensis (species), Haemophilus influenzae (species), Haemophilus parainfluenzae (species), Hafnia alvei (species), Herbaspirillum seropedicae (species), Herbaspirillum sp. YR522 (species), Herbiconiux solani (species), Holdemania filiformis (species), Howardella ureilytica (species), Hydrogenophilus islandicus (species), Hymenobacter sp. R-36553 (species), Intestinimonas butyriciproducens (species), Janibacter sp. M3-5 (species), Johnsonella ignava (species), Jonquetella anthropi (species), Kingella oralis (species), Klebsiella oxytoca (species), Klebsiella sp. B12 (species), Klebsiella sp. SOR89 (species), Kluyvera georgiana (species), Knoellia sp. BA3(2011) (species), Kocuria kristinae (species), Kocuria sp. A-248b (species), Kocuria sp. FXJ6.339 (species), Kocuria sp. M1-36 (species), Kocuria sp. M2T9B2 (species), Kytococcus sp. MC7-1 (species), Lachnoanaerobaculum orale (species), Lachnoanaerobaculum saburreum (species), Lachnoanaerobaculum sp. MSX33 (species), Lachnospira pectinoschiza (species), Lactobacillus acidophilus (species), Lactobacillus coleohominis (species), Lactobacillus crispatus (species), Lactobacillus delbrueckii (species), Lactobacillus fornicalis (species), Lactobacillus gasseri (species), Lactobacillus johnsonii (species), Lactobacillus mucosae (species), Lactobacillus paracasei (species), Lactobacillus plantarum (species), Lactobacillus rhamnosus (species), Lactobacillus ruminis (species), Lactobacillus salivarius (species), Lactobacillus sp. 66c (species), Lactobacillus sp. 7_1_47FAA (species), Lactobacillus sp. Akhmrol (species), Lactobacillus sp. BL302 (species), Lactobacillus sp. BL304 (species), Lactobacillus sp. C30An8 (species), Lactobacillus sp. C412 (species), Lactobacillus sp. TAB-22 (species), Lactobacillus sp. TAB-26 (species), Lactobacillus sp. TAB-30 (species), Lactobacillus vaginalis (species), Lactococcus lactis (species), Lactococcus sp. MH5-2 (species), Lactonifactor longoviformis (species), Lautropia sp. TeTO (species), Leptotrichia genomosp. C1 (species), Leptotrichia goodfellowii (species), Leptotrichia hofstadii (species), Leptotrichia hongkongensis (species), Leptotrichia shahii (species), Leptotrichia sp. oral taxon 225 (species), Leptotrichia sp. PG10 (species), Leptotrichia trevisanii (species), Leptotrichia wadei (species), Leuconostoc inhae (species), Leuconostoc mesenteroides (species), Leuconostoc sp. C714 (species), Luteolibacter sp. LX93 (species), Lysobacter sp. Zo-YC6813 (species), Malassezia restricta (species), Mannheimia varigena (species), Megamonas funiformis (species), Megasphaera elsdenii (species), Megasphaera genomosp. C1 (species), Megasphaera sp. BV3C16-1 (species), Megasphaera sp. DNF00912 (species), Megasphaera sp. S6-MB2 (species), Megasphaera sp. UPII 199-6 (species), Meiothermus silvanus (species), Methanobrevibacter smithii (species), Methanosphaera stadtmanae (species), Methylobacterium sp. PDD-23b-14 (species), Methylobacterium sp. RK-2008-1 (species), Micrococcus sp. M12-2-2 (species), Micrococcus sp. WB18-01 (species), Mitsuokella sp. DJF_RR21 (species), Mitsuokella sp. TM-10 (species), Mobiluncus curtisii (species), Mobiluncus mulieris (species), Mogibacterium sp. CM50 (species), Mogibacterium sp. CM96 (species), Moraxella caprae (species), Moraxella catarrhalis (species), Moraxella lincolnii (species), Moraxella sp. BB37 (species), Moraxella sp. WB19-16 (species), Morganella morganii (species), Moryella indoligenes (species), Murdochiella asaccharolytica (species), Murdochiella sp. S9 PR-10 (species), Mycobacterium sp. KNUC297 (species), Mycoplasma falconis (species), Mycoplasma spermatophilum (species), Negativicoccus succinicivorans (species), Neisseria bacilliformis (species), Neisseria elongata (species), Neisseria flavescens (species), Neisseria macacae (species), Neisseria mucosa (species), Neisseria oralis (species), Neisseria shayeganii (species), Neisseria sicca (species), Neisseria sp. SMC-A9199 (species), Nocardioides mesophilus (species), Novosphingobium sediminicola (species), Novosphingobium sp. TrD22 (species), Odoribacter laneus (species), Odoribacter splanchnicus (species), Oligella urethralis (species), Olsenella sp. 1183 (species), Olsenella sp. F0004 (species), Olsenella sp. S9 HS-6 (species), Oribacterium sp. OBRC12 (species), Oribacterium sp. oral taxon 078 (species), Oribacterium sp. oral taxon 108 (species), Oscillospira guilliermondii (species), Pantoea agglomerans (species), Pantoea sp. CWB304 (species), Parabacteroides distasonis (species), Parabacteroides goldsteinii (species), Parabacteroides gordonii (species), Parabacteroides johnsonii (species), Parabacteroides merdae (species), Parabacteroides sp. 157 (species), Parabacteroides sp. D25 (species), Parabacteroides sp. dnLKV8 (species), Paraprevotella clara (species), Paraprevotella xylaniphila (species), Parasporobacterium paucivorans (species), Parasutterella excrementihominis (species), Parvibacter caecicola (species), Parvimonas micra (species), Parvimonas sp. oral taxon 393 (species), Pasteurella pneumotropica (species), Patulibacter minatonensis (species), Pediococcus sp. MFC1 (species), Pedobacter heparinus (species), Pelomonas aquatica (species), Peptoclostridium difficile (species), Peptococcus niger (species), Peptococcus sp. oral taxon 168 (species), Peptoniphilus coxii (species), Peptoniphilus duerdenii (species), Peptoniphilus koenoeneniae (species), Peptoniphilus lacrimalis (species), Peptoniphilus sp. 2002-2300004 (species), Peptoniphilus sp. 2002-38328 (species), Peptoniphilus sp. 7-2 (species), Peptoniphilus sp. DNF00840 (species), Peptoniphilus sp. gpac018A (species), Peptoniphilus sp. gpacl48 (species), Peptoniphilus sp. JCM 8143 (species), Peptoniphilus sp. oral taxon 375 (species), Peptoniphilus sp. oral taxon 836 (species), Peptostreptococcus anaerobius (species), Peptostreptococcus stomatis (species), Phascolarctobacterium faecium (species), Phascolarctobacterium sp. 377 (species), Phascolarctobacterium sp. canine oral taxon 149 (species), Phascolarctobacterium succinatutens (species), Phenylobacterium haematophilum (species), Phyllobacterium sp. T50 (species), Polaromonas aquatica (species), Porphyromonas asaccharolytica (species), *Porphyromonas bennonis* (species), *Porphyromonas catoniae* (species), *Porphyromonas endodontalis* (species), *Porphyromonas gingivalis* (species), *Porphyromonas gulae* (species), *Porphyromonas somerae* (species), *Porphyromonas* sp. 2026 (species), *Porphyromonas uenonis* (species), *Prevotella aurantiaca* (species), *Prevotella bivia* (species), *Prevotella buccalis* (species), *Prevotella disiens* (species), *Prevotella intermedia* (species), *Prevotella maculosa* (species), *Prevotella micans* (species), *Prevotella nanceiensis* (species), *Prevotella nigrescens* (species), *Prevotella oralis* (species), *Prevotella oris* (species), *Prevotella oulorum* (species), *Prevotella pallens* (species), *Prevotella* sp. oral taxon 299 (species), *Prevotella* sp. oral taxon G60 (species), *Prevotella* sp. S4-10 (species), *Prevotella* sp. WAL 2039G (species), *Prevotella timonensis* (species), *Propionibacterium acnes* (species), *Propionibacterium avidum* (species), *Propionibacterium granulosum* (species), *Propionibacterium propionicum* (species), *Propionibacterium* sp. 'Oral Taxon 191' (species), *Propionibacterium* sp. MSP09A (species), *Propionibacterium* sp. V07/12348 (species), *Propionimicrobium lymphophilum* (species), *Proteus mirabilis* (species), *Pseudoclavibacter bifida* (species), *Pseudoclavibacter* sp. Timone (species), *Pseudoflavonifractor capillosus* (species), *Pseudomonas aeruginosa* (species), *Pseudomonas brenneri* (species), *Pseudomonas monteilii* (species), *Pseudomonas* sp. a111-5 (species), *Pseudomonas* sp. GmFRB023 (species), *Pseudomonas* sp. KB23 (species), *Pseudomonas* sp. P3 (species), *Pseudomonas* sp. PDD-31b-4 (species), *Pseudomonas syringae* (species), *Psychrobacter* sp. bio-1 (species), *Pyramidobacter piscolens* (species), *Rahnella* sp. BSP18 (species), *Ralstonia* sp. S2.MAC.005 (species), *Raoultella ornithinolytica* (species), *Rathayibacter* sp. PDD-32b-54 (species), *Rhizobium skierniewicense* (species), *Rhizobium* sp. ICB500 (species), *Rhizobium* sp. PDD-32b-29 (species), *Rhizobium* sp. T45 (species), *Rhodococcus* sp. CO56 (species), *Rhodococcus* sp. MARG10 (species), *Rhodococcus* sp. PDD-31b-7 (species), *Rhodopseudomonas thermotolerans* (species), *Roseburia cecicola* (species), *Roseburia faecis* (species), *Roseburia hominis* (species), *Roseburia intestinalis* (species), *Roseburia inulinivorans* (species), *Roseburia* sp. 11SE39 (species), *Roseburia* sp. 499 (species), *Roseburia* sp. DJF_RR73 (species), *Roseomonas* sp. PDD-31b-6 (species), *Rothia aeria* (species), *Rothia dentocariosa* (species), *Rothia mucilaginosa* (species), *Rothia* sp. CCUG 25688 (species), *Rothia* sp. LH-CAB6 (species), *Salinibacterium* sp. MDT1-9-1 (species), *Sarcina ventriculi* (species), *Scardovia wiggsiae* (species), *Selenomonas* sp. CM52 (species), *Shinella* sp. DR33 (species), *Shuttleworthia* sp. oral taxon G69 (species), *Slackia exigua* (species), *Slackia piriformis* (species), *Slackia* sp. NATIS (species), *Sneathia sanguinegens* (species), *Solobacterium* sp. S4-A19 (species), *Sphingobacterium spiritivorum* (species), *Sphingobium* sp. MH60 (species), *Sphingomonas glacialis* (species), *Sphingomonas* sp. 540 (species), *Sphingomonas* sp. CS81 (species), *Sphingomonas* sp. KOPRI 25661 (species), *Sphingomonas* sp. MM62(2011) (species), *Sphingomonas* sp. PDD-26b-16 (species), *Sphingomonas* sp. TPD18 (species), *Staphylococcus* sp. C-D-MA2 (species), *Staphylococcus* sp. C5116 (species), *Staphylococcus* sp. C9I2 (species), *Staphylococcus* sp. L10 (species), *Stenotrophomonas* sp. C-S-TSA3 (species), *Stenotrophomonas* sp. KITS-1 (species), *Stenotrophomonas* sp. NB3 (species), *Stenotrophomonas* sp. PDD-33b-8 (species), *Stomatobaculum longum* (species), *Streptococcus agalactiae* (species), *Streptococcus equinus* (species), *Streptococcus gordonii* (species), *Streptococcus intermedius* (species), *Streptococcus mitis* (species), *Streptococcus mutans* (species), *Streptococcus parasanguinis* (species), *Streptococcus pasteurianus* (species), *Streptococcus peroris* (species), *Streptococcus* sp. 2011_Oral_MS_A3 (species), *Streptococcus* sp. BS35a (species), *Streptococcus* sp. oral taxon G59 (species), *Streptococcus* sp. oral taxon G63 (species), *Streptococcus* sp. 816-11 (species), *Streptococcus thermophilus* (species), *Subdoligranulum variabile* (species), *Sutterella* sp. 252 (species), *Sutterella* sp. YIT 12072 (species), *Sutterella stercoricanis* (species), *Sutterella wadsworthensis* (species), *Tannerella forsythia* (species), *Tannerella* sp. oral taxon BU063 (species), *Terrisporobacter glycolicus* (species), *Tessaracoccus* sp. IPBSL-7 (species), *Tessaracoccus* sp. SL014B-79A (species), *Trueperella bernardiae* (species), *Turicella otitidis* (species), *Turicibacter sanguinis* (species), *Ureaplasma urealyticum* (species), *Vagococcus* sp. SIX2(2011) (species), *Varibaculum cambriense* (species), *Varibaculum* sp. CCUG 45114 (species), *Variovorax* sp. TA DQ (species), *Veillonella atypica* (species), *Veillonella dispar* (species), *Veillonella montpellierensis* (species), *Veillonella rogosae* (species), *Veillonella* sp. 2011_Oral_VSA C9 (species), *Veillonella* sp. 2011_Oral_VSA_D3 (species), *Veillonella* sp. AS16 (species), *Veillonella* sp. CM60 (species), *Veillonella* sp. FFA-2014 (species), *Veillonella* sp. MSA12 (species), *Veillonella* sp. oral taxon 780 (species), *Victivallis vadensis* (species), *Weissella hellenica* (species), *Xanthomonas gardneri* (species).

Additionally or alternatively, performing the characterization process of the diabetes-associated diet and behavior can be based on microbiome features (e.g., microbiome function features) associated with one or more of (e.g., such as in relation to a corresponding sample site): Carbohydrate transport and metabolism (COG2), Environmental Adaptation (KEGG2), Poorly Characterized (KEGG2), Signaling Molecules and Interaction (KEGG2), Metabolism (KEGG2), Transport and Catabolism (KEGG2), Cell Motility (KEGG2), Glycan Biosynthesis and Metabolism (KEGG2), Cellular Processes and Signaling (KEGG2), Metabolism of Other Amino Acids (KEGG2), Xenobiotics Biodegradation and Metabolism (KEGG2), Translation (KEGG2), Neurodegenerative Diseases (KEGG2), Infectious Diseases (KEGG2), Amino Acid Metabolism (KEGG2), Transcription (KEGG2), Digestive System (KEGG2), Replication and Repair (KEGG2), Protein folding and associated processing (KEGG3), Plant-pathogen interaction (KEGG3), Amino acid metabolism (KEGG3), Nitrogen metabolism (KEGG3), Geraniol degradation (KEGG3), Inorganic ion transport and metabolism (KEGG3), Penicillin and cephalosporin biosynthesis (KEGG3), Pores ion channels (KEGG3), Lipoic acid metabolism (KEGG3), Lipopolysaccharide biosynthesis proteins (KEGG3), Vitamin metabolism (KEGG3), Membrane and intracellular structural molecules (KEGG3), Huntington's disease (KEGG3), Ribosome Biogenesis (KEGG3), Ion channels (KEGG3), Cytoskeleton proteins (KEGG3), Inositol phosphate metabolism (KEGG3), Biotin metabolism (KEGG3), Other ion-coupled transporters (KEGG3), Cellular antigens (KEGG3), Bacterial chemotaxis (KEGG3), Taurine and hypotaurine metabolism (KEGG3), Function unknown (KEGG3), Phosphatidylinositol signaling system (KEGG3), Glutathione metabolism (KEGG3), Chromosome (KEGG3), Glycosphingolipid biosynthesis—ganglio series (KEGG3), Butirosin and neomycin biosynthesis (KEGG3), Polycyclic aromatic hydrocarbon degradation (KEGG3), Glycosaminoglycan degradation (KEGG3), Folate biosynthesis (KEGG3), beta-Alanine metabolism (KEGG3), Aminoacyl-tRNA biosynthesis (KEGG3), Cell motility and secretion (KEGG3), Tuberculosis (KEGG3), Lysosome (KEGG3), Thiamine metabolism (KEGG3), Selenocompound metabolism (KEGG3), Photosynthesis (KEGG3), Photosynthesis proteins (KEGG3), Glycosyltransferases (KEGG3), Citrate cycle (TCA cycle) (KEGG3), Others (KEGG3), Tryptophan metabolism (KEGG3), Oxidative phosphorylation (KEGG3), Nucleotide metabolism (KEGG3), Bacterial toxins (KEGG3), Aminobenzoate degradation (KEGG3), Phenylalanine, tyrosine and tryptophan biosynthesis (KEGG3), Sporulation (KEGG3), Terpenoid backbone biosynthesis (KEGG3), Pantothenate and CoA biosynthesis (KEGG3), Translation proteins (KEGG3), Peptidoglycan biosynthesis (KEGG3), Glycerophospholipid metabolism (KEGG3), Peroxisome (KEGG3), Amino acid related enzymes (KEGG3), RNA transport (KEGG3), Cysteine and methionine metabolism (KEGG3), Lysine biosynthesis (KEGG3), Biosynthesis of ansamycins (KEGG3), Fatty acid metabolism (KEGG3), Drug metabolism—cytochrome P450 (KEGG3), Glycine, serine and threonine metabolism (KEGG3), Ribosome (KEGG3), Homologous recombination (KEGG3), Nicotinate and nicotinamide metabolism (KEGG3), Glyoxylate and dicarboxylate metabolism (KEGG3), Metabolism of xenobiotics by cytochrome P450 (KEGG3), Lysine degradation (KEGG3), Starch and sucrose metabolism (KEGG3), Lipid metabolism (KEGG3), Valine, leucine and isoleucine degradation (KEGG3), Biosynthesis of unsaturated fatty acids (KEGG3), Carbon fixation pathways in prokaryotes (KEGG3), Biosynthesis and biodegradation of secondary metabolites (KEGG3), Insulin signaling pathway (KEGG3), Phosphotransferase system (PTS) (KEGG3), Type II diabetes mellitus (KEGG3), Bacterial secretion system (KEGG3), Ribosome biogenesis in eukaryotes (KEGG3), Glycolysis/Gluconeogenesis (KEGG3), Retinol metabolism (KEGG3), Valine, leucine and isoleucine biosynthesis (KEGG3), Amino sugar and nucleotide sugar metabolism (KEGG3), Pyrimidine metabolism (KEGG3), Mismatch repair (KEGG3), General function prediction only (KEGG3), Propanoate metabolism (KEGG3), Naphthalene degradation (KEGG3), Limonene and pinene degradation (KEGG3), Translation factors (KEGG3), Methane metabolism (KEGG3), Pentose and glucuronate interconversions (KEGG3), Type I diabetes mellitus (KEGG3) and RNA polymerase (KEGG3), and/or any other suitable functional feature.

Determining a diet-related characterization of a user can include characterizing a user with the at least one of the diabetes-associated diet and behavior based upon one or more of the above microbiome features and/or other suitable features described herein, such as in an additional or alternative manner to typical methods of diagnosis or characterization. However, features used in the diet characterization process can include any other suitable features (e.g., features useful for diagnostics), and performing the characterization process for the at least one of the diabetes-associated diet and behavior can be performed in any suitable manner.

3.3.G Characterization Process: Lactose and Fermented Food Tolerant Microorganisms.

In another variation, Block S130 can include performing a diet condition characterization process (e.g., determining and/or applying a diet characterization model; etc.) for one or more users, in relation to dietary conditions that are associated with microorganisms that are tolerant of lactose and/or fermented foods. In an example, a characterization process (e.g., of Block S130; based upon statistical analyses and/or other suitable approaches described herein; etc.) can identify a set of microbiome features (e.g., microbiome composition features, microbiome function features, etc.) with correlations (e.g., positive correlations, negative correlations, correlations of greatest magnitude, etc.) with at least one of the above diet conditions. In another example, performing a diet condition characterization process can facilitate identifications of one or more health-supporting measures operable to have a positive effect or maintaining effect for subjects with at least one of the above diets (e.g., based upon a random forest predictor algorithm trained with a training dataset derived from a subset of the population of subjects, and validated with a validation dataset derived from a subset of the population of subjects). In particular, tolerance for lactose and fermented food in this variation is associated with an ability to process lactose and components present in other fermented foods that are lacking in subjects diagnosed as lactose intolerant, or with specific conditions characterized by processing of those type of foods generate an abnormal state for the subject or other associated health issues (e.g., bloating) after the ingestion of a specific kind of food (e.g., milk, yogurt, cheese or its derivatives, etc.) within the diet; diagnosis for inability condition to process lactose or fermented food, could be associated with medical record (e.g., medical interview), laboratory exams (e.g., genetic test), and any other suitable test.

Performing the characterization process of the dietary conditions that are associated with microorganisms that are tolerant of lactose and/or fermented foods can be based on microbiome features (e.g., microbiome composition features) associated with (e.g., derived from, informative of, correlated with, etc.) one or more (e.g. in any suitable combination) of the following taxons: *Flavonifractor plautii* (species), *Bifidobacterium longum* (species), *Parabacteroides distasonis* (species), *Blautia luti* (species), *Bacteroides vulgatus* (species), *Adlercreutzia equolifaciens* (species), *Odoribacter splanchnicus* (species), *Dialister propionicifaciens* (species), *Streptococcus thermophilus* (species), *Collinsella aerofaciens* (species), *Blautia wexlereae* (species), *Blautia obeum* (species), *Bifidobacterium* (genus), *Moryella* (genus), *Intestinimonas* (genus), *Oscillospira* (genus), *Dialister* (genus), *Odoribacter* (genus), *Bilophila* (genus), *Bacteroides* (genus), *Parabacteroides* (genus), *Faecalibacterium* (genus), *Parasutterella* (genus), *Adlercreutzia* (genus), *Streptococcus* (genus), *Butyricimonas* (genus), *Hespellia* (genus), *Clostridium* (genus), *Alistipes* (genus), Bifidobacteriaceae (family), Veillonellaceae (family), Oscillospiraceae (family), Porphyromonadaceae (family), Streptococcaceae (family), Bacteroidaceae (family), Clostridiales Family XIII. Incertae Sedis (family), Desulfovibrionaceae (family), Ruminococcaceae (family), Sutterellaceae (family), Lactobacillaceae (family), Rikenellaceae (family), Bifidobacteriales (order), Desulfovibrionales (order), Bacteroidales (order), Burkholderiales (order), Clostridiales (order), Selenomonadales (order), Actinobacteria (class), Deltaproteobacteria (class), Bacteroidia (class), Clostridia (class), Betaproteobacteria (class), Negativicutes (class) Actinobacteria (phylum), Bacteroidetes (phylum), Firmicutes (phylum), and Proteobacteria (phylum).

Additionally or alternatively, microbiome features can be associated with one or more of the following taxons in relation to a sample site: Acidobacteria (phylum; e.g., gut site), Acidobacteria (phylum; e.g., nose site), Acidobacteria (phylum; e.g., skin site), Actinobacteria (phylum; e.g., genital site), Actinobacteria (phylum; e.g., gut site), Bacteroidetes (phylum; e.g., gut site), Bacteroidetes (phylum; e.g., nose site), Bacteroidetes (phylum; e.g., skin site), *Candidatus* Saccharibacteria (phylum; e.g., mouth site), *Candidatus*

Saccharibacteria (phylum; e.g., nose site), Cyanobacteria (phylum; e.g., gut site), Cyanobacteria (phylum; e.g., nose site), Cyanobacteria (phylum; e.g., skin site), Euryarchaeota (phylum; e.g., gut site), Euryarchaeota (phylum; e.g., nose site), Fibrobacteres (phylum; e.g., gut site), Firmicutes (phylum; e.g., gut site), Fusobacteria (phylum; e.g., gut site), Fusobacteria (phylum; e.g., mouth site), Fusobacteria (phylum; e.g., nose site), Fusobacteria (phylum; e.g., skin site), Lentisphaerae (phylum; e.g., gut site), Proteobacteria (phylum; e.g., gut site), Proteobacteria (phylum; e.g., skin site), Spirochaetes (phylum; e.g., gut site), Spirochaetes (phylum; e.g., nose site), Streptophyta (phylum; e.g., mouth site), Synergistetes (phylum; e.g., gut site), Synergistetes (phylum; e.g., skin site), Tenericutes (phylum; e.g., gut site), Tenericutes (phylum; e.g., skin site), Verrucomicrobia (phylum; e.g., gut site), Acidobacteriia (class; e.g., gut site), Acidobacteriia (class; e.g., nose site), Acidobacteriia (class; e.g., skin site), Actinobacteria (class; e.g., genital site), Actinobacteria (class; e.g., gut site), Alphaproteobacteria (class; e.g., gut site), Alphaproteobacteria (class; e.g., mouth site), Alphaproteobacteria (class; e.g., nose site), Alphaproteobacteria (class; e.g., skin site), Bacilli (class; e.g., gut site), Bacteroidia (class; e.g., gut site), Bacteroidia (class; e.g., nose site), Bacteroidia (class; e.g., skin site), Betaproteobacteria (class; e.g., gut site), Betaproteobacteria (class; e.g., mouth site), Betaproteobacteria (class; e.g., nose site), Betaproteobacteria (class; e.g., skin site), Clostridia (class; e.g., genital site), Clostridia (class; e.g., gut site), Clostridia (class; e.g., nose site), Cytophagia (class; e.g., nose site), Deltaproteobacteria (class; e.g., gut site), Deltaproteobacteria (class; e.g., skin site), Epsilonproteobacteria (class; e.g., gut site), Epsilonproteobacteria (class; e.g., mouth site), Epsilonproteobacteria (class; e.g., nose site), Erysipelotrichia (class; e.g., gut site), Erysipelotrichia (class; e.g., mouth site), Erysipelotrichia (class; e.g., nose site), Erysipelotrichia (class; e.g., skin site), Fibrobacteria (class; e.g., gut site), Flavobacteriia (class; e.g., gut site), Flavobacteriia (class; e.g., nose site), Flavobacteriia (class; e.g., skin site), Fusobacteriia (class; e.g., gut site), Fusobacteriia (class; e.g., mouth site), Fusobacteriia (class; e.g., nose site), Fusobacteriia (class; e.g., skin site), Gammaproteobacteria (class; e.g., gut site), Gammaproteobacteria (class; e.g., skin site), Lentisphaeria (class; e.g., gut site), Methanobacteria (class; e.g., nose site), Methanomicrobia (class; e.g., gut site), Mollicutes (class; e.g., gut site), Negativicutes (class; e.g., gut site), Negativicutes (class; e.g., mouth site), Negativicutes (class; e.g., skin site), Oligosphaeria (class; e.g., gut site), Opitutae (class; e.g., gut site), Sphingobacteriia (class; e.g., gut site), Sphingobacteriia (class; e.g., nose site), Spirochaetia (class; e.g., nose site), Synergistia (class; e.g., gut site), Synergistia (class; e.g., skin site), Verrucomicrobiae (class; e.g., gut site), Acholeplasmatales (order; e.g., gut site), Acidobacteriales (order; e.g., gut site), Acidobacteriales (order; e.g., nose site), Actinomycetales (order; e.g., gut site), Aeromonadales (order; e.g., gut site), Aeromonadales (order; e.g., skin site), Anaeroplasmatales (order; e.g., gut site), Bacillales (order; e.g., gut site), Bacteroidales (order; e.g., gut site), Bacteroidales (order; e.g., nose site), Bacteroidales (order; e.g., skin site), Bifidobacteriales (order; e.g., gut site), Bifidobacteriales (order; e.g., nose site), Burkholderiales (order; e.g., gut site), Burkholderiales (order; e.g., mouth site), Burkholderiales (order; e.g., nose site), Burkholderiales (order; e.g., skin site), Campylobacterales (order; e.g., gut site), Campylobacterales (order; e.g., mouth site), Campylobacterales (order; e.g., nose site), Cardiobacteriales (order; e.g., mouth site), Caulobacterales (order; e.g., gut site), Caulobacterales (order; e.g., mouth site), Caulobacterales (order; e.g., nose site), Caulobacterales (order; e.g., skin site), Clostridiales (order; e.g., genital site), Clostridiales (order; e.g., gut site), Clostridiales (order; e.g., nose site), Coriobacteriales (order; e.g., gut site), Coriobacteriales (order; e.g., mouth site), Coriobacteriales (order; e.g., skin site), Cytophagales (order; e.g., nose site), Deinococcales (order; e.g., nose site), Deinococcales (order; e.g., skin site), Desulfovibrionales (order; e.g., gut site), Desulfovibrionales (order; e.g., skin site), Enterobacteriales (order; e.g., genital site), Enterobacteriales (order; e.g., gut site), Enterobacteriales (order; e.g., mouth site), Enterobacteriales (order; e.g., nose site), Enterobacteriales (order; e.g., skin site), Erysipelotrichales (order; e.g., gut site), Erysipelotrichales (order; e.g., mouth site), Erysipelotrichales (order; e.g., nose site), Erysipelotrichales (order; e.g., skin site), Fibrobacterales (order; e.g., gut site), Flavobacteriales (order; e.g., gut site), Flavobacteriales (order; e.g., nose site), Flavobacteriales (order; e.g., skin site), Fusobacteriales (order; e.g., gut site), Fusobacteriales (order; e.g., mouth site), Fusobacteriales (order; e.g., nose site), Fusobacteriales (order; e.g., skin site), Lactobacillales (order; e.g., genital site), Lactobacillales (order; e.g., gut site), Methanobacteriales (order; e.g., nose site), Mycoplasmatales (order; e.g., gut site), Neisseriales (order; e.g., gut site), Neisseriales (order; e.g., mouth site), Neisseriales (order; e.g., nose site), Neisseriales (order; e.g., skin site), Oligosphaerales (order; e.g., gut site), Pasteurellales (order; e.g., genital site), Pasteurellales (order; e.g., gut site), Pasteurellales (order; e.g., mouth site), Pasteurellales (order; e.g., nose site), Pasteurellales (order; e.g., skin site), Pseudomonadales (order; e.g., genital site), Pseudomonadales (order; e.g., gut site), Pseudomonadales (order; e.g., mouth site), Pseudomonadales (order; e.g., skin site), Puniceicoccales (order; e.g., gut site), Rhizobiales (order; e.g., gut site), Rhizobiales (order; e.g., mouth site), Rhizobiales (order; e.g., nose site), Rhizobiales (order; e.g., skin site), Rhodobacterales (order; e.g., nose site), Rhodobacterales (order; e.g., skin site), Rhodocyclales (order; e.g., gut site), Rhodospirillales (order; e.g., gut site), Rhodospirillales (order; e.g., nose site), Rhodospirillales (order; e.g., skin site), Selenomonadales (order; e.g., gut site), Selenomonadales (order; e.g., mouth site), Selenomonadales (order; e.g., skin site), Solanales (order; e.g., mouth site), Sphingobacteriales (order; e.g., gut site), Sphingobacteriales (order; e.g., nose site), Sphingomonadales (order; e.g., nose site), Sphingomonadales (order; e.g., skin site), Spirochaetales (order; e.g., gut site), Synergistales (order; e.g., gut site), Synergistales (order; e.g., skin site), Thermales (order; e.g., gut site), Thermoanaerobacterales (order; e.g., gut site), Verrucomicrobiales (order; e.g., gut site), Xanthomonadales (order; e.g., nose site), Acetobacteraceae (family; e.g., nose site), Acidaminococcaceae (family; e.g., gut site), Acidaminococcaceae (family; e.g., skin site), Acidobacteriaceae (family; e.g., gut site), Acidobacteriaceae (family; e.g., nose site), Actinomycetaceae (family; e.g., gut site), Actinomycetaceae (family; e.g., mouth site), Actinomycetaceae (family; e.g., nose site), Aerococcaceae (family; e.g., gut site), Aerococcaceae (family; e.g., nose site), Aerococcaceae (family; e.g., skin site), Aeromonadaceae (family; e.g., skin site), Alcaligenaceae (family; e.g., nose site), Anaeroplasmataceae (family; e.g., gut site), Bacillaceae (family; e.g., gut site), Bacillaceae (family; e.g., mouth site), Bacillaceae (family; e.g., nose site), Bacillaceae (family; e.g., skin site), Bacteroidaceae (family; e.g., genital site), Bacteroidaceae (family; e.g., gut site), Bacteroidaceae (family; e.g., nose site), Bacteroidaceae (family; e.g., skin site), Bartonellaceae (family; e.g., skin site), Bifidobacteriaceae (family; e.g., gut site), Bifidobacteriaceae (family; e.g., nose site), Bradyrhizobiaceae (family; e.g., gut site), Bradyrhizobiaceae (family; e.g., mouth site), Bradyrhizobiaceae (family; e.g., nose site), Bradyrhizobiaceae (family; e.g., skin site), Brevibacteriaceae (family; e.g., gut site), Brevibacteriaceae (family; e.g., nose site), Brevibacteriaceae (family; e.g., skin site), Brucellaceae (family; e.g., nose site), Brucellaceae (family; e.g., skin site), Burkholderiaceae (family; e.g., mouth site), Burkholderiaceae (family; e.g., nose site), Burkholderiaceae (family; e.g., skin site), Caldicoprobacteraceae (family; e.g., gut site), Campylobacteraceae (family; e.g., gut site), Campylobacteraceae (family; e.g., mouth site), Campylobacteraceae (family; e.g., nose site), Cardiobacteriaceae (family; e.g., mouth site), Carnobacteriaceae (family; e.g., gut site), Carnobacteriaceae (family; e.g., mouth site), Carnobacteriaceae (family; e.g., nose site), Carnobacteriaceae (family; e.g., skin site), Caulobacteraceae (family; e.g., gut site), Caulobacteraceae (family; e.g., mouth site), Caulobacteraceae (family; e.g., nose site), Caulobacteraceae (family; e.g., skin site), Christensenellaceae (family; e.g., gut site), Clostridiaceae (family; e.g., gut site), Clostridiaceae (family; e.g., mouth site), Clostridiaceae (family; e.g., nose site), Clostridiaceae (family; e.g., skin site), Clostridiales Family XI. Incertae Sedis (family; e.g., genital site), Clostridiales Family XI. Incertae Sedis (family; e.g., gut site), Clostridiales Family XI. Incertae Sedis (family; e.g., mouth site), Clostridiales Family XI. Incertae Sedis (family; e.g., nose site), Clostridiales Family XIII. Incertae Sedis (family; e.g., gut site), Clostridiales Family XIII. Incertae Sedis (family; e.g., mouth site), Clostridiales Family XIII. Incertae Sedis (family; e.g., skin site), Comamonadaceae (family; e.g., genital site), Comamonadaceae (family; e.g., gut site), Comamonadaceae (family; e.g., mouth site), Comamonadaceae (family; e.g., nose site), Comamonadaceae (family; e.g., skin site), Coriobacteriaceae (family; e.g., gut site), Coriobacteriaceae (family; e.g., mouth site), Coriobacteriaceae (family; e.g., skin site), Corynebacteriaceae (family; e.g., genital site), Corynebacteriaceae (family; e.g., gut site), Corynebacteriaceae (family; e.g., mouth site), Cytophagaceae (family; e.g., gut site), Cytophagaceae (family; e.g., nose site), Deinococcaceae (family; e.g., nose site), Dermabacteraceae (family; e.g., nose site), Dermacoccaceae (family; e.g., skin site), Desulfovibrionaceae (family; e.g., gut site), Desulfovibrionaceae (family; e.g., skin site), Dietziaceae (family; e.g., skin site), Enterobacteriaceae (family; e.g., genital site), Enterobacteriaceae (family; e.g., gut site), Enterobacteriaceae (family; e.g., mouth site), Enterobacteriaceae (family; e.g., nose site), Enterobacteriaceae (family; e.g., skin site), Enterococcaceae (family; e.g., gut site), Enterococcaceae (family; e.g., skin site), Erysipelotrichaceae (family; e.g., gut site), Erysipelotrichaceae (family; e.g., mouth site), Erysipelotrichaceae (family; e.g., nose site), Erysipelotrichaceae (family; e.g., skin site), Fibrobacteraceae (family; e.g., gut site), Flavobacteriaceae (family; e.g., gut site), Flavobacteriaceae (family; e.g., nose site), Flavobacteriaceae (family; e.g., skin site), Fusobacteriaceae (family; e.g., gut site), Fusobacteriaceae (family; e.g., mouth site), Fusobacteriaceae (family; e.g., skin site), Gordoniaceae (family; e.g., nose site), Helicobacteraceae (family; e.g., gut site), Intrasporangiaceae (family; e.g., skin site), Lachnospiraceae (family; e.g., genital site), Lachnospiraceae (family; e.g., gut site), Lachnospiraceae (family; e.g., nose site), Lachnospiraceae (family; e.g., skin site), Lactobacillaceae (family; e.g., genital site), Lactobacillaceae (family; e.g., gut site), Leptotrichiaceae (family; e.g., nose site), Leuconostocaceae (family; e.g., gut site), Methanobacteriaceae (family; e.g., nose site), Methylobacteriaceae (family; e.g., gut site), Methylobacteriaceae (family; e.g., mouth site), Methylobacteriaceae (family; e.g., nose site), Methylobacteriaceae (family; e.g., skin site), Microbacteriaceae (family; e.g., gut site), Microbacteriaceae (family; e.g., skin site), Micrococcaceae (family; e.g., gut site), Micrococcaceae (family; e.g., nose site), Micrococcaceae (family; e.g., skin site), Moraxellaceae (family; e.g., gut site), Moraxellaceae (family; e.g., mouth site), Moraxellaceae (family; e.g., nose site), Moraxellaceae (family; e.g., skin site), Mycobacteriaceae (family; e.g., mouth site), Mycobacteriaceae (family; e.g., nose site), Mycoplasmataceae (family; e.g., gut site), Neisseriaceae (family; e.g., gut site), Neisseriaceae (family; e.g., mouth site), Neisseriaceae (family; e.g., nose site), Neisseriaceae (family; e.g., skin site), Nocardiaceae (family; e.g., nose site), Nocardiaceae (family; e.g., skin site), Nocardioidaceae (family; e.g., nose site), Oscillospiraceae (family; e.g., gut site), Oscillospiraceae (family; e.g., nose site), Oscillospiraceae (family; e.g., skin site), Oxalobacteraceae (family; e.g., gut site), Oxalobacteraceae (family; e.g., nose site), Oxalobacteraceae (family; e.g., skin site), Pasteurellaceae (family; e.g., genital site), Pasteurellaceae (family; e.g., gut site), Pasteurellaceae (family; e.g., mouth site), Pasteurellaceae (family; e.g., nose site), Pasteurellaceae (family; e.g., skin site), Patulibacteraceae (family; e.g., skin site), Peptococcaceae (family; e.g., gut site), Peptostreptococcaceae (family; e.g., gut site), Peptostreptococcaceae (family; e.g., nose site), Peptostreptococcaceae (family; e.g., skin site), Phyllobacteriaceae (family; e.g., nose site), Phyllobacteriaceae (family; e.g., skin site), Planococcaceae (family; e.g., skin site), Porphyromonadaceae (family; e.g., gut site), Porphyromonadaceae (family; e.g., mouth site), Porphyromonadaceae (family; e.g., nose site), Prevotellaceae (family; e.g., gut site), Prevotellaceae (family; e.g., mouth site), Propionibacteriaceae (family; e.g., gut site), Propionibacteriaceae (family; e.g., skin site), Pseudoalteromonadaceae (family; e.g., nose site), Pseudomonadaceae (family; e.g., genital site), Pseudomonadaceae (family; e.g., gut site), Pseudomonadaceae (family; e.g., nose site), Pseudomonadaceae (family; e.g., skin site), Rhizobiaceae (family; e.g., gut site), Rhizobiaceae (family; e.g., nose site), Rhizobiaceae (family; e.g., skin site), Rhodobacteraceae (family; e.g., nose site), Rhodobacteraceae (family; e.g., skin site), Rhodocyclaceae (family; e.g., gut site), Rhodocyclaceae (family; e.g., skin site), Rhodospirillaceae (family; e.g., gut site), Rikenellaceae (family; e.g., gut site), Rikenellaceae (family; e.g., nose site), Rikenellaceae (family; e.g., skin site), Ruminococcaceae (family; e.g., genital site), Ruminococcaceae (family; e.g., gut site), Ruminococcaceae (family; e.g., nose site), Ruminococcaceae (family; e.g., skin site), Sphingomonadaceae (family; e.g., nose site), Sphingomonadaceae (family; e.g., skin site), Staphylococcaceae (family; e.g., nose site), Streptococcaceae (family; e.g., gut site), Streptococcaceae (family; e.g., mouth site), Streptococcaceae (family; e.g., skin site), Sutterellaceae (family; e.g., gut site), Sutterellaceae (family; e.g., nose site), Sutterellaceae (family; e.g., skin site), Synergistaceae (family; e.g., gut site), Synergistaceae (family; e.g., skin site), Thermaceae (family; e.g., gut site), Thermoanaerobacteraceae (family; e.g., gut site), Veillonellaceae (family; e.g., gut site), Veillonellaceae (family; e.g., mouth site), Veillonellaceae (family; e.g., skin site), Verrucomicrobiaceae (family; e.g., gut site), Victivallaceae (family; e.g., gut site), Xanthomonadaceae (family; e.g., nose site), *Abiotrophia* (genus; e.g., nose site), *Acetitomaculum* (genus; e.g., gut site), *Acidaminococcus* (genus; e.g., gut site), *Acidovorax* (genus; e.g., gut site), *Acinetobacter* (genus; e.g., genital site), *Acinetobacter* (genus; e.g., gut site), *Acinetobacter* (genus; e.g., mouth site), *Acinetobacter* (genus; e.g., nose site), *Acinetobacter* (genus; e.g., skin site), *Actinobacillus* (genus; e.g., genital site), *Actinobacillus* (genus; e.g., gut site), *Actinobacillus* (genus; e.g., mouth site), *Actinobacillus* (genus; e.g., skin site), *Actinomyces* (genus; e.g., gut site), *Actinomyces* (genus; e.g., mouth site), *Actinomyces* (genus; e.g., nose site), *Actinomyces* (genus; e.g., skin site), *Adlercreutzia* (genus; e.g., gut site), *Aeromonas* (genus; e.g., skin site), *Aerosphaera* (genus; e.g., gut site), *Aggregatibacter* (genus; e.g., gut site), *Aggregatibacter* (genus; e.g., mouth site), *Aggregatibacter* (genus; e.g., nose site), *Akkermansia* (genus; e.g., gut site), *Alistipes* (genus; e.g., gut site), *Alistipes* (genus; e.g., nose site), *Alistipes* (genus; e.g., skin site), *Allisonella* (genus; e.g., gut site), *Allobaculum* (genus; e.g., gut site), *Alloprevotella* (genus; e.g., gut site), *Alloprevotella* (genus; e.g., mouth site), *Alloprevotella* (genus; e.g., nose site), *Alloscardovia* (genus; e.g., gut site), *Anaerobacillus* (genus; e.g., nose site), *Anaerobacillus* (genus; e.g., skin site), *Anaerobacter* (genus; e.g., gut site), *Anaerococcus* (genus; e.g., gut site), *Anaerococcus* (genus; e.g., mouth site), *Anaerofilum* (genus; e.g., gut site), *Anaeroplasma* (genus; e.g., gut site), *Anaerosporobacter* (genus; e.g., gut site), *Anaerostipes* (genus; e.g., gut site), *Anaerostipes* (genus; e.g., nose site), *Anaerostipes* (genus; e.g., skin site), *Anaerotruncus* (genus; e.g., gut site), *Anaerotruncus* (genus; e.g., nose site), *Anaerotruncus* (genus; e.g., skin site), *Anaerovibrio* (genus; e.g., gut site), *Anaerovorax* (genus; e.g., gut site), *Aquabacterium* (genus; e.g., gut site), *Aquabacterium* (genus; e.g., mouth site), *Aquabacterium* (genus; e.g., skin site), *Arcanobacterium* (genus; e.g., gut site), *Arthrobacter* (genus; e.g., gut site), *Arthrobacter* (genus; e.g., nose site), *Asaccharospora* (genus; e.g., gut site), *Asaccharospora* (genus; e.g., nose site), *Asteroleplasma* (genus; e.g., gut site), *Atopobium* (genus; e.g., gut site), *Atopobium* (genus; e.g., mouth site), *Atopobium* (genus; e.g., nose site), *Bacillus* (genus; e.g., gut site), *Bacillus* (genus; e.g., nose site), *Bacillus* (genus; e.g., skin site), *Bacteroides* (genus; e.g., genital site), *Bacteroides* (genus; e.g., gut site), *Bacteroides* (genus; e.g., nose site), *Bacteroides* (genus; e.g., skin site), *Barnesiella* (genus; e.g., gut site), *Barnesiella* (genus; e.g., skin site), *Bartonella* (genus; e.g., skin site), *Bifidobacterium* (genus; e.g., gut site), *Bifidobacterium* (genus; e.g., nose site), *Bifidobacterium* (genus; e.g., skin site), *Bilophila* (genus; e.g., gut site), *Bilophila* (genus; e.g., skin site), *Blautia* (genus; e.g., genital site), *Blautia* (genus; e.g., gut site), *Blautia* (genus; e.g., nose site), *Blautia* (genus; e.g., skin site), *Bradyrhizobium* (genus; e.g., gut site), *Bradyrhizobium* (genus; e.g., mouth site), *Bradyrhizobium* (genus; e.g., nose site), *Bradyrhizobium* (genus; e.g., skin site), *Brevibacterium* (genus; e.g., gut site), *Brevibacterium* (genus; e.g., nose site), *Brevibacterium* (genus; e.g., skin site), *Brevundimonas* (genus; e.g., gut site), *Brevundimonas* (genus; e.g., mouth site), *Brevundimonas* (genus; e.g., nose site), *Brevundimonas* (genus; e.g., skin site), *Butyricimonas* (genus; e.g., gut site), *Butyricimonas* (genus; e.g., skin site), *Butyrivibrio* (genus; e.g., gut site), *Caldicoprobacter* (genus; e.g., gut site), *Campylobacter* (genus; e.g., gut site), *Campylobacter* (genus; e.g., mouth site), *Campylobacter* (genus; e.g., nose site), *Candidatus Saccharimonas* (genus; e.g., mouth site), *Candidatus Soleaferrea* (genus; e.g., gut site), *Candidatus Stoquefichus* (genus; e.g., gut site), *Capnocytophaga* (genus; e.g., nose site), *Cardiobacterium* (genus; e.g., mouth site), *Catenibacterium* (genus; e.g., nose site), *Caulobacter* (genus; e.g., nose site), *Cellulosilyticum* (genus; e.g., gut site), *Centipeda* (genus; e.g., mouth site), *Christensenella* (genus; e.g., gut site), *Chryseobacterium* (genus; e.g., nose site), *Chryseobacterium* (genus; e.g., skin site), *Citrobacter* (genus; e.g., gut site), *Citrobacter* (genus; e.g., skin site), *Cloacibacillus* (genus; e.g., gut site), *Clostridium* (genus; e.g., gut site), *Clostridium* (genus; e.g., nose site), *Clostridium* (genus; e.g., skin site), *Collinsella* (genus; e.g., gut site), *Collinsella* (genus; e.g., nose site), *Collinsella* (genus; e.g., skin site), *Coprobacillus* (genus; e.g., gut site), *Coprobacter* (genus; e.g., gut site), *Corynebacterium* (genus; e.g., genital site), *Corynebacterium* (genus; e.g., gut site), *Corynebacterium* (genus; e.g., mouth site), *Cronobacter* (genus; e.g., gut site), *Cryobacterium* (genus; e.g., genital site), *Deinococcus* (genus; e.g., nose site), *Delftia* (genus; e.g., gut site), *Delftia* (genus; e.g., mouth site), *Delftia* (genus; e.g., nose site), *Delftia* (genus; e.g., skin site), *Dermabacter* (genus; e.g., gut site), *Dermabacter* (genus; e.g., nose site), *Dermacoccus* (genus; e.g., skin site), *Desulfovibrio* (genus; e.g., gut site), *Dialister* (genus; e.g., gut site), *Dialister* (genus; e.g., nose site), *Dielma* (genus; e.g., gut site), *Dietzia* (genus; e.g., skin site), *Dorea* (genus; e.g., gut site), *Dorea* (genus; e.g., nose site), *Dorea* (genus; e.g., skin site), *Eggerthella* (genus; e.g., gut site), *Eisenbergiella* (genus; e.g., gut site), *Enterobacter* (genus; e.g., genital site), *Enterobacter* (genus; e.g., gut site), *Enterobacter* (genus; e.g., skin site), *Enterococcus* (genus; e.g., gut site), *Enterococcus* (genus; e.g., skin site), *Enterorhabdus* (genus; e.g., gut site), *Eremococcus* (genus; e.g., gut site), *Erysipelatoclostridium* (genus; e.g., gut site), *Erysipelatoclostridium* (genus; e.g., skin site), *Facklamia* (genus; e.g., gut site), *Faecalibacterium* (genus; e.g., gut site), *Faecalibacterium* (genus; e.g., nose site), *Faecalibacterium* (genus; e.g., skin site), *Fastidiosipila* (genus; e.g., gut site), *Fibrobacter* (genus; e.g., gut site), *Finegoldia* (genus; e.g., genital site), *Finegoldia* (genus; e.g., gut site), *Finegoldia* (genus; e.g., mouth site), *Flavobacterium* (genus; e.g., genital site), *Flavobacterium* (genus; e.g., gut site), *Flavobacterium* (genus; e.g., mouth site), *Flavobacterium* (genus; e.g., nose site), *Flavobacterium* (genus; e.g., skin site), *Flavonifractor* (genus; e.g., gut site), *Flavonifractor* (genus; e.g., nose site), *Flavonifractor* (genus; e.g., skin site), *Fretibacterium* (genus; e.g., gut site), *Fusicatenibacter* (genus; e.g., gut site), *Fusicatenibacter* (genus; e.g., nose site), *Fusicatenibacter* (genus; e.g., skin site), *Fusobacterium* (genus; e.g., gut site), *Fusobacterium* (genus; e.g., mouth site), *Fusobacterium* (genus; e.g., skin site), *Gallicola* (genus; e.g., gut site), *Gardnerella* (genus; e.g., gut site), *Gardnerella* (genus; e.g., skin site), *Gelria* (genus; e.g., gut site), *Gemella* (genus; e.g., gut site), *Gemella* (genus; e.g., mouth site), *Gemella* (genus; e.g., nose site), *Gemella* (genus; e.g., skin site), *Gordonia* (genus; e.g., nose site), *Gordonibacter* (genus; e.g., gut site), *Granulicatella* (genus; e.g., gut site), *Granulicatella* (genus; e.g., nose site), *Granulicatella* (genus; e.g., skin site), *Haemophilus* (genus; e.g., gut site), *Haemophilus* (genus; e.g., mouth site), *Haemophilus* (genus; e.g., nose site), *Haemophilus* (genus; e.g., skin site), *Halomonas* (genus; e.g., nose site), *Helicobacter* (genus; e.g., gut site), *Herbaspirillum* (genus; e.g., gut site), *Herbaspirillum* (genus; e.g., nose site), *Herbaspirillum* (genus; e.g., skin site), *Hespellia* (genus; e.g., gut site), *Holdemania* (genus; e.g., gut site), *Howardella* (genus; e.g., gut site), *Hydrogenoanaerobacterium* (genus; e.g., gut site), *Hymenobacter* (genus; e.g., nose site), *Intestinibacter* (genus; e.g., gut site), *Intestinibacter* (genus; e.g., nose site), *Intestinibacter* (genus; e.g., skin site), *Intestinimonas* (genus; e.g., gut site), *Intestinimonas* (genus; e.g., skin site), *Janibacter* (genus; e.g., skin site), *Johnsonella* (genus; e.g., mouth site), *Klebsiella* (genus; e.g., gut site), *Kluyvera* (genus; e.g., genital site), *Kluyvera* (genus; e.g., gut site),

*Kluyvera* (genus; e.g., nose site), *Lachnospira* (genus; e.g., gut site), *Lachnospira* (genus; e.g., nose site), *Lachnospira* (genus; e.g., skin site), *Lactobacillus* (genus; e.g., genital site), *Lactobacillus* (genus; e.g., gut site), *Lactobacillus* (genus; e.g., nose site), *Lactobacillus* (genus; e.g., skin site), *Lactococcus* (genus; e.g., gut site), *Lactococcus* (genus; e.g., mouth site), *Lactococcus* (genus; e.g., nose site), *Lactococcus* (genus; e.g., skin site), *Lactonifactor* (genus; e.g., gut site), *Lautropia* (genus; e.g., gut site), *Leptotrichia* (genus; e.g., gut site), *Leptotrichia* (genus; e.g., nose site), *Leuconostoc* (genus; e.g., gut site), *Luteimonas* (genus; e.g., nose site), *Lysinibacillus* (genus; e.g., nose site), *Macrococcus* (genus; e.g., nose site), *Marvinbryantia* (genus; e.g., gut site), *Marvinbryantia* (genus; e.g., skin site), *Megamonas* (genus; e.g., skin site), *Megasphaera* (genus; e.g., gut site), *Megasphaera* (genus; e.g., mouth site), *Methanobrevibacter* (genus; e.g., nose site), *Methanomassiliicoccus* (genus; e.g., gut site), *Methylobacterium* (genus; e.g., gut site), *Methylobacterium* (genus; e.g., mouth site), *Methylobacterium* (genus; e.g., nose site), *Methylobacterium* (genus; e.g., skin site), *Micrococcus* (genus; e.g., gut site), *Micrococcus* (genus; e.g., nose site), *Micrococcus* (genus; e.g., skin site), *Mitsuokella* (genus; e.g., gut site), *Mobiluncus* (genus; e.g., gut site), *Mogibacterium* (genus; e.g., gut site), *Mogibacterium* (genus; e.g., mouth site), *Moraxella* (genus; e.g., mouth site), *Moraxella* (genus; e.g., nose site), *Moraxella* (genus; e.g., skin site), *Moryella* (genus; e.g., gut site), *Murdochiella* (genus; e.g., gut site), *Mycobacterium* (genus; e.g., gut site), *Mycobacterium* (genus; e.g., mouth site), *Mycobacterium* (genus; e.g., nose site), *Negativicoccus* (genus; e.g., gut site), *Neisseria* (genus; e.g., gut site), *Neisseria* (genus; e.g., mouth site), *Neisseria* (genus; e.g., nose site), *Neisseria* (genus; e.g., skin site), *Nocardioides* (genus; e.g., nose site), *Novosphingobium* (genus; e.g., skin site), *Ochrobactrum* (genus; e.g., nose site), *Ochrobactrum* (genus; e.g., skin site), *Odoribacter* (genus; e.g., gut site), *Odoribacter* (genus; e.g., nose site), *Odoribacter* (genus; e.g., skin site), *Oribacterium* (genus; e.g., mouth site), *Oscillibacter* (genus; e.g., gut site), *Oscillospira* (genus; e.g., gut site), *Oscillospira* (genus; e.g., nose site), *Pantoea* (genus; e.g., gut site), *Papillibacter* (genus; e.g., gut site), *Parabacteroides* (genus; e.g., gut site), *Parabacteroides* (genus; e.g., nose site), *Parabacteroides* (genus; e.g., skin site), *Parasporobacterium* (genus; e.g., gut site), *Parasutterella* (genus; e.g., gut site), *Parvibacter* (genus; e.g., gut site), *Parvimonas* (genus; e.g., gut site), *Parvimonas* (genus; e.g., mouth site), *Parvimonas* (genus; e.g., skin site), *Pasteurella* (genus; e.g., genital site), *Pasteurella* (genus; e.g., gut site), *Pasteurella* (genus; e.g., nose site), *Paucibacter* (genus; e.g., gut site), *Pedobacter* (genus; e.g., skin site), *Pelomonas* (genus; e.g., gut site), *Pelomonas* (genus; e.g., mouth site), *Pelomonas* (genus; e.g., nose site), *Pelomonas* (genus; e.g., skin site), *Peptoclostridium* (genus; e.g., gut site), *Peptococcus* (genus; e.g., gut site), *Peptoniphilus* (genus; e.g., genital site), *Peptoniphilus* (genus; e.g., gut site), *Peptoniphilus* (genus; e.g., skin site), *Peptostreptococcus* (genus; e.g., gut site), *Peptostreptococcus* (genus; e.g., skin site), *Phascolarctobacterium* (genus; e.g., gut site), *Phascolarctobacterium* (genus; e.g., skin site), *Photobacterium* (genus; e.g., skin site), *Phyllobacterium* (genus; e.g., skin site), *Porphyromonas* (genus; e.g., gut site), *Porphyromonas* (genus; e.g., mouth site), *Porphyromonas* (genus; e.g., nose site), *Prevotella* (genus; e.g., gut site), *Prevotella* (genus; e.g., mouth site), *Prevotella* (genus; e.g., nose site), *Propionibacterium* (genus; e.g., genital site), *Propionibacterium* (genus; e.g., gut site), *Propionibacterium* (genus; e.g., skin site), *Providencia* (genus; e.g., gut site), *Pseudoalteromonas* (genus; e.g., nose site), *Pseudobutyrivibrio* (genus; e.g., gut site), *Pseudobutyrivibrio* (genus; e.g., nose site), *Pseudobutyrivibrio* (genus; e.g., skin site), *Pseudoflavonifractor* (genus; e.g., gut site), *Pseudomonas* (genus; e.g., genital site), *Pseudomonas* (genus; e.g., gut site), *Pseudomonas* (genus; e.g., nose site), *Pseudomonas* (genus; e.g., skin site), *Ralstonia* (genus; e.g., nose site), *Ralstonia* (genus; e.g., skin site), *Rhizobium* (genus; e.g., nose site), *Rhizobium* (genus; e.g., skin site), *Rhodobacter* (genus; e.g., nose site), *Rhodococcus* (genus; e.g., nose site), *Rhodococcus* (genus; e.g., skin site), *Rikenella* (genus; e.g., gut site), *Robinsoniella* (genus; e.g., gut site), *Romboutsia* (genus; e.g., gut site), *Roseburia* (genus; e.g., gut site), *Roseburia* (genus; e.g., nose site), *Roseburia* (genus; e.g., skin site), *Rothia* (genus; e.g., gut site), *Rothia* (genus; e.g., nose site), *Rothia* (genus; e.g., skin site), *Sarcina* (genus; e.g., gut site), *Sarcina* (genus; e.g., mouth site), *Sarcina* (genus; e.g., nose site), *Sarcina* (genus; e.g., skin site), *Selenomonas* (genus; e.g., mouth site), *Senegalimassilia* (genus; e.g., gut site), *Shinella* (genus; e.g., nose site), *Shinella* (genus; e.g., skin site), *Shuttleworthia* (genus; e.g., gut site), *Slackia* (genus; e.g., gut site), *Solobacterium* (genus; e.g., gut site), *Solobacterium* (genus; e.g., mouth site), *Sphingomonas* (genus; e.g., nose site), *Sphingomonas* (genus; e.g., skin site), *Sporobacter* (genus; e.g., gut site), *Staphylococcus* (genus; e.g., nose site), *Stenotrophomonas* (genus; e.g., nose site), *Stomatobaculum* (genus; e.g., mouth site), *Streptococcus* (genus; e.g., gut site), *Streptococcus* (genus; e.g., mouth site), *Streptococcus* (genus; e.g., skin site), *Subdoligranulum* (genus; e.g., gut site), *Subdoligranulum* (genus; e.g., nose site), *Subdoligranulum* (genus; e.g., skin site), *Succinatimonas* (genus; e.g., gut site), *Succiniclasticum* (genus; e.g., gut site), *Succinivibrio* (genus; e.g., gut site), *Sutterella* (genus; e.g., gut site), *Sutterella* (genus; e.g., skin site), *Tannerella* (genus; e.g., mouth site), *Tannerella* (genus; e.g., nose site), *Terrisporobacter* (genus; e.g., gut site), *Tessaracoccus* (genus; e.g., mouth site), *Thalassospira* (genus; e.g., gut site), *Thalassospira* (genus; e.g., skin site), *Thermus* (genus; e.g., skin site), *Trichococcus* (genus; e.g., mouth site), *Turicella* (genus; e.g., skin site), *Turicibacter* (genus; e.g., gut site), *Varibaculum* (genus; e.g., gut site), *Variovorax* (genus; e.g., nose site), *Veillonella* (genus; e.g., gut site), *Veillonella* (genus; e.g., mouth site), *Veillonella* (genus; e.g., nose site), *Veillonella* (genus; e.g., skin site), *Victivallis* (genus; e.g., gut site), *Weissella* (genus; e.g., skin site), *Xanthomonas* (genus; e.g., skin site), *Abiotrophia defectiva* (species; e.g., nose site), *Acidaminococcus fermentans* (species; e.g., gut site), *Acidaminococcus intestini* (species; e.g., gut site), *Acidaminococcus* sp. BV3L6 (species; e.g., gut site), *Acinetobacter* sp. 423D (species; e.g., skin site), *Acinetobacter* sp. 8A12N5 (species; e.g., nose site), *Acinetobacter* sp. 8A12N5 (species; e.g., skin site), *Acinetobacter* sp. C—S-PDA7 (species; e.g., nose site), *Acinetobacter* sp. IHBB 5074 (species; e.g., nose site), *Actinobacillus porcinus* (species; e.g., genital site), *Actinobacillus porcinus* (species; e.g., gut site), *Actinobacillus porcinus* (species; e.g., mouth site), *Actinobacillus porcinus* (species; e.g., skin site), *Actinomyces dentalis* (species; e.g., mouth site), *Actinomyces massiliensis* (species; e.g., mouth site), *Actinomyces neuii* (species; e.g., mouth site), *Actinomyces neuii* (species; e.g., skin site), *Actinomyces odontolyticus* (species; e.g., gut site), *Actinomyces odontolyticus* (species; e.g., mouth site), *Actinomyces radingae* (species; e.g., gut site), *Actinomyces* sp. (species; e.g., mouth site), *Actinomyces* sp. 2002-2301122 (species; e.g., gut site), *Actinomyces* sp. ICM41 (species; e.g., mouth site), *Actinomyces* sp. ICM47 (species; e.g., gut site), *Actinomyces* sp. ICM54 (species; e.g., gut site), *Actinomyces* sp. ICM54 (species; e.g., nose site), *Actinomyces* sp. oral taxon 175 (species; e.g., gut site), *Actinomyces* sp. oral taxon 178 (species; e.g., mouth site), *Actinomyces* sp. oral taxon 448 (species; e.g., mouth site), *Actinomyces* sp. S9 PR-21 (species; e.g., gut site), *Actinomyces* sp. ZSY-1 (species; e.g., mouth site), *Actinomyces turicensis* (species; e.g., gut site), *Actinomyces viscosus* (species; e.g., mouth site), *Actinomyces viscosus* (species; e.g., nose site), *Adlercreutzia equolifaciens* (species; e.g., gut site), *Aerococcus christensenii* (species; e.g., gut site), *Aerosphaera taetra* (species; e.g., gut site), *Aggregatibacter aphrophilus* (species; e.g., gut site), *Aggregatibacter segnis* (species; e.g., mouth site), *Aggregatibacter segnis* (species; e.g., nose site), *Akkermansia muciniphila* (species; e.g., gut site), *Alistipes finegoldii* (species; e.g., gut site), *Alistipes indistinctus* (species; e.g., gut site), *Alistipes massiliensis* (species; e.g., gut site), *Alistipes putredinis* (species; e.g., gut site), *Alistipes putredinis* (species; e.g., nose site), *Alistipes putredinis* (species; e.g., skin site), *Alistipes shahii* (species; e.g., gut site), *Alistipes* sp. 627 (species; e.g., gut site), *Alistipes* sp. EBA6-25c12 (species; e.g., gut site), *Alistipes* sp. EBA6-25c12 (species; e.g., nose site), *Alistipes* sp. EBA6-25c12 (species; e.g., skin site), *Alistipes* sp. HGB5 (species; e.g., gut site), *Alistipes* sp. NML05A004 (species; e.g., gut site), *Alistipes* sp. RMA 9912 (species; e.g., gut site), *Alistipes* sp. RMA 9912 (species; e.g., nose site), *Alistipes* sp. RMA 9912 (species; e.g., skin site), *Allisonella histaminiformans* (species; e.g., gut site), *Alloscardovia omnicolens* (species; e.g., gut site), *Anaerococcus lactolyticus* (species; e.g., gut site), *Anaerococcus murdochii* (species; e.g., gut site), *Anaerococcus murdochii* (species; e.g., skin site), *Anaerococcus octavius* (species; e.g., gut site), *Anaerococcus octavius* (species; e.g., mouth site), *Anaerococcus octavius* (species; e.g., nose site), *Anaerococcus* sp. 8404299 (species; e.g., gut site), *Anaerococcus* sp. 9401487 (species; e.g., skin site), *Anaerococcus* sp. 9402080 (species; e.g., gut site), *Anaerococcus* sp. 9402080 (species; e.g., mouth site), *Anaerococcus* sp. S8 87-3 (species; e.g., gut site), *Anaerococcus* sp. S9 PR-16 (species; e.g., genital site), *Anaerococcus tetradius* (species; e.g., gut site), *Anaerococcus vaginalis* (species; e.g., genital site), *Anaerococcus vaginalis* (species; e.g., gut site), *Anaerosporobacter mobilis* (species; e.g., gut site), *Anaerostipes caccae* (species; e.g., gut site), *Anaerostipes hadrus* (species; e.g., gut site), *Anaerostipes* sp. 1y-2 (species; e.g., gut site), *Anaerostipes* sp. 5_1_63FAA (species; e.g., gut site), *Anaerostipes* sp. 5_1_63FAA (species; e.g., nose site), *Anaerostipes* sp. 5_1_63FAA (species; e.g., skin site), *Anaerostipes* sp. 992a (species; e.g., gut site), *Anaerotruncus colihominis* (species; e.g., gut site), *Anaerovibrio* sp. 765 (species; e.g., gut site), *Aquabacterium* sp. Aqua2 (species; e.g., gut site), *Aquabacterium* sp. Aqua2 (species; e.g., mouth site), *Aquabacterium* sp. Aqua2 (species; e.g., nose site), *Arcanobacterium* sp. NML 06501 (species; e.g., gut site), *Arthrobacter albus* (species; e.g., gut site), *Arthrobacter* sp. (species; e.g., gut site), *Asaccharospora irregularis* (species; e.g., gut site), *Asaccharospora irregularis* (species; e.g., nose site), *Atopobium parvulum* (species; e.g., mouth site), *Atopobium rimae* (species; e.g., mouth site), *Atopobium* sp. ICM57 (species; e.g., genital site), *Atopobium* sp. S3MV24 (species; e.g., genital site), *Atopobium* sp. S3MV24 (species; e.g., gut site), *Bacteroides acidifaciens* (species; e.g., gut site), *Bacteroides acidifaciens* (species; e.g., nose site), *Bacteroides acidifaciens* (species; e.g., skin site), *Bacteroides caccae* (species; e.g., gut site), *Bacteroides caccae* (species; e.g., skin site), *Bacteroides coprocola* (species; e.g., gut site), *Bacteroides coprophilus* (species; e.g., gut site), *Bacteroides dorei* (species; e.g., gut site), *Bacteroides eggerthii* (species; e.g., gut site), *Bacteroides faecis* (species; e.g., gut site), *Bacteroides finegoldii* (species; e.g., gut site), *Bacteroides intestinalis* (species; e.g., gut site), *Bacteroides massiliensis* (species; e.g., gut site), *Bacteroides massiliensis* (species; e.g., mouth site), *Bacteroides nordii* (species; e.g., gut site), *Bacteroides ovatus* (species; e.g., gut site), *Bacteroides plebeius* (species; e.g., gut site), *Bacteroides plebeius* (species; e.g., skin site), *Bacteroides salyersiae* (species; e.g., gut site), *Bacteroides* sp. (species; e.g., gut site), *Bacteroides* sp. 14(A) (species; e.g., gut site), *Bacteroides* sp. 3_1_400A (species; e.g., gut site), *Bacteroides* sp. 35AE37 (species; e.g., gut site), *Bacteroides* sp. 4072 (species; e.g., gut site), *Bacteroides* sp. AR20 (species; e.g., gut site), *Bacteroides* sp. AR20 (species; e.g., nose site), *Bacteroides* sp. AR20 (species; e.g., skin site), *Bacteroides* sp. AR29 (species; e.g., gut site), *Bacteroides* sp. AR29 (species; e.g., nose site), *Bacteroides* sp. AR29 (species; e.g., skin site), *Bacteroides* sp. C13EG172 (species; e.g., gut site), *Bacteroides* sp. D20 (species; e.g., gut site), *Bacteroides* sp. D22 (species; e.g., gut site), *Bacteroides* sp. D22 (species; e.g., nose site), *Bacteroides* sp. D22 (species; e.g., skin site), *Bacteroides* sp. DJF_B097 (species; e.g., gut site), *Bacteroides* sp. DJF_B097 (species; e.g., nose site), *Bacteroides* sp. DJF_B097 (species; e.g., skin site), *Bacteroides* sp. dnLKV9 (species; e.g., gut site), *Bacteroides* sp. EBA5-17 (species; e.g., gut site), *Bacteroides* sp. J1511 (species; e.g., gut site), *Bacteroides* sp. SLC1-38 (species; e.g., gut site), *Bacteroides* sp. SLC1-38 (species; e.g., nose site), *Bacteroides* sp. XB12B (species; e.g., gut site), *Bacteroides* sp. XB44A (species; e.g., gut site), *Bacteroides stercorirosoris* (species; e.g., gut site), *Bacteroides stercoris* (species; e.g., gut site), *Bacteroides thetaiotaomicron* (species; e.g., gut site), *Bacteroides uniformis* (species; e.g., gut site), *Bacteroides vulgatus* (species; e.g., genital site), *Bacteroides vulgatus* (species; e.g., gut site), *Bacteroides vulgatus* (species; e.g., nose site), *Bacteroides vulgatus* (species; e.g., skin site), *Bacteroides xylanisolvens* (species; e.g., gut site), *Barnesiella intestinihominis* (species; e.g., skin site), *Barnesiella* sp. 177 (species; e.g., gut site), *Bergeyella* sp. AF14 (species; e.g., mouth site), *Bifidobacterium adolescentis* (species; e.g., gut site), *Bifidobacterium animalis* (species; e.g., gut site), *Bifidobacterium biavatii* (species; e.g., gut site), *Bifidobacterium bifidum* (species; e.g., gut site), *Bifidobacterium choerinum* (species; e.g., gut site), *Bifidobacterium dentium* (species; e.g., gut site), *Bifidobacterium kashiwanohense* (species; e.g., gut site), *Bifidobacterium longum* (species; e.g., gut site), *Bifidobacterium longum* (species; e.g., nose site), *Bifidobacterium merycicum* (species; e.g., gut site), *Bifidobacterium pseudocatenulatum* (species; e.g., gut site), *Bifidobacterium pullorum* (species; e.g., gut site), *Bifidobacterium* sp. (species; e.g., gut site), *Bifidobacterium* sp. 120 (species; e.g., gut site), *Bifidobacterium stercoris* (species; e.g., genital site), *Bifidobacterium stercoris* (species; e.g., gut site), *Bifidobacterium tsurumiense* (species; e.g., gut site), *Bilophila* sp. 4_1_30 (species; e.g., gut site), *Bilophila* sp. 4_1_30 (species; e.g., skin site), *Bilophila wadsworthia* (species; e.g., gut site), *Blautia coccoides* (species; e.g., gut site), *Blautia faecis* (species; e.g., gut site), *Blautia faecis* (species; e.g., nose site), *Blautia faecis* (species; e.g., skin site), *Blautia glucerasea* (species; e.g., gut site), *Blautia hansenii* (species; e.g., gut site), *Blautia hydrogenotrophica* (species; e.g., gut site), *Blautia luti* (species; e.g., gut site), *Blautia luti* (species; e.g., nose site), *Blautia luti* (species; e.g., skin site), *Blautia producta* (species; e.g., gut site), *Blautia* sp. Ser8 (species; e.g., gut site), *Blautia* sp. YHC-4 (species; e.g., gut site), *Blautia stercoris*

(species; e.g., gut site), *Blautia wexlerae* (species; e.g., gut site), *Blautia wexlerae* (species; e.g., nose site), *Blautia wexlerae* (species; e.g., skin site), *Bradyrhizobium* sp. 68A4SAPT (species; e.g., gut site), *Bradyrhizobium* sp. 68A4SAPT (species; e.g., mouth site), *Bradyrhizobium* sp. 68A4SAPT (species; e.g., nose site), *Bradyrhizobium* sp. 68A4SAPT (species; e.g., skin site), *Brevibacterium paucivorans* (species; e.g., gut site), *Brevundimonas* sp. FXJ8.080 (species; e.g., mouth site), *Brevundimonas* sp. FXJ8.080 (species; e.g., nose site), *Brevundimonas* sp. FXJ8.080 (species; e.g., skin site), *Butyricimonas* sp. 214-4 (species; e.g., gut site), *Butyricimonas* sp. JCM 18676 (species; e.g., gut site), *Butyricimonas* sp. JCM 18677 (species; e.g., gut site), *Butyricimonas synergistica* (species; e.g., gut site), *Butyricimonas virosa* (species; e.g., gut site), *Butyrivibrio crossotus* (species; e.g., gut site), *Campylobacter concisus* (species; e.g., mouth site), *Campylobacter gracilis* (species; e.g., mouth site), *Campylobacter hominis* (species; e.g., gut site), *Campylobacter* sp. FOBRC15 (species; e.g., mouth site), *Campylobacter ureolyticus* (species; e.g., gut site), *Campylobacter ureolyticus* (species; e.g., nose site), *Capnocytophaga gingivalis* (species; e.g., mouth site), *Capnocytophaga* sp. AHN9687 (species; e.g., mouth site), *Capnocytophaga* sp. CM59 (species; e.g., nose site), *Capnocytophaga* sp. oral taxon 329 (species; e.g., nose site), *Cardiobacterium hominis* (species; e.g., mouth site), *Cardiobacterium valvarum* (species; e.g., mouth site), *Catenibacterium mitsuokai* (species; e.g., gut site), *Cellulosilyticum ruminicola* (species; e.g., gut site), *Centipeda periodontii* (species; e.g., gut site), *Centipeda periodontii* (species; e.g., mouth site), *Christensenella minuta* (species; e.g., gut site), *Citrobacter amalonaticus* (species; e.g., gut site), *Citrobacter* sp. BW4 (species; e.g., gut site), *Citrobacter* sp. BW4 (species; e.g., skin site), *Cloacibacillus evryensis* (species; e.g., gut site), *Cloacibacillus porcorum* (species; e.g., gut site), *Collinsella aerofaciens* (species; e.g., gut site), *Collinsella aerofaciens* (species; e.g., nose site), *Collinsella intestinalis* (species; e.g., gut site), *Coprobacillus* sp. D6 (species; e.g., gut site), *Coprobacter fastidiosus* (species; e.g., gut site), *Corynebacterium canis* (species; e.g., gut site), *Corynebacterium diphtheriae* (species; e.g., gut site), *Corynebacterium epidermidicanis* (species; e.g., gut site), *Corynebacterium epidermidicanis* (species; e.g., nose site), *Corynebacterium freiburgense* (species; e.g., gut site), *Corynebacterium freiburgense* (species; e.g., skin site), *Corynebacterium glucuronolyticum* (species; e.g., nose site), *Corynebacterium glucuronolyticum* (species; e.g., skin site), *Corynebacterium mastitidis* (species; e.g., gut site), *Corynebacterium matruchotii* (species; e.g., mouth site), *Corynebacterium matruchotii* (species; e.g., nose site), *Corynebacterium* sp. (species; e.g., genital site), *Corynebacterium* sp. (species; e.g., gut site), *Corynebacterium* sp. (species; e.g., mouth site), *Corynebacterium* sp. 713182/2012 (species; e.g., genital site), *Corynebacterium* sp. 713182/2012 (species; e.g., gut site), *Corynebacterium* sp. jw37 (species; e.g., gut site), *Corynebacterium* sp. jw37 (species; e.g., skin site), *Corynebacterium* sp. NML 97-0186 (species; e.g., nose site), *Corynebacterium* sp. NML 97-0186 (species; e.g., skin site), *Corynebacterium* sp. NML96-0085 (species; e.g., gut site), *Corynebacterium* sp. NML96-0085 (species; e.g., nose site), *Corynebacterium spheniscorum* (species; e.g., gut site), *Corynebacterium ulcerans* (species; e.g., skin site), *Deinococcus* sp. G3-6-20 (species; e.g., skin site), *Delftia lacustris* (species; e.g., gut site), *Delftia lacustris* (species; e.g., skin site), *Delftia* sp. BN-SKY3 (species; e.g., gut site), *Delftia* sp. BN-SKY3 (species; e.g., nose site), *Delftia* sp. BN-SKY3 (species; e.g., skin site), *Dermabacter* sp. HFH0086 (species; e.g., gut site), *Desulfovibrio desulfuricans* (species; e.g., gut site), *Desulfovibrio piger* (species; e.g., gut site), *Desulfovibrio* sp. 3_1_syn3 (species; e.g., gut site), *Dialister invisus* (species; e.g., gut site), *Dialister micraerophilus* (species; e.g., gut site), *Dialister pneumosintes* (species; e.g., gut site), *Dialister propionicifaciens* (species; e.g., gut site), *Dialister propionicifaciens* (species; e.g., nose site), *Dialister* sp. E2_20 (species; e.g., gut site), *Dialister* sp. S7MSR5 (species; e.g., gut site), *Dialister succinatiphilus* (species; e.g., gut site), *Dialister succinatiphilus* (species; e.g., mouth site), *Dielma fastidiosa* (species; e.g., gut site), *Dorea formicigenerans* (species; e.g., gut site), *Dorea formicigenerans* (species; e.g., nose site), *Dorea formicigenerans* (species; e.g., skin site), *Dorea longicatena* (species; e.g., gut site), *Dorea longicatena* (species; e.g., nose site), *Dorea longicatena* (species; e.g., skin site), *Dysgonomonas capnocytophagoides* (species; e.g., gut site), *Eggerthella lenta* (species; e.g., gut site), *Eggerthella* sp. HGA1 (species; e.g., gut site), *Eisenbergiella tayi* (species; e.g., gut site), *Enterobacter asburiae* (species; e.g., gut site), *Enterobacter* sp. BS2-1 (species; e.g., gut site), *Enterococcus faecalis* (species; e.g., gut site), *Enterococcus* sp. SI-4 (species; e.g., gut site), *Enterococcus* sp. SI-4 (species; e.g., skin site), *Eremococcus coleocola* (species; e.g., gut site), *Erysipelatoclostridium ramosum* (species; e.g., gut site), *Eubacterium limosum* (species; e.g., gut site), *Facklamia hominis* (species; e.g., gut site), *Faecalibacterium prausnitzii* (species; e.g., gut site), *Faecalibacterium prausnitzii* (species; e.g., nose site), *Faecalibacterium prausnitzii* (species; e.g., skin site), *Faecalibacterium* sp. canine oral taxon 147 (species; e.g., gut site), *Faecalibacterium* sp. canine oral taxon 147 (species; e.g., mouth site), *Finegoldia magna* (species; e.g., gut site), *Finegoldia magna* (species; e.g., nose site), *Finegoldia magna* (species; e.g., skin site), *Finegoldia* sp. S8 F7 (species; e.g., gut site), *Finegoldia* sp. S9 AA1-5 (species; e.g., gut site), *Flavobacterium ceti* (species; e.g., mouth site), *Flavobacterium ceti* (species; e.g., nose site), *Flavobacterium ceti* (species; e.g., skin site), *Flavonifractor plautii* (species; e.g., gut site), *Fusicatenibacter saccharivorans* (species; e.g., gut site), *Fusicatenibacter saccharivorans* (species; e.g., nose site), *Fusicatenibacter saccharivorans* (species; e.g., skin site), *Fusobacterium periodonticum* (species; e.g., gut site), *Fusobacterium periodonticum* (species; e.g., mouth site), *Fusobacterium* sp. ACB2 (species; e.g., gut site), *Fusobacterium* sp. AS2 (species; e.g., gut site), *Fusobacterium* sp. CM21 (species; e.g., skin site), *Fusobacterium* sp. CM22 (species; e.g., mouth site), *Gardnerella* sp. S3PF20 (species; e.g., gut site), *Gardnerella vaginalis* (species; e.g., gut site), *Gardnerella vaginalis* (species; e.g., skin site), *Gemella morbillorum* (species; e.g., gut site), *Gemella morbillorum* (species; e.g., mouth site), *Gemella morbillorum* (species; e.g., nose site), *Gemella sanguinis* (species; e.g., mouth site), *Gemella* sp. 933-88 (species; e.g., gut site), *Gemella* sp. 933-88 (species; e.g., mouth site), *Gemella* sp. 933-88 (species; e.g., skin site), *Gordonibacter pamelaeae* (species; e.g., gut site), *Gordonibacter* sp. CEBAS 1/15P (species; e.g., gut site), *Granulicatella adiacens* (species; e.g., gut site), *Granulicatella adiacens* (species; e.g., nose site), *Haemophilus influenzae* (species; e.g., gut site), *Haemophilus influenzae* (species; e.g., nose site), *Haemophilus parainfluenzae* (species; e.g., gut site), *Haemophilus parainfluenzae* (species; e.g., nose site), *Haemophilus parainfluenzae* (species; e.g., skin site), *Herbaspirillum huttiense* (species; e.g., skin site), *Herbaspirillum seropedicae* (species; e.g., gut site), *Herbaspirillum seropedicae* (species; e.g., skin site), *Holdemania filiformis* (species; e.g., gut site),

*Howardella ureilytica* (species; e.g., gut site), *Klebsiella* sp. B12 (species; e.g., gut site), *Klebsiella* sp. SOR89 (species; e.g., gut site), *Kluyvera georgiana* (species; e.g., genital site), *Kluyvera georgiana* (species; e.g., gut site), *Kluyvera georgiana* (species; e.g., nose site), *Lachnoanaerobaculum saburreum* (species; e.g., mouth site), *Lachnoanaerobaculum* sp. MSX33 (species; e.g., mouth site), *Lachnoanaerobaculum* sp. OBRC5-5 (species; e.g., mouth site), *Lachnospira pectinoschiza* (species; e.g., gut site), *Lachnospira pectinoschiza* (species; e.g., nose site), *Lachnospira pectinoschiza* (species; e.g., skin site), *Lactobacillus crispatus* (species; e.g., gut site), *Lactobacillus crispatus* (species; e.g., skin site), *Lactobacillus curvatus* (species; e.g., gut site), *Lactobacillus delbrueckii* (species; e.g., gut site), *Lactobacillus delbrueckii* (species; e.g., nose site), *Lactobacillus fermentum* (species; e.g., gut site), *Lactobacillus fornicalis* (species; e.g., gut site), *Lactobacillus gasseri* (species; e.g., gut site), *Lactobacillus iners* (species; e.g., genital site), *Lactobacillus iners* (species; e.g., gut site), *Lactobacillus mucosae* (species; e.g., gut site), *Lactobacillus paracasei* (species; e.g., gut site), *Lactobacillus plantarum* (species; e.g., gut site), *Lactobacillus rhamnosus* (species; e.g., gut site), *Lactobacillus ruminis* (species; e.g., gut site), *Lactobacillus salivarius* (species; e.g., gut site), *Lactobacillus* sp. 7_1_47FAA (species; e.g., genital site), *Lactobacillus* sp. 7_1_47FAA (species; e.g., gut site), *Lactobacillus* sp. BL302 (species; e.g., gut site), *Lactobacillus* sp. BL302 (species; e.g., nose site), *Lactobacillus* sp. CR-609S (species; e.g., gut site), *Lactobacillus* sp. TAB-26 (species; e.g., gut site), *Lactobacillus* sp. TAB-30 (species; e.g., nose site), *Lactobacillus vaginalis* (species; e.g., gut site), *Lactococcus lactis* (species; e.g., gut site), *Lactococcus* sp. D2 (species; e.g., gut site), *Lactococcus* sp. MH5-2 (species; e.g., gut site), *Lactococcus* sp. MH5-2 (species; e.g., mouth site), *Lactococcus* sp. MH5-2 (species; e.g., skin site), *Lactonifactor longoviformis* (species; e.g., gut site), *Lautropia* sp. TeTO (species; e.g., gut site), *Leptotrichia* genomosp. C1 (species; e.g., mouth site), *Leptotrichia* genomosp. C1 (species; e.g., nose site), *Leptotrichia hofstadii* (species; e.g., mouth site), *Leptotrichia hongkongensis* (species; e.g., mouth site), *Leptotrichia* sp. oral taxon 225 (species; e.g., mouth site), *Leptotrichia* sp. oral taxon 225 (species; e.g., nose site), *Leptotrichia* sp. PG10 (species; e.g., mouth site), *Leptotrichia wadei* (species; e.g., mouth site), *Leptotrichia wadei* (species; e.g., nose site), *Leuconostoc gelidum* (species; e.g., gut site), *Leuconostoc mesenteroides* (species; e.g., gut site), *Mannheimia varigena* (species; e.g., mouth site), *Megamonas funiformis* (species; e.g., skin site), *Megasphaera elsdenii* (species; e.g., gut site), *Megasphaera* genomosp. C1 (species; e.g., gut site), *Megasphaera* genomosp. C1 (species; e.g., mouth site), *Megasphaera* sp. NP3 (species; e.g., gut site), *Megasphaera* sp. TrE9262 (species; e.g., gut site), *Megasphaera* sp. UPII 199-6 (species; e.g., gut site), *Methanobrevibacter smithii* (species; e.g., nose site), *Methylobacterium* sp. RK-2008-1 (species; e.g., gut site), *Methylobacterium* sp. RK-2008-1 (species; e.g., mouth site), *Methylobacterium* sp. RK-2008-1 (species; e.g., nose site), *Methylobacterium* sp. RK-2008-1 (species; e.g., skin site), *Micrococcus luteus* (species; e.g., nose site), *Micrococcus* sp. WB18-oi (species; e.g., skin site), *Mitsuokella jalaludinii* (species; e.g., gut site), *Mitsuokella* sp. DJF_RR21 (species; e.g., gut site), *Mitsuokella* sp. TM-10 (species; e.g., gut site), *Mobiluncus curtisii* (species; e.g., gut site), *Mogibacterium* sp. CM96 (species; e.g., mouth site), *Moraxella* sp. BB37 (species; e.g., nose site), *Murdochiella asaccharolytica* (species; e.g., gut site), *Murdochiella* sp. S9 PR-10 (species; e.g., gut site), *Negativicoccus* sp. S5-A15 (species; e.g., gut site), *Negativicoccus succinicivorans* (species; e.g., gut site), *Neisseria elongata* (species; e.g., gut site), *Neisseria macacae* (species; e.g., mouth site), *Neisseria macacae* (species; e.g., nose site), *Neisseria macacae* (species; e.g., skin site), *Neisseria mucosa* (species; e.g., gut site), *Neisseria mucosa* (species; e.g., mouth site), *Neisseria mucosa* (species; e.g., skin site), *Neisseria oralis* (species; e.g., mouth site), *Neisseria* sp. SMC-A9199 (species; e.g., mouth site), *Ochrobactrum tritici* (species; e.g., nose site), *Odoribacter splanchnicus* (species; e.g., gut site), *Odoribacter splanchnicus* (species; e.g., nose site), *Odoribacter splanchnicus* (species; e.g., skin site), *Oribacterium* sp. oral taxon 078 (species; e.g., mouth site), *Oscillospira guilliermondii* (species; e.g., gut site), *Parabacteroides distasonis* (species; e.g., gut site), *Parabacteroides distasonis* (species; e.g., mouth site), *Parabacteroides merdae* (species; e.g., gut site), *Parabacteroides merdae* (species; e.g., nose site), *Parabacteroides* sp. 157 (species; e.g., gut site), *Paraprevotella clara* (species; e.g., gut site), *Parasporobacterium paucivorans* (species; e.g., gut site), *Parasutterella excrementihominis* (species; e.g., gut site), *Parvibacter caecicola* (species; e.g., gut site), *Parvimonas micra* (species; e.g., skin site), *Parvimonas* sp. oral taxon 393 (species; e.g., gut site), *Pasteurella pneumotropica* (species; e.g., genital site), *Pasteurella pneumotropica* (species; e.g., gut site), *Pasteurella pneumotropica* (species; e.g., nose site), *Pelomonas aquatica* (species; e.g., gut site), *Pelomonas aquatica* (species; e.g., mouth site), *Pelomonas aquatica* (species; e.g., nose site), *Pelomonas aquatica* (species; e.g., skin site), *Peptoclostridium difficile* (species; e.g., gut site), *Peptococcus* sp. S9 Pr-12 (species; e.g., gut site), *Peptoniphilus coxii* (species; e.g., gut site), *Peptoniphilus duerdenii* (species; e.g., gut site), *Peptoniphilus lacrimalis* (species; e.g., gut site), *Peptoniphilus* sp. 1-14 (species; e.g., gut site), *Peptoniphilus* sp. 1-14 (species; e.g., nose site), *Peptoniphilus* sp. 2002-2300004 (species; e.g., gut site), *Peptoniphilus* sp. 2002-38328 (species; e.g., genital site), *Peptoniphilus* sp. 2002-38328 (species; e.g., gut site), *Peptoniphilus* sp. 7-2 (species; e.g., gut site), *Peptoniphilus* sp. BV3AC2 (species; e.g., gut site), *Peptoniphilus* sp. DNF00840 (species; e.g., genital site), *Peptoniphilus* sp. gpacoi8A (species; e.g., gut site), *Peptoniphilus* sp. oral taxon 375 (species; e.g., gut site), *Peptoniphilus* sp. oral taxon 836 (species; e.g., gut site), *Peptoniphilus* sp. S4-A10 (species; e.g., gut site), *Peptoniphilus* sp. S9 PR-13 (species; e.g., gut site), *Peptostreptococcus anaerobius* (species; e.g., gut site), *Peptostreptococcus anaerobius* (species; e.g., skin site), *Phascolarctobacterium faecium* (species; e.g., gut site), *Phascolarctobacterium succinatutens* (species; e.g., gut site), *Phascolarctobacterium succinatutens* (species; e.g., nose site), *Photobacterium* sp. CAIM 866 (species; e.g., skin site), *Phyllobacterium* sp. T50 (species; e.g., skin site), *Porphyromonas asaccharolytica* (species; e.g., gut site), *Porphyromonas bennonis* (species; e.g., gut site), *Porphyromonas catoniae* (species; e.g., genital site), *Porphyromonas catoniae* (species; e.g., gut site), *Porphyromonas catoniae* (species; e.g., mouth site), *Porphyromonas catoniae* (species; e.g., nose site), *Porphyromonas endodontalis* (species; e.g., gut site), *Porphyromonas somerae* (species; e.g., genital site), *Porphyromonas somerae* (species; e.g., nose site), *Porphyromonas* sp. 2024b (species; e.g., gut site), *Porphyromonas* sp. 2026 (species; e.g., gut site), *Porphyromonas* sp. S8 86-12 (species; e.g., gut site), *Prevotella amnii* (species; e.g., gut site), *Prevotella bivia* (species; e.g., gut site), *Prevotella bivia* (species; e.g., mouth site), *Prevotella buccalis* (species; e.g., gut site), *Prevotella disiens* (species; e.g., gut site), *Prevotella disiens* (species; e.g., mouth site), *Prevotella maculosa* (species; e.g., mouth site),

*Prevotella nanceiensis* (species; e.g., gut site), *Prevotella nigrescens* (species; e.g., mouth site), *Prevotella oris* (species; e.g., mouth site), *Prevotella oulorum* (species; e.g., mouth site), *Prevotella* sp. S4-10 (species; e.g., gut site), *Prevotella* sp. WAL 2039G (species; e.g., genital site), *Prevotella* sp. WAL 2039G (species; e.g., gut site), *Prevotella timonensis* (species; e.g., gut site), *Prevotella timonensis* (species; e.g., nose site), *Propionibacterium acnes* (species; e.g., nose site), *Propionibacterium acnes* (species; e.g., skin site), *Propionibacterium* sp. KPL1844 (species; e.g., nose site), *Propionibacterium* sp. KPL1844 (species; e.g., skin site), *Propionibacterium* sp. KPL2005 (species; e.g., nose site), *Propionibacterium* sp. MSP09A (species; e.g., nose site), *Propionibacterium* sp. MSP09A (species; e.g., skin site), *Propionibacterium* sp. V07/12348 (species; e.g., nose site), *Propionibacterium* sp. V07/12348 (species; e.g., skin site), *Pseudobutyrivibrio ruminis* (species; e.g., gut site), *Pseudoclavibacter bifida* (species; e.g., gut site), *Pseudoflavonifractor capillosus* (species; e.g., gut site), *Pseudomonas brenneri* (species; e.g., gut site), *Pseudomonas brenneri* (species; e.g., mouth site), *Pseudomonas brenneri* (species; e.g., nose site), *Pseudomonas brenneri* (species; e.g., skin site), *Pseudomonas monteilii* (species; e.g., nose site), *Pseudomonas* sp. G1116 (species; e.g., skin site), *Pseudomonas* sp. GmFRB023 (species; e.g., nose site), *Pseudomonas* sp. GmFRB023 (species; e.g., skin site), *Pseudomonas* sp. PKG89 (species; e.g., skin site), *Ralstonia* sp. A52 (species; e.g., skin site), *Ralstonia* sp. S2.MAC.005 (species; e.g., skin site), *Robinsoniella* sp. KNHs210 (species; e.g., gut site), *Roseburia cecicola* (species; e.g., gut site), *Roseburia faecis* (species; e.g., gut site), *Roseburia hominis* (species; e.g., gut site), *Roseburia intestinalis* (species; e.g., gut site), *Roseburia intestinalis* (species; e.g., nose site), *Roseburia intestinalis* (species; e.g., skin site), *Roseburia inulinivorans* (species; e.g., gut site), *Roseburia inulinivorans* (species; e.g., skin site), *Roseburia* sp. 11SE39 (species; e.g., genital site), *Roseburia* sp. 11SE39 (species; e.g., gut site), *Roseburia* sp. 11SE39 (species; e.g., nose site), *Roseburia* sp. 11SE39 (species; e.g., skin site), *Roseburia* sp. 499 (species; e.g., gut site), *Roseburia* sp. DJF_RR73 (species; e.g., gut site), *Rothia aeria* (species; e.g., mouth site), *Rothia dentocariosa* (species; e.g., nose site), *Rothia mucilaginosa* (species; e.g., gut site), *Rothia mucilaginosa* (species; e.g., nose site), *Rothia* sp. THG-N7 (species; e.g., nose site), *Selenomonas* sp. CM52 (species; e.g., mouth site), *Shinella* sp. DR33 (species; e.g., nose site), *Shinella* sp. DR33 (species; e.g., skin site), *Slackia piriformis* (species; e.g., gut site), *Slackia* sp. NATIS (species; e.g., gut site), *Solobacterium* sp. S4-A19 (species; e.g., mouth site), *Sphingomonas* sp. 540 (species; e.g., nose site), *Sphingomonas* sp. 540 (species; e.g., skin site), *Staphylococcus aureus* (species; e.g., nose site), *Staphylococcus aureus* (species; e.g., skin site), *Staphylococcus* sp. 334802 (species; e.g., genital site), *Staphylococcus* sp. 334802 (species; e.g., gut site), *Staphylococcus* sp. 334802 (species; e.g., nose site), *Staphylococcus* sp. 334802 (species; e.g., skin site), *Staphylococcus* sp. C9I2 (species; e.g., gut site), *Staphylococcus* sp. C9I2 (species; e.g., nose site), *Staphylococcus* sp. WB18-16 (species; e.g., nose site), *Stenotrophomonas* sp. C-S-TSA3 (species; e.g., nose site), *Stenotrophomonas* sp. KITS-1 (species; e.g., nose site), *Stenotrophomonas* sp. KITS-1 (species; e.g., skin site), *Stenotrophomonas* sp. UYS033 (species; e.g., nose site), *Stenotrophomonas* sp. UYS033 (species; e.g., skin site), *Streptococcus agalactiae* (species; e.g., gut site), *Streptococcus dentirousetti* (species; e.g., gut site), *Streptococcus dysgalactiae* (species; e.g., gut site), *Streptococcus equinus* (species; e.g., gut site), *Streptococcus gordonii* (species; e.g., gut site), *Streptococcus gordonii* (species; e.g., mouth site), *Streptococcus gordonii* (species; e.g., nose site), *Streptococcus gordonii* (species; e.g., skin site), *Streptococcus mitis* (species; e.g., mouth site), *Streptococcus mutans* (species; e.g., gut site), *Streptococcus mutans* (species; e.g., mouth site), *Streptococcus parasanguinis* (species; e.g., gut site), *Streptococcus parasanguinis* (species; e.g., mouth site), *Streptococcus parasanguinis* (species; e.g., nose site), *Streptococcus peroris* (species; e.g., gut site), *Streptococcus peroris* (species; e.g., mouth site), *Streptococcus* sp. 11aThal (species; e.g., gut site), *Streptococcus* sp. 11aThal (species; e.g., mouth site), *Streptococcus* sp. 11aThal (species; e.g., nose site), *Streptococcus* sp. 11aThal (species; e.g., skin site), *Streptococcus* sp. 2011_Oral_MS_A3 (species; e.g., gut site), *Streptococcus* sp. 2011_Oral_MS_A3 (species; e.g., mouth site), *Streptococcus* sp. 2011_Oral_MS_A3 (species; e.g., nose site), *Streptococcus* sp. 2011_Oral_MS_A3 (species; e.g., skin site), *Streptococcus* sp. BS35a (species; e.g., gut site), *Streptococcus* sp. BS35a (species; e.g., mouth site), *Streptococcus* sp. BS35a (species; e.g., skin site), *Streptococcus* sp. oral taxon G59 (species; e.g., genital site), *Streptococcus* sp. oral taxon G59 (species; e.g., gut site), *Streptococcus* sp. oral taxon G63 (species; e.g., gut site), *Streptococcus* sp. oral taxon G63 (species; e.g., mouth site), *Streptococcus* sp. oral taxon G63 (species; e.g., skin site), *Streptococcus* sp. 816-11 (species; e.g., gut site), *Streptococcus thermophilus* (species; e.g., gut site), *Streptococcus thermophilus* (species; e.g., nose site), *Streptococcus thermophilus* (species; e.g., skin site), *Subdoligranulum variabile* (species; e.g., gut site), *Subdoligranulum variabile* (species; e.g., nose site), *Subdoligranulum variabile* (species; e.g., skin site), *Succinatimonas hippei* (species; e.g., gut site), *Sutterella* sp. YIT 12072 (species; e.g., gut site), *Sutterella stercoricanis* (species; e.g., gut site), *Sutterella wadsworthensis* (species; e.g., skin site), *Tannerella* sp. oral taxon BU063 (species; e.g., mouth site), *Tannerella* sp. oral taxon BU063 (species; e.g., nose site), *Terrisporobacter glycolicus* (species; e.g., gut site), *Tessaracoccus* sp. IPBSL-7 (species; e.g., mouth site), *Turicella otitidis* (species; e.g., skin site), *Turicibacter sanguinis* (species; e.g., gut site), *Varibaculum cambriense* (species; e.g., gut site), *Varibaculum* sp. CCUG 45114 (species; e.g., gut site), *Veillonella atypica* (species; e.g., gut site), *Veillonella dispar* (species; e.g., genital site), *Veillonella dispar* (species; e.g., mouth site), *Veillonella parvula* (species; e.g., gut site), *Veillonella parvula* (species; e.g., mouth site), *Veillonella rogosae* (species; e.g., gut site), *Veillonella* sp. 2011_Oral_VSA_D3 (species; e.g., gut site), *Veillonella* sp. 2011_Oral_VSA_D3 (species; e.g., mouth site), *Veillonella* sp. AS16 (species; e.g., gut site), *Veillonella* sp. CM60 (species; e.g., gut site), *Veillonella* sp. CM60 (species; e.g., mouth site), *Veillonella* sp. CM60 (species; e.g., nose site), *Veillonella* sp. CM60 (species; e.g., skin site), *Veillonella* sp. FFA-2014 (species; e.g., gut site), *Veillonella* sp. MSA12 (species; e.g., gut site), *Veillonella tobetsuensis* (species; e.g., mouth site), and *Victivallis vadensis* (species; e.g., gut site).

Additionally or alternatively, performing the characterization process of the dietary conditions that are associated with microorganisms that are tolerant of lactose and/or fermented foods can be based on microbiome features (e.g., microbiome function features) associated with one or more of (e.g., such as in relation to a corresponding sample site): carbohydrate Metabolism (KEGG2), Carbohydrate Metabolism (KEGG2), Translation (KEGG2), Genetic Information Processing (KEGG2), Transport and Catabolism (KEGG2), Neurodegenerative Diseases (KEGG2), Lipid Metabolism (KEGG2), Xenobiotics Biodegradation and Metabolism (KEGG2), Nervous System (KEGG2), Endocrine System (KEGG2), Energy Metabolism (KEGG2), Amino acid metabolism (KEGG3), Amino acid related enzymes (KEGG3), Aminoacyl-tRNA biosynthesis (KEGG3), Aminobenzoate degradation (KEGG3), Amyotrophic lateral sclerosis (ALS) (KEGG3), Ascorbate and aldarate metabolism (KEGG3), Biosynthesis and biodegradation of secondary metabolites (KEGG3), Bisphenol degradation (KEGG3), Butanoate metabolism (KEGG3), Carbohydrate metabolism (KEGG3), Carbon fixation pathways in prokaryotes (KEGG3), Cellular antigens (KEGG3), Chromosome (KEGG3), Citrate cycle (TCA cycle) (KEGG3), Cysteine and methionine metabolism (KEGG3), D-Alanine metabolism (KEGG3), Electron transfer carriers (KEGG3), Energy metabolism (KEGG3), Fructose and mannose metabolism (KEGG3), Geraniol degradation (KEGG3), Glutamatergic synapse (KEGG3), Glycerophospholipid metabolism (KEGG3), Glycosaminoglycan degradation (KEGG3), Glycosphingolipid biosynthesis—ganglio series (KEGG3), Glycosphingolipid biosynthesis—globo series (KEGG3), Glyoxylate and dicarboxylate metabolism (KEGG3), Huntington's disease (KEGG3), Inositol phosphate metabolism (KEGG3), Lipoic acid metabolism (KEGG3), Lipopolysaccharide biosynthesis (KEGG3), Lipopolysaccharide biosynthesis proteins (KEGG3), Lysosome (KEGG3), Membrane and intracellular structural molecules (KEGG3), Naphthalene degradation (KEGG3), Nicotinate and nicotinamide metabolism (KEGG3), Nitrogen metabolism (KEGG3), Other glycan degradation (KEGG3), Other transporters (KEGG3), Others (KEGG3), Oxidative phosphorylation (KEGG3), PPAR signaling pathway (KEGG3), Penicillin and cephalosporin biosynthesis (KEGG3), Pentose and glucuronate interconversions (KEGG3), Peptidoglycan biosynthesis (KEGG3), Peroxisome (KEGG3), Phenylalanine metabolism (KEGG3), Phosphatidylinositol signaling system (KEGG3), Phosphonate and phosphinate metabolism (KEGG3), Photosynthesis (KEGG3), Photosynthesis proteins (KEGG3), Pores ion channels (KEGG3), Protein processing in endoplasmic reticulum (KEGG3), Proximal tubule bicarbonate reclamation (KEGG3), Pyruvate metabolism (KEGG3), RNA polymerase (KEGG3), Replication, recombination and repair proteins (KEGG3), Ribosome (KEGG3), Ribosome Biogenesis (KEGG3), Sphingolipid metabolism (KEGG3), Terpenoid backbone biosynthesis (KEGG3), Thiamine metabolism (KEGG3), Transcription machinery (KEGG3), Translation proteins (KEGG3), Type I diabetes mellitus (KEGG3), Type II diabetes mellitus (KEGG3), and/or any other suitable functional feature.

Determining a diet-related characterization of a user can include characterizing a user with the dietary conditions associated with at least one of the microorganisms that are tolerant of lactose and/or fermented foods based upon one or more of the above microbiome features and/or other suitable features described herein, such as in an additional or alternative manner to typical methods of diagnosis or characterization. However, features used in the diet characterization process can include any other suitable features (e.g., features useful for diagnostics), and performing the characterization process for the dietary conditions that are associated with at least one of the microorganisms that are tolerant of lactose and/or fermented foods can be performed in any suitable manner.

3.3.H Characterization Process: Dairy Allergy-Associated Diets.

In another variation, Block S130 can include performing a diet condition characterization process (e.g., determining and/or applying a diet characterization model; etc.) for one or more users, in relation to dairy diet-associated diets. In an example, a characterization process (e.g., of Block S130; based upon statistical analyses and/or other suitable approaches described herein; etc.) can identify a set of microbiome features (e.g., microbiome composition features, microbiome function features, etc.) with correlations (e.g., positive correlations, negative correlations, correlations of greatest magnitude, etc.) with at least one of the above diet conditions. In another example, performing a diet condition characterization process can facilitate identifications of one or more health-supporting measures operable to have a positive effect or maintaining effect for subjects with at least one of the above diets (e.g., based upon a random forest predictor algorithm trained with a training dataset derived from a subset of the population of subjects, and validated with a validation dataset derived from a subset of the population of subjects). In particular, dairy-diet associated diets can be a result of an immune disorder characterized by an abnormal reaction of the immune system of the subject to any of the proteins present in milk (i.e: cow's milk) or any other dairy or milk-derived product, and diagnosis is associated with laboratory analysis (i.e: skin-prick test, blood-samples analysis, IgE tests, etc.).

Performing the characterization process of the dairy diet-associated diets can be based on microbiome features (e.g., microbiome composition features) associated with (e.g., derived from, informative of, correlated with, etc.) one or more (e.g. in any suitable combination) of the following taxons: *Blautia luti* (species), *Collinsella aerofaciens* (species), *Flavonifractor plautii* (species), *Roseburia inulinivorans* (species), *Parabacteroides distasonis* (species), *Faecalibacterium prausnitzii* (species), *Dorea formicigenerans* (species), *Barnesiella intestinihominis* (species), *Subdoligranulum variabile* (species), *Bacteroides fragilis* (species), *Alistipes putredinis* (species), *Bacteroides vulgatus* (species), *Odoribacters planchnicus* (species), *Streptococcus thermophiles* (species), *Bacteroides thetaiotaomicron* (species), *Bacteroides caccae* (species), *Erysipelatoclostridium ramosum* (species), *Dorea* (genus), *Subdoligranulum* (genus), *Marvinbryantia* (genus), *Bacteroides* (genus), *Intestinibacter* (genus), *Sarcina* (genus), *Terrisporobacter* (genus), *Collinsella* (genus), *Faecalibacterium* (genus), *Moryella* (genus), *Barnesiella* (genus), *Bifidobacterium* (genus), *Sutterella* (genus), *Eggerthella* (genus), *Intestinimonas* (genus), *Anaerosporobacter* (genus), *Hespellia* (genus), *Thalassospira* (genus), *Streptococcus* (genus), *Parabacteroides* (genus), *Roseburia* (genus), *Butyricimonas* (genus), *Akkermansia* (genus), *Anaerotruncus* (genus), *Oscillospira* (genus), *Odoribacter* (genus), Ruminococcaceae (family), Bacteroidaceae (family), Oscillospiraceae (family), Streptococcaceae (family), Coriobacteriaceae (family), Bifidobacteriaceae (family), Clostridiaceae (family), Rhodospirillaceae (family), Peptostreptococcaceae (family), Verrucomicrobiaceae (family), Sutterellaceae (family), Porphyromonadaceae (family), Prevotellaceae (family), Bacteroidales (Order), Clostridiales (Order), Flavobacteriales (order), Coriobacteriales (order), Bifidobacteriales (order), Rhodospirillales (order), Verrucomicrobiales (order), Burkholderiales (order), Bacteroidia (class), Actinobacteria (class), Clostridia (class), Flavobacteriia (class), Alphaproteobacteria (class), Verrucomicrobiae (class), Betaproteobacteria (class), Bacteroidetes (phylum), Actinobacteria (phylum), and Firmicutes (phylum) and Verrucomicrobia (phylum).

Additionally or alternatively, performing the characterization process of the dairy diet-associated diets can be based on microbiome features (e.g., microbiome function features) associated with one or more of (e.g., such as in relation to a corresponding sample site): Metabolism (KEGG2), Carbohydrate Metabolism (KEGG2), Biosynthesis of Other Secondary Metabolites (KEGG2), Transport and Catabolism (KEGG2), Translation (KEGG2), Glycan Biosynthesis and Metabolism (KEGG2), Genetic Information Processing (KEGG2), Cellular Processes and Signaling (KEGG2), Replication and Repair (KEGG2), Lipid Metabolism (KEGG2), Nucleotide Metabolism (KEGG2), Signal Transduction (KEGG2), Metabolism of Cofactors and Vitamins (KEGG2), Cell Growth and Death (KEGG2), Signaling Molecules and Interaction (KEGG2), Enzyme Families (KEGG2), Metabolism of Terpenoids and Polyketides (KEGG2), Endocrine System (KEGG2), Poorly Characterized (KEGG2), Ribosome Biogenesis (KEGG3), Sphingolipid metabolism (KEGG3), D-Alanine metabolism (KEGG3), Pentose and glucuronate interconversions (KEGG3), Other glycan degradation (KEGG3), Glycosphingolipid biosynthesis—globo series (KEGG3), Others (KEGG3), Carbohydrate metabolism (KEGG3), Galactose metabolism (KEGG3), Lysosome (KEGG3), Lipoic acid metabolism (KEGG3), RNA polymerase (KEGG3), Glycosaminoglycan degradation (KEGG3), Translation proteins (KEGG3), Bisphenol degradation (KEGG3), Amino acid related enzymes (KEGG3), Cyanoamino acid metabolism (KEGG3), Peptidoglycan biosynthesis (KEGG3), Penicillin and cephalosporin biosynthesis (KEGG3), Inorganic ion transport and metabolism (KEGG3), Fructose and mannose metabolism (KEGG3), Phenylpropanoid biosynthesis (KEGG3), Ascorbate and aldarate metabolism (KEGG3), Amino sugar and nucleotide sugar metabolism (KEGG3), Ribosome biogenesis in eukaryotes (KEGG3), Glycosphingolipid biosynthesis—ganglio series (KEGG3), DNA repair and recombination proteins (KEGG3), Inositol phosphate metabolism (KEGG3), Ribosome (KEGG3), Aminoacyl-tRNA biosynthesis (KEGG3), Phosphatidylinositol signaling system (KEGG3), Nicotinate and nicotinamide metabolism (KEGG3), Translation factors (KEGG3), "Replication (KEGG3), recombination and repair proteins" (KEGG3), Pentose phosphate pathway (KEGG3), Cysteine and methionine metabolism (KEGG3), Cell motility and secretion (KEGG3), Sulfur metabolism (KEGG3), Chromosome (KEGG3), Streptomycin biosynthesis (KEGG3), Selenocompound metabolism (KEGG3), Terpenoid backbone biosynthesis (KEGG3), Benzoate degradation (KEGG3), Other transporters (KEGG3), Biotin metabolism (KEGG3), Pyrimidine metabolism (KEGG3), Membrane and intracellular structural molecules (KEGG3), Pores ion channels (KEGG3), Starch and sucrose metabolism (KEGG3), Lipopolysaccharide biosynthesis proteins (KEGG3), Amino acid metabolism (KEGG3), Homologous recombination (KEGG3), Bacterial toxins (KEGG3), Cell cycle—*Caulobacter* (KEGG3), Signal transduction mechanisms (KEGG3), beta-Lactam resistance (KEGG3), Huntington's disease (KEGG3), Other ion-coupled transporters (KEGG3), Type II diabetes mellitus (KEGG3), Ion channels (KEGG3), Nucleotide excision repair (KEGG3), Histidine metabolism (KEGG3), Taurine and hypotaurine metabolism (KEGG3), Carbohydrate digestion and absorption (KEGG3), Peroxisome (KEGG3), Purine metabolism (KEGG3), Glyoxylate and dicarboxylate metabolism (KEGG3), Mismatch repair (KEGG3), Insulin signaling pathway (KEGG3), Biosynthesis and biodegradation of secondary metabolites (KEGG3), DNA replication proteins (KEGG3), Function unknown (KEGG3), Type I diabetes mellitus (KEGG3), Nucleotide metabolism (KEGG3), Drug metabolism—cytochrome P450 (KEGG3), Propanoate metabolism (KEGG3), Polyketide sugar unit biosynthesis (KEGG3), Phenylalanine metabolism (KEGG3), Protein export (KEGG3), Metabolism of xenobiotics by cytochrome P450 (KEGG3), Riboflavin metabolism (KEGG3), DNA replication (KEGG3), "Glycine (KEGG3), serine and threonine metabolism" (KEGG3), Two-component system (KEGG3), Butirosin and neomycin biosynthesis (KEGG3), Lipid metabolism (KEGG3), Transcription machinery (KEGG3), Glycerolipid metabolism (KEGG3), Pantothenate and CoA biosynthesis (KEGG3), Peptidases (KEGG3), Restriction enzyme (KEGG3), Plant-pathogen interaction (KEGG3), Geraniol degradation (KEGG3), Synthesis and degradation of ketone bodies (KEGG3), Fatty acid metabolism (KEGG3), Glycosyltransferases (KEGG3), "Alanine (KEGG3) and aspartate and glutamate metabolism" (KEGG3), and/or any other suitable functional feature.

Determining a diet-related characterization of a user can include characterizing a user with the dairy diet-associated diets based upon one or more of the above microbiome features and/or other suitable features described herein, such as in an additional or alternative manner to typical methods of diagnosis or characterization. However, features used in the diet characterization process can include any other suitable features (e.g., features useful for diagnostics), and performing the characterization process for the dairy diet-associated diets can be performed in any suitable manner.

Characterization of the subject(s) can additionally or alternatively implement use of a high false positive test and/or a high false negative test to further analyze sensitivity of the characterization process in supporting analyses generated according to embodiments of the method 100.

3.4 Method—Determining a Therapy Model for Health-Supporting Measures Associated with Diet.

Block S140 recites: generating a therapy model configured to modulate microorganism distributions in subjects characterized according to the characterization process, wherein the therapy model is associated with health-supporting measures for improving subjects following one or more of the above diets. Block S140 functions to identify or predict health-supporting measures (e.g., probiotic-based health-supporting measures, phage-based health-supporting measures, small molecule-based health-supporting measures, etc.) that can shift a subject's microbiome composition and/or functional features toward a desired equilibrium state in promotion of the subject's health. In Block S140, the health-supporting measures can be selected from health-supporting measures including one or more of: probiotic health-supporting measures, phage-based health-supporting measures, small molecule-based health-supporting measures, cognititive/behavioral health-supporting measures, physical rehabilitation health-supporting measures, clinical health-supporting measures, medication-based health-supporting measures, diet-related health-supporting measures, and/or any other suitable therapy designed to operate in any other suitable manner in promoting a user's health. In a specific example of a bacteriophage-based therapy, one or more populations (e.g., in terms of colony forming units) of bacteriophages specific to a certain bacteria (or other microorganism) represented in the subject can be used to down-regulate or otherwise eliminate populations of the certain bacteria. As such, bacteriophage-based therapies can be used to reduce the size(s) of the undesired population(s) of bacteria represented in the subject. Complementarily, bacteriophage-based therapies can be used to increase the relative abundances of bacterial populations not targeted by the bacteriophage(s) used.

Figure 4:
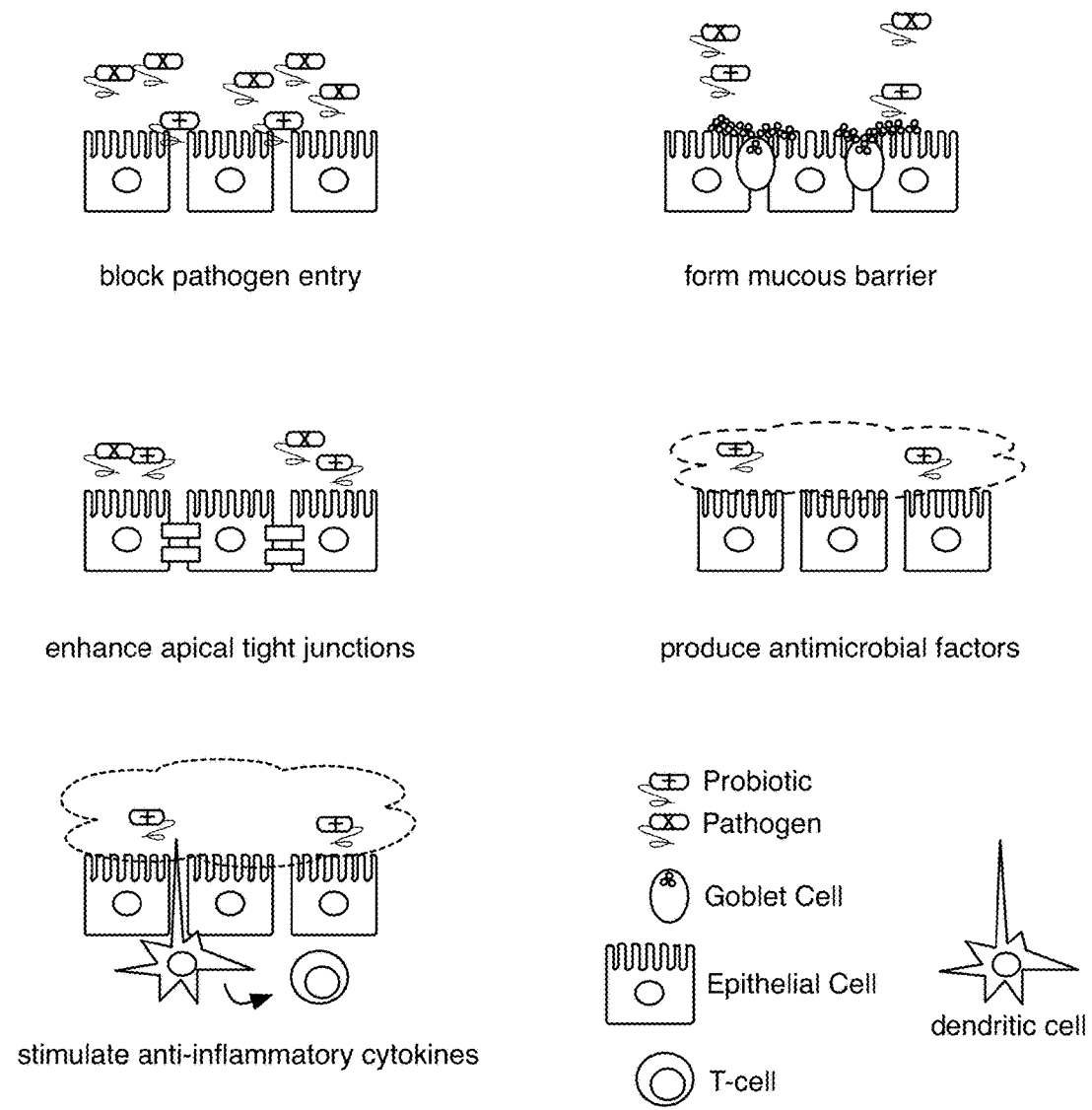
FIG. 4 depicts variations of mechanisms by which probiotic-based therapies operate in an embodiment of a method.

In another specific example of probiotic In another specific example of probiotic therapies, as shown in FIG. 4, candidate therapies of the therapy model can perform one or more of: blocking pathogen entry into an epithelial cell by providing a physical barrier (e.g., by way of colonization resistance), inducing formation of a mucous barrier by stimulation of goblet cells, enhance integrity of apical tight junctions between epithelial cells of a subject (e.g., by stimulating up regulation of zona-occludens 1, by preventing tight junction protein redistribution), producing antimicrobial factors, stimulating production of anti-inflammatory cytokines (e.g., by signaling of dendritic cells and induction of regulatory T-cells), triggering an immune response, and performing any other suitable function that adjusts a subject's microbiome away from a state of dysbiosis.

In another specific example, health-supporting measures can include medical-device based therapies (e.g., food-allergen detection devices; food-allergen medication provision devices; etc.). In another specific example, health supporting measures can include In variations, the therapy model is preferably based upon data from a large population of subjects, which can include the population of subjects from which the microbiome diversity datasets are derived in Block S110, where microbiome composition and/or functional features or states of health, prior exposure to and post exposure to a variety of health-supporting measures, are well characterized. Such data can be used to train and validate the therapy provision model, in identifying therapeutic measures that provide desired outcomes for subjects based upon different microbiome characterizations. In variations, support vector machines, as a supervised machine learning algorithm, can be used to generate the therapy provision model. However, any other suitable machine learning algorithm described above can facilitate generation of the therapy model.

While some methods of statistical analyses and machine learning are described in relation to performance of the Blocks above, variations of the method 100 can additionally or alternatively utilize any other suitable algorithms in performing the characterization process and/or therapy model generation process. In variations, the algorithm(s) can be characterized by a learning style including any one or more of: supervised learning (e.g., using logistic regression, using back propagation neural networks), unsupervised learning (e.g., using an Apriori algorithm, using K-means clustering), semi-supervised learning, reinforcement learning (e.g., using a Q-learning algorithm, using temporal difference learning), and any other suitable learning style. Furthermore, the algorithm(s) can implement any one or more of: a regression algorithm (e.g., ordinary least squares, logistic regression, stepwise regression, multivariate adaptive regression splines, locally estimated scatterplot smoothing, etc.), an instance-based method (e.g., k-nearest neighbor, learning vector quantization, self-organizing map, etc.), a regularization method (e.g., ridge regression, least absolute shrinkage and selection operator, elastic net, etc.), a decision tree learning method (e.g., classification and regression tree, iterative dichotomiser 3, C4.5, chi-squared automatic interaction detection, decision stump, random forest, multivariate adaptive regression splines, gradient boosting machines, etc.), a Bayesian method (e.g., naïve Bayes, averaged one-dependence estimators, Bayesian belief network, etc.), a kernel method (e.g., a support vector machine, a radial basis function, a linear discriminate analysis, etc.), a clustering method (e.g., k-means clustering, expectation maximization, etc.), an associated rule learning algorithm (e.g., an Apriori algorithm, an Eclat algorithm, etc.), an artificial neural network model (e.g., a Perceptron method, a back-propagation method, a Hopfield network method, a self-organizing map method, a learning vector quantization method, etc.), a deep learning algorithm (e.g., a restricted Boltzmann machine, a deep belief network method, a convolution network method, a stacked auto-encoder method, etc.), a dimensionality reduction method (e.g., principal component analysis, partial lest squares regression, Sammon mapping, multidimensional scaling, projection pursuit, etc.), an ensemble method (e.g., boosting, boostrapped aggregation, AdaBoost, stacked generalization, gradient boosting machine method, random forest method, etc.), and any suitable form of algorithm.

Additionally or alternatively, the therapy model can be derived in relation to identification of a "normal" or baseline microbiome composition and/or functional features, as assessed from subjects of a population of subjects who are identified to be in good health or otherwise in control states in relation to dietary conditions. Upon identification of a subset of subjects of the population of subjects who are characterized to be in improved health (e.g., using features of the characterization process), health-supporting measures that modulate microbiome compositions and/or functional features toward those of subjects in improved health can be generated in Block S140. Block S140 can thus include identification of one or more baseline microbiome compositions and/or functional features (e.g., one baseline microbiome for each of a set of demographics), and potential therapy formulations and therapy regimens that can shift microbiomes of subjects who are in a state of dysbiosis toward one of the identified baseline microbiome compositions and/or functional features. The therapy model can, however, be generated and/or refined in any other suitable manner.

Microorganism compositions associated with probiotic health-supporting measures associated with the therapy model preferably include microorganisms that are culturable (e.g., able to be expanded to provide a scalable therapy) and non-lethal (e.g., non-lethal in their desired therapeutic dosages). Furthermore, microorganism compositions can include a single type of microorganism that has an acute or moderated effect upon a subject's microbiome. Additionally or alternatively, microorganism compositions can include balanced combinations of multiple types of microorganisms that are configured to cooperate with each other in driving a subject's microbiome toward a desired state. For instance, a combination of multiple types of bacteria in a probiotic health-supporting measure can include a first bacteria type that generates products that are used by a second bacteria type that has a strong effect in positively affecting a subject's microbiome. Additionally or alternatively, a combination of multiple types of bacteria in a probiotic therapy can include several bacteria types that produce proteins with the same functions that positively affect a subject's microbiome.

Probiotic compositions can be naturally or synthetically derived. For instance, in one application, a probiotic composition can be naturally derived from fecal matter or other biological matter (e.g., of one or more subjects having a baseline microbiome composition and/or functional features, as identified using the characterization process and the therapy model). Additionally or alternatively, probiotic compositions can be synthetically derived (e.g., derived using a benchtop method) based upon a baseline microbiome composition and/or functional features, as identified using the characterization process and the therapy model. In variations, microorganism agents that can be used in probiotic health-supporting measures can include one or more of: yeast (e.g., *Saccharomyces boulardii*), gram-negative bacteria (e.g., *E. coli* Nissle), gram-positive bacteria (e.g., *Bifidobacteria bifidum, Bifidobacteria infantis, Lactobacillus rhamnosus, Lactococcus lactis, Lactobacillus plantarum, Lactobacillus acidophilus, Lactobacillus casei, Bacillus polyfermenticus*, etc.), and any other suitable type of microorganism agent.

In a variation, for subjects who follow one or more of the diets in Section 3.3.A. above, a health-supporting measure can include a combination of one or more taxons of microorganisms or other compositions associated with the taxonomic and functional features of Section 3.3.A., that modulate microbiome composition and/or function of the microbiome of the subject toward a desired state, thereby improving or maintaining health of the subject(s).

In a variation, for subjects who follow one or more of the diets in Section 3.3.B. above, a health-supporting measure can include a combination of one or more taxons of microorganisms or other compositions associated with the taxonomic and functional features of Section 3.3.B., that modulate microbiome composition and/or function of the microbiome of the subject toward a desired state, thereby improving or maintaining health of the subject(s).

In a variation, for subjects who follow one or more of the diets in Section 3.3.C. above, a health-supporting measure can include a combination of one or more taxons of microorganisms or other compositions associated with the taxonomic and functional features of Section 3.3.C., that modulate microbiome composition and/or function of the microbiome of the subject toward a desired state, thereby improving or maintaining health of the subject(s).

In a variation, for subjects who follow one or more of the diets in Section 3.3.D. above, a health-supporting measure can include a combination of one or more taxons of microorganisms or other compositions associated with the taxonomic and functional features of Section 3.3.D., that modulate microbiome composition and/or function of the microbiome of the subject toward a desired state, thereby improving or maintaining health of the subject(s).

In a variation, for subjects who follow one or more of the diets in Section 3.3.E. above, a health-supporting measure can include a combination of one or more taxons of microorganisms or other compositions associated with the taxonomic and functional features of Section 3.3.E., that modulate microbiome composition and/or function of the microbiome of the subject toward a desired state, thereby improving or maintaining health of the subject(s).

In a variation, for subjects who follow one or more of the diets in Section 3.3.F. above, a health-supporting measure can include a combination of one or more taxons of microorganisms or other compositions associated with the taxonomic and functional features of Section 3.3.F., that modulate microbiome composition and/or function of the microbiome of the subject toward a desired state, thereby improving or maintaining health of the subject(s).

In a variation, for subjects who follow one or more of the diets in Section 3.3.G. above, a health-supporting measure can include a combination of one or more taxons of microorganisms or other compositions associated with the taxonomic and functional features of Section 3.3.G., that modulate microbiome composition and/or function of the microbiome of the subject toward a desired state, thereby improving or maintaining health of the subject(s).

In a variation, for subjects who follow one or more of the diets in Section 3.3.H. above, a health-supporting measure can include a combination of one or more taxons of microorganisms or other compositions associated with the taxonomic and functional features of Section 3.3.H., that modulate microbiome composition and/or function of the microbiome of the subject toward a desired state, thereby improving or maintaining health of the subject(s).

Probiotics and/or other suitable consumables can be provided at dosages of 0.1 million to 10 billion CFUs (and/or other suitable dosages), such as determined from a therapy model that predicts positive adjustment of a patient's microbiome in response to the therapy. In a specific example, a subject can be instructed to ingest capsules comprising the probiotic formulation according to a regimen tailored to one or more of his/her: physiology (e.g., body mass index, weight, height), demographics (e.g., gender, age), severity of dysbiosis, sensitivity to medications, and any other suitable factor.

For subjects who exhibit a diet-related condition, associated-microorganisms (e.g., corresponding to correlated microbiome composition features) can provide a dataset based on composition and/or diversity of recognizable patterns of relative abundance in microorganisms that are present in subject microbiome, and can be used as a diagnostic tool using bioinformatics pipelines and characterization describe above.

3.5 Processing a User Biological Sample.

The method 100 can additionally or alternatively include Block S150, which recites: processing one or more biological samples from a user (e.g., subject). Block S150 can function to facilitate generation of a microbiome dataset for the subject that can be used to derive inputs for the characterization process (e.g., for generating a diet-related characterization for the user, etc.). As such, Block S150 can include receiving, processing, and/or analyzing one or more biological samples from one or more users (e.g., multiple biological samples for the same user over time, different biological samples for different users, etc.). In Block S150, the biological sample is preferably generated from the subject and/or an environment of the subject in a non-invasive manner. In variations, non-invasive manners of sample reception can use any one or more of: a permeable substrate (e.g., a swab configured to wipe a region of a subject's body, toilet paper, a sponge, etc.), a non-permeable substrate (e.g., a slide, tape, etc.) a container (e.g., vial, tube, bag, etc.) configured to receive a sample from a region of a subject's body, and any other suitable sample-reception element. In a specific example, the biological sample can be collected from one or more of the subject's nose, skin, genitals, mouth, and gut in a non-invasive manner (e.g., using a swab and a vial). However, the biological sample can additionally or alternatively be received in a semi-invasive manner or an invasive manner. In variations, invasive manners of sample reception can use any one or more of: a needle, a syringe, a biopsy element, a lance, and any other suitable instrument for collection of a sample in a semi-invasive or invasive manner. In specific examples, samples can include blood samples, plasma/serum samples (e.g., to enable extraction of cell-free DNA), and tissue samples.

In the above variations and examples, the biological sample can be taken from the body of the subject without facilitation by another entity (e.g., a caretaker associated with a subject, a health care professional, an automated or semi-automated sample collection apparatus, etc.), or can alternatively be taken from the body of the subject with the assistance of another entity. In one example, where the biological sample is taken from the subject without facilitation by another entity in the sample extraction process, a sample-provision kit can be provided to the subject. In the example, the kit can include one or more swabs for sample acquisition, one or more containers configured to receive the swab(s) for storage, instructions for sample provision and setup of a user account, elements configured to associate the sample(s) with the subject (e.g., barcode identifiers, tags, etc.), and a receptacle that allows the sample(s) from the subject to be delivered to a sample processing operation (e.g., by a mail delivery system). In another example, where the biological sample is extracted from the subject with the help of another entity, one or more samples can be collected in a clinical or research setting from the subject (e.g., during a clinical appointment). The biological sample can, however, be received from the subject in any other suitable manner.

Furthermore, processing and analyzing the biological sample (e.g., to generate a user microbiome dataset; etc.) from the subject is preferably performed in a manner similar to that of one of the embodiments, variations, and/or examples of sample reception described in relation to Block S110 above, and/or any other suitable portions of the method 100. As such, reception and processing of the biological sample in Block S150 can be performed for the subject using similar processes as those for receiving and processing biological samples used to generate the characterization process and/or the therapy model of the method 100, in order to provide consistency of process. However, biological sample reception and processing in Block S150 can alternatively be performed in any other suitable manner.

3.6 Determining a Diet-Related Characterization.

The method 100 can additionally or alternatively include Block S160, which recites: determining, with the characterization process, a diet-related characterization for the user based upon processing a microbiome dataset (e.g., user microorganism sequence dataset, microbiome composition dataset, microbiome functional diversity dataset, etc.) derived from the biological sample of the user. Block S160 can function to characterize one or more diet-related conditions for a user, such as through extracting features from microbiome-derived data of the subject, and using the features as inputs into an embodiment, variation, or example of the characterization process described in Block S130 above. In an example, Block S160 can include generating a diet-related characterization for the user based on user microbiome features and a diet-related condition characterization model (e.g., generated in Block S130). Diet-related characterizations can be for any number and/or combination of diet-related conditions (e.g., a combination of diet-related conditions, a single diet-related condition, and/or other suitable diet-related conditions; etc.). Diet-related characterizations can include one or more of: diagnoses (e.g., presence or absence of a diet-related condition; etc.); diet trigger profiles, risk (e.g., risk scores for developing and/or the presence of a diet-related condition; information regarding diet-related characterizations (e.g., symptoms, signs, triggers, associated conditions, etc.); comparisons (e.g., comparisons with other subgroups, populations, users, historic health statuses of the user such as historic microbiome compositions and/or functional diversities; comparisons associated with diet-related conditions; etc.), and/or any other suitable diet-related data.

Figure 7:
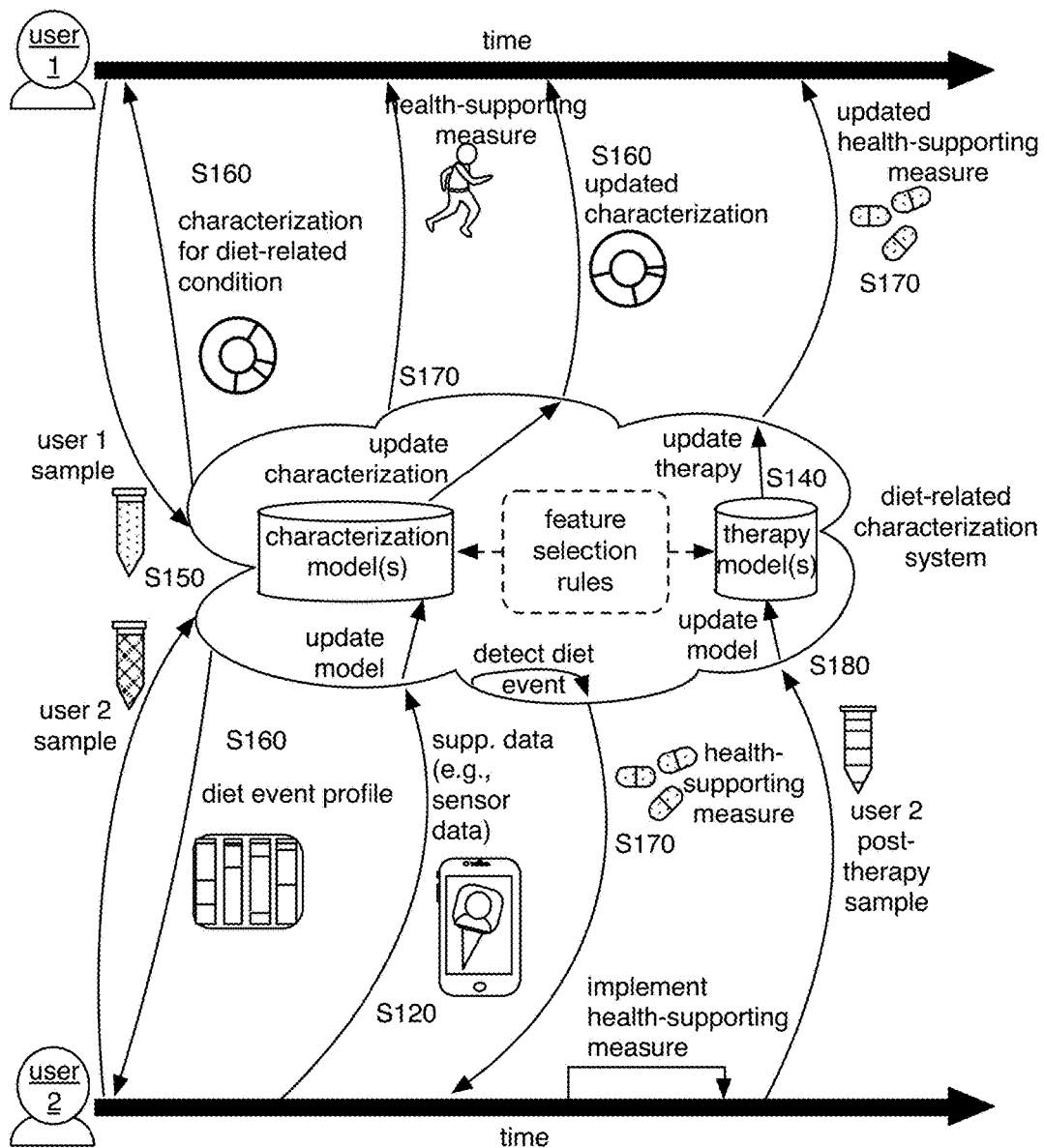
FIG. 7 depicts a schematic representation of variations of an embodiment of the method.

In a variation, as shown in FIG. 7, diet-related characterization can include one or more diet-related (e.g., omnivorous) profiles for the user, where the trigger profile can describe health conditions associated with the diet (e.g., conditions correlated with diet-related factors; conditions indicating future diet-related nutrition conditions; causes; nutrition; etc.) associated with the user (e.g., known to affect the user; predicted to affect the user, such as based on microbiome features, supplementary data, etc.). Diet-related conditions can be associated with (e.g., correlated with, etc.) one or more of: family history, age, gender, weight, height, other demographic characteristics, and/or any other suitable supplementary data. In a specific example, generating a diet-related characterization can include generating a diet profile for the user based on user microbiome features (e.g., and a diet-related condition characterization model), and promoting (e.g., providing) a health-supporting measure operable to improve nutrition associated with the diet profile for the user. In examples, the method 100 can include identifying nutritional gaps for a user based on a corresponding diet-related profile (e.g., for the user, for another user, etc.). In a specific example, the method 100 can include: detecting a diet-related event for the subject based on the diet profile and user supplementary data including at least one of analyte sensor data and location sensor data (e.g., indicating physical activity behaviors; user locations; eating habits; eating locations; mobility behaviors; other behaviors correlated with diet triggers; etc.) collected from a mobile computing device (e.g., smartphone, smart watch, tablet, laptop, etc.) associated with the user; and promoting a health-supporting measure in response to detecting the diet-related event. Additionally or alternatively, detecting diet-related events can be based on any one or more of: microbiome features (e.g., a microbiome composition indicating a a certain nutritional state), supplementary features (e.g., historic medical data for the user, sensor data, nutrition supplementary data, sleep data such as derived through sensor data, etc.), and/or any other suitable features.

In another variation, a diet-related characterization can include a microbiome diversity score (e.g., in relation to microbiome composition, function, etc.) associated with (e.g., correlated with; negatively correlated with; positively correlated with; etc.) a microbiome diversity score correlated with the diet-related condition. In an example, the method 100 can include promoting a nutrition-related health-supporting measure (e.g., probiotics; dietary regimen modifications; etc.) operable to improve the microbiome diversity score for improving a state of the diet-related condition, such as based on a diet-related characterization (e.g., including the microbiome diversity score for the user) and/or nutrition-related supplementary data collected from the user. In examples, the diet-related characterization can include microbiome diversity scores over time (e.g., calculated for a plurality of biological samples of the user collected over time), comparisons to microbiome diversity scores for other users, and/or any other suitable type of microbiome diversity score. However, processing microbiome diversity scores (e.g., determining microbiome diversity scores; using microbiome diversity scores to determine and/or provide health supporting measures; etc.) can be performed in any suitable manner.

Determining a diet-related characterization in Block S160 preferably includes identifying features and/or combinations of features associated with the microbiome composition and/or functional features of the subject, inputting the features into the characterization process, and receiving an output that characterizes the subject as belonging to one or more of: a behavioral group, a gender group, a dietary group, a disease-state group, and any other suitable group capable of being identified by the characterization process. Block S160 can additionally or alternatively include generation of and/or output of a confidence metric associated with the characterization of the subject. For instance, a confidence metric can be derived from the number of features used to generate the characterization, relative weights or rankings of features used to generate the characterization, measures of bias in the characterization process, and/or any other suitable parameter associated with aspects of the characterization process. However, leveraging user microbiome features can be performed in any suitable manner to generate any suitable diet-related characterizations.

In some variations, features extracted from the microbiome dataset of the subject can be supplemented with supplementary features (e.g., extracted from supplementary data collected for the user; such as survey-derived features, medical history-derived features, sensor data, etc.), where such data, the user microbiome data, and/or other suitable data can be used to further refine the characterization process of Block S130, Block S160, and/or other suitable portions of the method 100.

Determining a diet-related characterization preferably includes extracting and applying user microbiome features (e.g., user microbiome composition diversity features; user microbiome functional diversity features; etc.) for the user (e.g., based on a user microbiome dataset), characterization models, and/or other suitable components, such as by employing approaches described in Block S130, and/or by employing any suitable approaches described herein.

Figure 6:
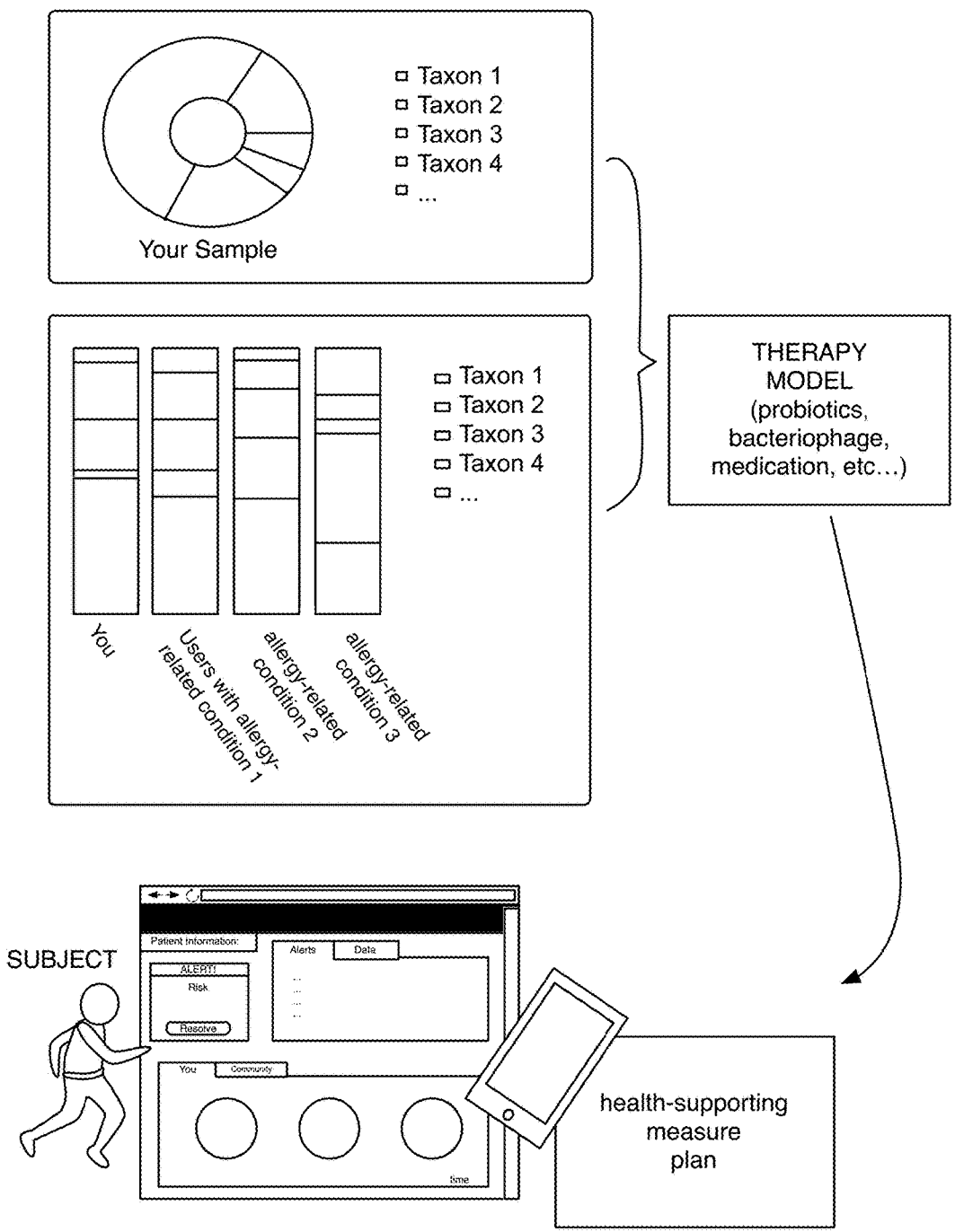
FIG. 6 depicts examples of notification provision.

In variations, as shown in FIG. 6, Block S160 can include presenting diet-related characterizations (e.g., information extracted from the characterizations, etc.), such as an a web interface, patient portal, a mobile application, and/or any other suitable interface, but presentation of diet-related information can be performed in any suitable manner. However, the microbiome dataset of the subject can additionally or alternatively be used in any other suitable manner to enhance the models of the method 100, and Block S160 can be performed in any suitable manner.

3.7 Promoting a Health-Supporting Measure.

Figure 5:
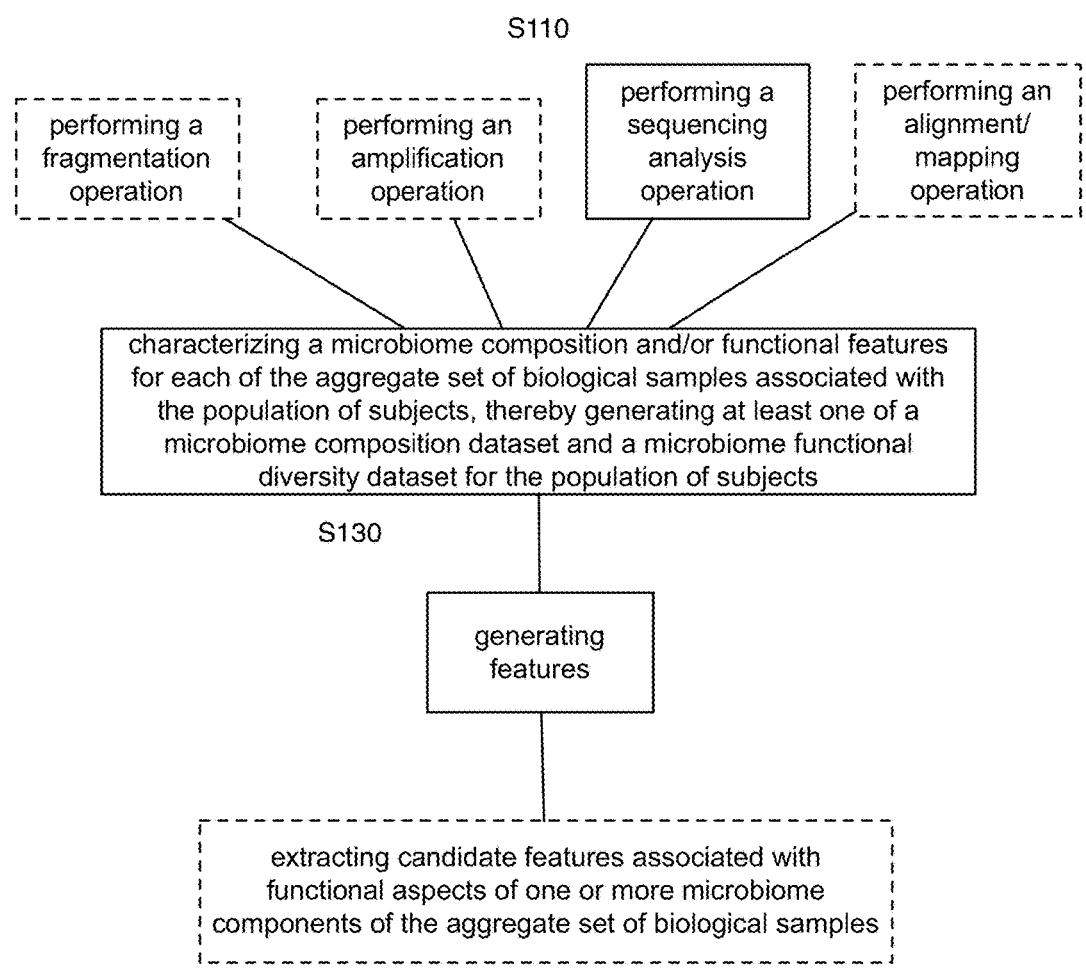
FIG. 5 depicts variations of sample processing in an embodiment of a method.
Figure 9:
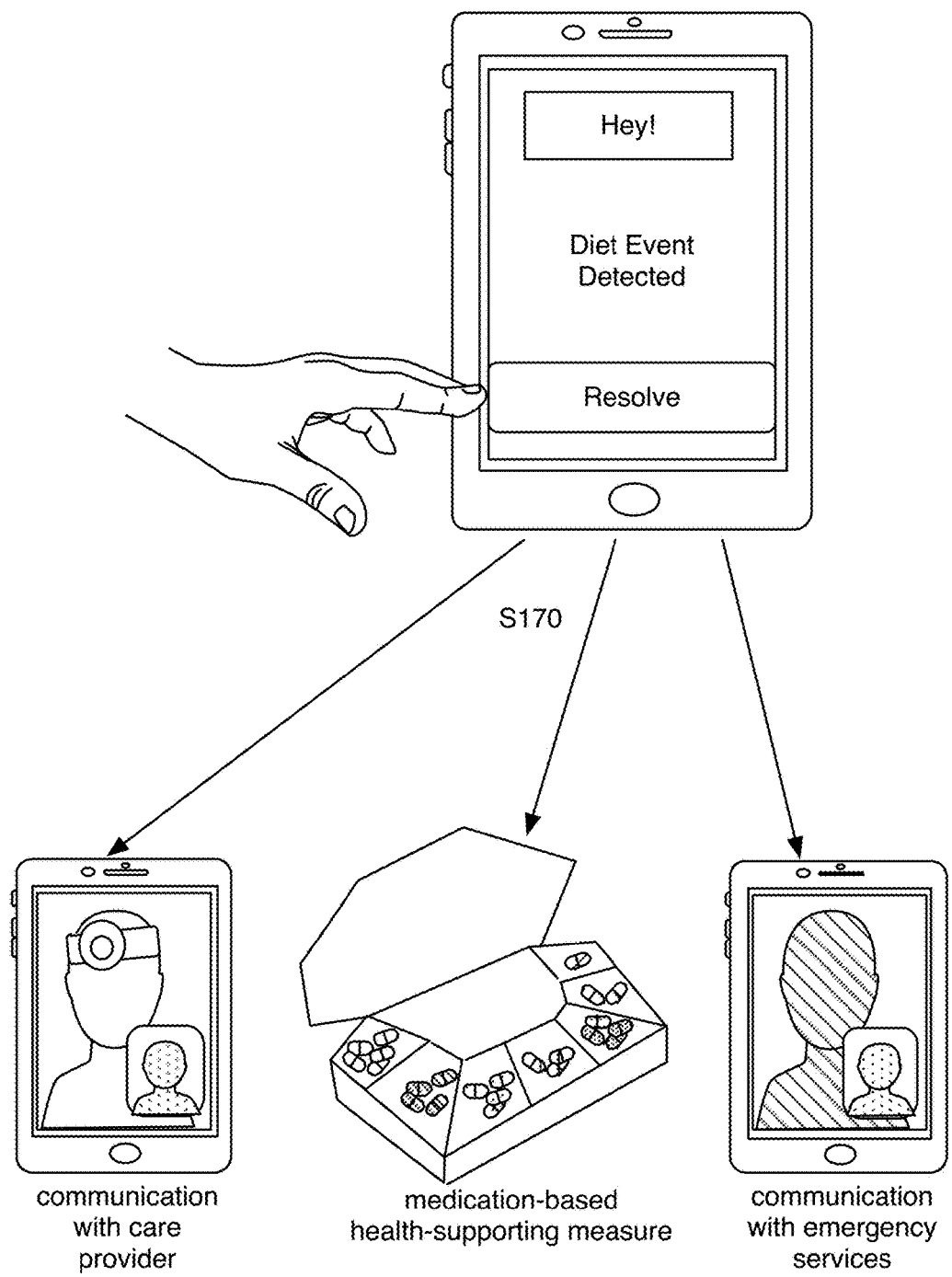
FIG. 9 depicts promoting a health-supporting measure in an embodiment of a method.

As shown in FIG. 9, the method 100 can additionally or alternatively include Block S170, which recites: promoting (e.g., providing, facilitating provision of, etc.) a health-supporting measure for the diet-related condition to the user (e.g., based upon the diet-related characterization and/or a therapy model). Block S170 can function to recommend or provide a personalized health-supporting measure to the subject, in order to shift the microbiome composition and/or functional diversity of a user toward a desired equilibrium state. Block S170 can include provision of a customized health-supporting measure to the subject according to their microbiome composition and functional features, as shown in FIG. 5, where the customized health-supporting measure is a formulation of microorganisms configured to improve health of subjects having the identified characterization. As such, outputs of Block S140 can be used to directly promote a customized health-supporting measure formulation and regimen (e.g., dosage, usage instructions) to the subject based upon a trained therapy model. Additionally or alternatively, therapy provision can include recommendation of available therapeutic measures configured to shift microbiome composition and/or functional features toward a desired state. In variations, health-supporting measures can include any one or more of: consumables, topical therapies (e.g., lotions, ointments, antiseptics, etc.), medication (e.g., diet medications, antihistamines, antibiotics, medication sprays such as nasal sprays, anticholinergic medication, steroid medication, eye drops, leukotriene inhibitors, mast cell inhibitors, diet shots, medications associated with any suitable medication type and/or dosage, etc.), bacteriophages, environmental treatments (e.g., reducing and/or preventing environmental triggers, such as diet-proofing a living space; dehumidifiers; pillow covers; dust reducers; acupuncture; etc.), behavioral modification (e.g., stress-reduction therapies, physical activity-related therapies, etc.), diagnostic procedures, other medical-related procedures, and/or any other suitable therapies associated with diet-related conditions. Consumables can include any one or more of: food and/or beverage items (e.g., probiotic and/or prebiotic food and/or beverage items, etc.), nutritional supplements (e.g., vitamins, minerals, fiber, fatty acids, amino acids, prebiotics, probiotics, etc.), consumable medications, and/or any other suitable therapeutic measure. For example, a combination of commercially available probiotic supplements can include a suitable probiotic therapy for the subject according to an output of the therapy model. In another example, promoting a therapy can include providing, based on the food-related diet characterization, a therapy enabling selective modulation of a microbiome of the user in relation to at least one of a population size of a desired taxon and a desired microbiome function, wherein the therapy is associated with improving a state of an diet-related condition. In another example, the method 100 can include determining a nutritional risk for the user for the diet-related condition based on a diet-related characterization model (e.g., and/or user microbiome features); and promoting the health-supporting measure to the subject based on the nutritional risk.

In a variation, promoting a health-supporting measure can include promoting a diagnostic procedure (e.g., for facilitating detection of diet-related conditions, which can motivate subsequent promotion of other health-supporting measures, such as for modulation of a user microbiome for improving a user health state associated with one or more diet-related conditions; etc.). Diagnostic procedures can include any one or more of: skin prick testing, patch testing, blood testing, challenge testing, performing portions of the method 100, and/or any other suitable procedures for facilitating the detecting (e.g., observing, predicting, etc.) of diet-related conditions. Additionally or alternatively, diagnostic device-related information and/or other suitable diagnostic information can be processed as part of a supplementary dataset (e.g., in relation to Block S120, where such data can be used in determining and/or applying characterization models, therapy models, and/or other suitable models; etc.), and/or collected, used, and/or otherwise processed in relation to any suitable portions of the method 100 (e.g., administering diagnostic procedures for users for monitoring therapy efficacy in relation to Block S180; etc.)

In another variation, Block S170 can include promoting a bacteriophage-based health-supporting measure. In more detail, one or more populations (e.g., in terms of colony forming units) of bacteriophages specific to a certain bacteria (or other microorganism) represented in the subject can be used to down-regulate or otherwise eliminate populations of the certain bacteria. As such, bacteriophage-based therapies can be used to reduce the size(s) of the undesired population(s) of bacteria represented in the subject. Complementarily, bacteriophage-based therapies can be used to increase the relative abundances of bacterial populations not targeted by the bacteriophage(s) used.

In another variation, provision of a health supporting measure in Block S170 can include provision of notifications to a subject regarding the recommended health-supporting measure, other forms of therapy, diet-related characterizations, and/or other suitable diet-related data. In a specific example, providing a therapy to a user can include providing therapy recommendations (e.g., substantially concurrently with providing information derived from an diet-related characterization for a user; etc.) and/or other suitable therapy-related information (e.g., therapy efficacy; comparisons to other individual users, subgroups of users, and/or populations of users; therapy comparisons; historic therapies and/or associated therapy-related information; etc.), such as through presenting notifications at a web interface (e.g., through a user account associated with and identifying a user; etc.). Notifications can be provided to a subject by way of an electronic device (e.g., personal computer, mobile device, tablet, wearable, head-mounted wearable computing device, wrist-mounted wearable computing device, etc.) that executes an application, web interface, and/or messaging client configured for notification provision. In one example, a web interface of a personal computer or laptop associated with a subject can provide access, by the subject, to a user account of the subject, where the user account includes information regarding the user's diet-related characterization, detailed characterization of aspects of the user's microbiome (e.g., in relation to correlations with diet-related conditions; etc.), and/or notifications regarding suggested therapeutic measures (e.g., generated in Blocks S140 and/or S170, etc.). In another example, an application executing at a personal electronic device (e.g., smart phone, smart watch, head-mounted smart device) can be configured to provide notifications (e.g., at a display, haptically, in an auditory manner, etc.) regarding therapy suggestions generated by the therapy model of Block S170. Notifications and/or probiotic therapies can additionally or alternatively be provided directly through an entity associated with a subject (e.g., a caretaker, a spouse, a significant other, a healthcare professional, etc.). In some further variations, notifications can additionally or alternatively be provided to an entity (e.g., healthcare professional) associated with a subject, such as where the entity is able to facilitate provision of the therapy (e.g., by way of prescription, by way of conducting a therapeutic session, through a digital telemedicine session using optical and/or audio sensors of a computing device, etc.). In examples, providing notifications can be performed in response to and/or in any suitable temporal relation to a trigger condition (e.g., a trigger for an diet-related condition). In a specific example, the method 100 can include: determining a risk for an diet-related nutritional state (and/or other suitable diet-related characterizations; etc.) based on one or more user microbiome datasets; detecting an diet-related event (e.g., predicting the historic, current, and/or future presence of an diet-related event, etc.) based on analyzed features and/or supplementary data such as GPS location sensor data indicating a location correlated with the presence of diet-related triggers, other supplementary sensor data, etc.; and providing an diet-related notification (e.g., a warning to the user; recommendations; etc.) and/or other suitable health-supporting measures (e.g., contacting emergency services; contacting an individual associated with the user; facilitating application of therapeutics by appropriate medical devices; etc.) to the user in response to detecting the diet-related event. Promoting diet-related notifications and/or other suitable therapies can, however, be performed in any suitable manner.

3.8 Monitoring Effectiveness of Health-Supporting Measures/Therapies.

As shown in FIG. 7, the method can additionally or alternatively include Block S180, which recites: monitoring effectiveness of the health-supporting measure for the subject, based upon processing biological samples, to assess microbiome composition and/or functional features for the subject at a set of time points associated with the probiotic therapy. Block S180 can function to gather additional data regarding positive effects, negative effects, and/or lack of effectiveness of a probiotic therapy suggested by the therapy model for subjects of a given characterization. Monitoring of a subject during the course of a therapy promoted by the therapy model (e.g., by receiving and analyzing biological samples from the subject throughout therapy, by receiving survey-derived data from the subject throughout therapy) can thus be used to generate a therapy-effectiveness model for each characterization provided by the characterization process of Block S130, and each recommended therapy measure provided in Blocks S140 and S170.

In Block S180, the subject can be prompted to provide additional biological samples at one or more key time points of a therapy regimen that incorporates the therapy, and the additional biological sample(s) can be processed and analyzed (e.g., in a manner similar to that described in relation to Block S120) to generate metrics characterizing modulation of the subject's microbiome composition and/or functional features. For instance, metrics related to one or more of: a change in relative abundance of one or more taxonomic groups represented in the subject's microbiome at an earlier time point, a change in representation of a specific taxonomic group of the subject's microbiome, a ratio between abundance of a first taxonomic group of bacteria and abundance of a second taxonomic group of bacteria of the subject's microbiome, a change in relative abundance of one or more functional families in a subject's microbiome, and any other suitable metrics can be used to assess therapy effectiveness from changes in microbiome composition and/or functional features. Additionally or alternatively, survey-derived data from the subject, pertaining to experiences of the subject while on the therapy (e.g., experienced side effects, personal assessment of improvement, etc.) can be used to determine effectiveness of the therapy in Block S180. For example, the method 100 can include receiving a post-therapy biological sample from the user; collecting a supplementary dataset from the user, where the supplementary dataset describes user adherence to a therapy (e.g., a determined and promoted therapy); generating a post-therapy microbiome characterization of the first user in relation to the diet-related condition based on the diet-related condition characterization model and the post-therapy biological sample; and promoting an updated therapy to the user for the diet-related condition based on the post-therapy microbiome characterization (e.g., based on a comparison between the post-therapy microbiome characterization and a pre-therapy microbiome characterization; etc.) and the user adherence to the therapy (e.g., modifying the therapy based on positive or negative results for the user microbiome in relation to the diet-related condition; etc.). Therapy effectiveness, processing of additional biological samples (e.g., to determine additional diet-related characterizations, therapies, etc.), and/or other suitable aspects associated with continued biological sample collection, processing, and analysis in relation to diet-related conditions can be performed at any suitable time and frequency for generating, updating, and/or otherwise processing models (e.g., characterization models, therapy models, etc.), and/or for any other suitable purpose (e.g., as inputs associated with other portions of the method 100). However, Block S180 can be performed in any suitable manner.

The method 100 can, however, include any other suitable blocks or steps configured to facilitate reception of biological samples from subjects, processing of biological samples from subjects, analyzing data derived from biological samples, and generating models that can be used to provide customized diagnostics and/or probiotic-based therapeutics according to specific microbiome compositions and/or functional features of subjects.

The method 100 and/or system of the embodiments can be embodied and/or implemented at least in part as a machine configured to receive a computer-readable medium storing computer-readable instructions. The instructions can be executed by computer-executable components integrated with the application, applet, host, server, network, website, communication service, communication interface, hardware/firmware/software elements of a patient computer or mobile device, or any suitable combination thereof. Other systems and methods of the embodiments can be embodied and/or implemented at least in part as a machine configured to receive a computer-readable medium storing computer-readable instructions. The instructions can be executed by computer-executable components integrated by computer-executable components integrated with apparatuses and networks of the type described above. The computer-readable medium can be stored on any suitable computer readable media such as RAMs, ROMs, flash memory, EEPROMs, optical devices (CD or DVD), hard drives, floppy drives, or any suitable device. The computer-executable component can be a processor, though any suitable dedicated hardware device can (alternatively or additionally) execute the instructions.

The FIGURES illustrate the architecture, functionality and operation of possible implementations of systems, methods and computer program products according to preferred embodiments, example configurations, and variations thereof. In this regard, each block in the flowchart or block diagrams may represent a module, segment, step, or portion of code, which comprises one or more executable instructions for implementing the specified logical function(s). It should also be noted that, in some alternative implementations, the functions noted in the block can occur out of the order noted in the FIGURES. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

As a person skilled in the art will recognize from the previous detailed description and from the figures and claims, modifications and changes can be made to the embodiments of the invention without departing from the scope of this invention as defined in the following claims.

We claim:
1. A method for characterizing a diet-related condition, the method comprising:
  collecting samples from a set of users, wherein the samples comprise microorganism nucleic acids associated with the diet-related condition;
  generating a microorganism sequence dataset for the set of users based on the microorganism nucleic acids;
  determining microbiome composition diversity features and microbiome functional diversity features for the set of users based on the microorganism sequence dataset;
  collecting supplementary data associated with the diet-related condition for the set of users;
  transforming the supplementary data, the microbiome composition diversity features, and the microbiome functional diversity features into a diet-related characterization model for the diet-related condition;
  generating a diet-related characterization for a user based on the diet-related characterization model; and
  providing a health-supporting measure to the user with the diet-related condition based on the diet-related characterization.

2. The method of claim 1, wherein generating the microorganism sequence dataset comprises:
  identifying a primer type compatible with a genetic target associated with the diet-related condition; and
  generating the microorganism sequence dataset based on the primer type and the microorganism nucleic acids.

3. The method of claim 2, wherein generating the microorganism sequence dataset comprises performing generating at least one of metagenomic and metatranscriptomic libraries with experimental methods by at least one of: a) direct processing of microorganism nucleic acid material and b) processing of fragmented nucleic acids, and performing metagenomics and metatranscriptomics analyses to identify genetic targets associated with the diet-related condition.

4. The method of claim 2, wherein generating the microorganism sequence dataset comprises performing amplification operations, comprising singleplex and multiplex amplifications, using material directly from microorganism nucleic acids and using the primer type compatible with the genetic target associated with the diet-related condition.

5. The method of claim 4, wherein generating the microorganism sequence dataset comprises:
  fragmenting the microorganism nucleic acids; and
  performing multiplex amplification with the fragmented microorganism nucleic acids based on the fragmented microorganism nucleic acids and the identified primer type compatible with the genetic target associated with the diet: related condition.

6. The method of claim 1, wherein providing the health-supporting measure comprises providing, based on the diet-related characterization, a therapy enabling selective modulation of a microbiome of the user in relation to at least one of a population size of a desired taxon and a desired microbiome function, wherein the therapy is associated with improving a state of the diet-related condition.

7. The method of claim 1, wherein generating the diet-related characterization comprises generating the diet-related characterization based on the diet-related characterization model and a set of user microbiome features for the user, wherein the set of user microbiome features are associated with at least one of: presence of a microbiome feature from the set of user microbiome features, absence of the microbiome feature from the set of user microbiome features, relative abundance of different taxonomic groups associated with the diet related condition, a ratio between at least two microbiome features associated with the different taxonomic groups, interactions between the different taxonomic groups, and phylogenetic distance between the different taxonomic groups.

8. The method of claim 1, wherein the diet-related condition comprises at least one of a vegetarian and vegan diet condition and an omnivorous and raw meat diet condition, and wherein the microbiome composition diversity features and the microbiome functional diversity features are associated with at least one of: *Odoribacter splanchnicus* (species), *Alistipes putredinis* (species), *Collinsella aerofaciens* (species), *Parabacteroides distasonis* (species), *Flavonifractor plautii* (species), *Dorea formicigenerans* (species),

*Clostridium* (genus), *Odoribacter* (genus), *Bilophila* (genus), *Parabacteroides* (genus), *Dorea* (genus), *Phascolarctobacterium* (genus), *Anaerostipes* (genus), *Butyricimonas* (genus), *Oscillospira* (genus), Porphyromonadaceae (family), Desulfovibrionaceae (family), Sutterellaceae (family), Acidaminococcaceae (family), Coriobacteriaceae (family), Bifidobacteriaceae (family), Oscillospiraceae (family), Pasteurellaceae (family), Desulfovibrionales (order), Burkholderiales (order), Coriobacteriales (order), Lactobacillales (order), Deltaproteobacteria (class) Betaproteobacteria (class), Bacilli (class), and Proteobacteria_1224 (phylum).

9. The method of claim 8, wherein the microbiome composition diversity features and the microbiome functional diversity features are associated with at least one of: Cell cycle control functions, cell division functions, chromosome partitioning functions, Phosphatidylinositol signaling system functions, and transporter functions.

10. The method of claim 1, wherein the diet-related condition comprises at least one of a low carbohydrate diet condition and an omnivorous and raw meat diet condition, and wherein the microbiome composition diversity features and the microbiome functional diversity features are associated with at least one of: *Blautia luti* (species), *Blautia wexlereae* (species), *Blautia obeum* (species), *Sutterella wadsworthensis* (species), *Bifidobacterium longum* (species), *Collinsella aerofaciens* (species), *Bifidobacterium* (genus), *Roseburia* (genus), *Moryella* (genus), *Odoribacter* (genus), *Bacteroides* (genus), Bifidobacteriaceae (family), Ruminococcaceae (family), Desulfovibrionaceae (family), Clostridiaceae (family), Bacteroidaceae (family), Bifidobacteriales (order), Bacteroidales (order), Desulfovibrionales (order), Clostridiales (order), Bacteroidia (class), Deltaproteobacteria (class), Clostridia (class), Bacteroidetes (phylum), Firmicutes (phylum), and Actinobacteria (phylum).

11. The method of claim 10, wherein the microbiome composition diversity features and the microbiome functional diversity features are associated with at least one of: Metabolism functions, Transport and Catabolism functions, Glycan Biosynthesis and Metabolism functions, Cellular Processes and Signaling functions, Poorly Characterized functions, Environmental Adaptation functions, Translation functions, Neurodegenerative Diseases functions, Huntington's disease functions, MAPK signaling pathway—yeast functions, Lipopolysaccharide biosynthesis proteins functions, Membrane and intracellular structural molecules functions, Cell motility and secretion functions, Penicillin and cephalosporin biosynthesis functions, Pores ion channels functions, D-Alanine metabolism functions, Geraniol degradation functions, Lipoic acid metabolism functions, Nitrogen metabolism functions, Amino acid metabolism functions, Taurine and hypotaurine metabolism functions, Ribosome Biogenesis functions, Peroxisome functions, Thiamine metabolism functions, Biosynthesis and biodegradation of secondary metabolites functions, Aminoacyl-tRNA biosynthesis functions, Plant-pathogen interaction functions, Cellular antigens functions, Type II diabetes mellitus functions, Energy metabolism functions, Citrate cycle (TCA cycle) functions, Cytoskeleton proteins functions, Glycosphingolipid biosynthesis—globo series functions, Photosynthesis functions, Other glycan degradation functions, Drug metabolism—cytochrome P450 functions, Inorganic ion transport and metabolism functions, Photosynthesis proteins functions, Peptidoglycan biosynthesis functions, Protein folding and associated processing functions, Biotin metabolism functions, Aminobenzoate degradation functions, Metabolism of xenobiotics by cytochrome P450 functions, Phosphatidylinositol signaling system functions, Retinol metabolism functions, Nicotinate and nicotinamide metabolism functions, and Polycyclic aromatic hydrocarbon degradation functions.

12. The method of claim 1, wherein the diet-related condition comprises at least one of a low carbohydrate diet condition and a vegetarian and vegan diet condition, and wherein the microbiome composition diversity features and the microbiome functional diversity features are associated with at least one of: *Odoribacter* splanchnicus (species), *Alistipes putredinis* (species), *Flavonifractor plautii* (species), *Phascolarctobacterium faecium* (species), *Bifidobacterium longum* (species), *Parabacteroides distasonis* (species), *Blautia luti* (species), *Sutterella wadsworthensis* (species), *Bacteroides* vulgatus (species), *Bacteroides* finegoldii (species), *Blautia wexlereae* (species), *Blautia obeum* (species), *Bifidobacterium* (genus), *Odoribacter* (genus), *Bilophila* (genus), *Phascolarctobacterium* (genus), *Roseburia* (genus), *Parabacteroides* (genus), *Moryella* (genus), *Intestinimonas* (genus), *Butyricimonas* (genus), *Alistipes* (genus), *Oscillospira* (genus), *Sarcina* (genus), *Flavonifractor* (genus), *Veillonella* (genus), *Clostridium* (genus), *Faecalibacterium* (genus), *Anaerostipes* (genus), *Bacteroides* (genus), *Parasutterella* (genus), Bifidobacteriaceae (family), Desulfovibrionaceae (family), Porphyromonadaceae (family), Sutterellaceae (family), Acidaminococcaceae (family), Rikenellaceae (family), Bacteroidaceae (family), Ruminococcaceae (family), Oscillospiraceae (family), Lactobacillaceae (family), Bifidobacteriales (order), Desulfovibrionales (order), Burkholderiales (order), Clostridiales (order), Bacteroidales (order), Pasteurellales (order), Verrucomicrobiales (order), Selenomonadales (order), Deltaproteobacteria (class), Betaproteobacteria (class), Clostridia (class), Bacteroidia (class), Verrucomicrobiae (class), Negativicutes (class), Proteobacteria (phylum), Firmicutes (phylum), Bacteroidetes (phylum), and Verrucomicrobia (phylum).

13. The method of claim 12, wherein the microbiome composition diversity features and the microbiome functional diversity features are associated with at least one of: Transport and Catabolism functions, Metabolism functions, Excretory System functions, Neurodegenerative Diseases functions, Cancers functions, Endocrine System functions, Cellular Processes and Signaling functions, Glycan Biosynthesis and Metabolism functions, Phosphatidylinositol signaling system functions, Amyotrophic lateral sclerosis (ALS) functions, Huntington's disease functions, D-Alanine metabolism functions, Other transporters functions, Glycosaminoglycan degradation functions, Glycosphingolipid biosynthesis—ganglio series functions, Lipoic acid metabolism functions, Lipopolysaccharide biosynthesis functions, Amino acid metabolism functions, Lipopolysaccharide biosynthesis proteins functions, Glycosphingolipid biosynthesis—globo series functions, Lysosome functions, Bisphenol degradation functions, Penicillin and cephalosporin biosynthesis functions, Ribosome Biogenesis functions, Cell motility and secretion functions, Proximal tubule bicarbonate reclamation functions, Phenylalanine metabolism functions, Peroxisome functions, Pantothenate and CoA biosynthesis functions, Biotin metabolism functions, Sphingolipid metabolism functions, Electron transfer carriers functions, Other glycan degradation functions, Membrane and intracellular structural molecules functions, Ubiquitin system functions, Inorganic ion transport and metabolism functions, Phosphonate and phosphinate metabolism functions, Thiamine metabolism functions, Toluene degradation functions, Renal cell carcinoma functions, Nitrogen metabolism functions, Photosynthesis functions, Photosynthesis proteins functions, Pentose and glucuronate interconversions functions, Drug metabolism—cytochrome P450 functions, Adipocytokine signaling pathway functions, PPAR signaling pathway functions, Cysteine and methionine metabolism functions, Aminoacyl-tRNA biosynthesis functions, Pathways in cancer functions, Type II diabetes mellitus functions, Cellular antigens functions, Pores ion channels functions, Amino acid related enzymes functions, Protein processing in endoplasmic reticulum functions, Metabolism of xenobiotics by cytochrome P450 functions, Linoleic acid metabolism functions.

14. The method of claim 1, wherein the diet-related condition comprises at least one of a gluten-free and dairy-free diet condition and a vegetarian and vegan diet condition, and wherein the microbiome composition diversity features and the microbiome functional diversity features are associated with at least one of: *Collinsella aerofaciens* (species), *Blautia luti* (species), *Bifidobacterium longum* (species), *Alistipes* putredinis (species), *Faecalibacterium prausnitzii* (species), *Flavonifractor* plautii (species), *Streptococcus thermophilus* (species), *Bacteroides* vulgatus (species), *Subdoligranulum variabile* (species), *Parabacteroides distasonis* (species), *Barnesiella intestinihominis* (species), *Roseburia hominis* (species), *Bacteroides* thetaiotaomicron (species), *Odoribacter* splanchnicus (species), *Bacteroides* caccae (species), *Parabacteroides* merdae (species), *Roseburia inulinivorans* (species), *Bacteroides* nordii (species), *Blautia* faecis (species), *Erysipelatoclostridium ramosum* (species), *Bacteroides fragilis* (species), *Blautia* wexlereae (species), *Blautia* obeum (species), *Bifidobacterium* (genus), *Moryella* (genus), *Dorea* (genus), *Collinsella* (genus), *Lachnospira* (genus), *Oscillospira* (genus), *Subdoligranulum* (genus), *Streptococcus* (genus), *Sutterella* (genus), *Pseudobutyrivibrio* (genus), *Intestinimonas* (genus), *Clostridium* (genus), *Dialister* (genus), *Lactobacillus* (genus), *Phascolarctobacterium* (genus), *Bacteroides* (genus), *Faecalibacterium* (genus), *Marvinbryantia* (genus), *Hespellia* (genus), *Roseburia* (genus), *Acetitomaculum* (genus), *Intestinibacter* (genus), *Finegoldia*_150022 (genus), Bifidobacteriaceae (family), Coriobacteriaceae (family), Streptococcaceae (family), Veillonellaceae (family), Prevotellaceae (family), Ruminococcaceae (family), Acidaminococcaceae (family), Enterobacteriaceae (family), Bacteroidaceae (family), Lactobacillaceae (family), Desulfovibrionaceae (family), Clostridiales Family XI. Incertae Sedis (family), Peptostreptococcaceae (family), Erysipelotrichaceae (family), Bifidobacteriales (order), Selenomonadales (order), Coriobacteriales (order), Enterobacteriales (order), Desulfovibrionales (order), Bacteroidales (order), Erysipelotrichales (order), Lactobacillales (order), Actino-bacteria (class), Negativicutes (class), Deltaproteobacteria (class), Bacteroidia (class), Gammaproteobacteria (class), Erysipelotrichia (class), Bacilli (class), Betaproteobacteria (class), Actinobacteria (phylum), Bacteroidetes (phylum), Firmicutes (phylum), and Euryarchaeota (phylum).

15. The method of claim 14, wherein the microbiome composition diversity features and the microbiome functional diversity features are associated with at least one of: Metabolism functions, Carbohydrate Metabolism functions, Enzyme Families functions, Translation functions, Genetic Information Processing functions, Environmental Adaptation functions, Immune System Diseases functions, Lipid Metabolism functions, Transport and Catabolism functions, Energy Metabolism functions, Xenobiotics Biodegradation and Metabolism functions, Replication and Repair functions, Nucleotide Metabolism functions, Signaling Molecules and Interaction functions, Neurodegenerative Diseases functions, Cell Motility functions, Poorly Characterized functions, Metabolism of Other Amino Acids functions, Glycan Biosynthesis and Metabolism functions, Cellular Processes and Signaling functions, Nervous System functions, ABC transporters functions, Alanine, aspartate and glutamate metabolism functions, Amino acid metabolism functions, Amino acid related enzymes functions, Amino sugar and nucleotide sugar metabolism functions, Aminoacyl-tRNA biosynthesis functions, Aminobenzoate degradation functions, Bacterial chemotaxis functions, Base excision repair functions, Benzoate degradation functions, Biosynthesis and biodegradation of secondary metabolites functions, Butanoate metabolism functions, Carbohydrate digestion and absorption functions, Carbohydrate metabolism functions, Carbon fixation in photosynthetic organisms functions, Carbon fixation pathways in prokaryotes functions, Cellular antigens functions, Chromosome functions, Citrate cycle (TCA cycle) functions, Cysteine and methionine metabolism functions, Cytoskeleton proteins functions, D-Alanine metabolism functions, DNA repair and recombination proteins functions, DNA replication functions, DNA replication proteins functions, Energy metabolism functions, Epithelial cell signaling in *Helicobacter pylori* infection functions, Ethylbenzene degradation functions, Fatty acid biosynthesis functions, Fatty acid metabolism functions, Fructose and mannose metabolism functions, Galactose metabolism functions, General function prediction only functions, Geraniol degradation functions, Glutamatergic synapse functions, Glutathione metabolism functions, Glycerophospholipid metabolism functions, Glycosphingolipid biosynthesis—globo series functions, Glyoxylate and dicarboxylate metabolism functions, Histidine metabolism functions, Homologous recombination functions, Huntington's disease functions, Inositol phosphate metabolism functions, Ion channels functions, Limonene and pinene degradation functions, Lipid biosynthesis proteins functions, Lipid metabolism functions, Lipoic acid metabolism functions, Lipopolysaccharide biosynthesis proteins functions, Lysine biosynthesis functions, Lysine degradation functions, MAPK signaling pathway—yeast functions, Membrane and intracellular structural molecules functions, Mismatch repair functions, Naphthalene degradation functions, Nicotinate and nicotinamide metabolism functions, Nitrogen metabolism functions, Nucleotide excision repair functions, Nucleotide metabolism functions, Other glycan degradation functions, Other ion-coupled transporters functions, Other transporters functions, Others functions, Oxidative phosphorylation functions, Penicillin and cephalosporin biosynthesis functions, Pentose and glucuronate interconversions functions, Pentose phosphate pathway functions, Peptidases functions, Peptidoglycan biosynthesis functions, Peroxisome functions, Phosphonate and phosphinate metabolism functions, Photosynthesis functions, Plant-pathogen interaction functions, Polycyclic aromatic hydrocarbon degradation functions, Polyketide sugar unit biosynthesis functions, Pores ion channels functions, Primary immunodeficiency functions, Propanoate metabolism functions, Protein export functions, Protein kinases functions, Purine metabolism functions, Pyrimidine metabolism functions, Pyruvate metabolism functions, RNA polymerase functions, RNA transport functions, Replication, recombination and repair proteins functions, Restriction enzyme functions, Riboflavin metabolism functions, Ribosome functions, Ribosome Biogenesis functions, Ribosome biogenesis in eukaryotes functions, Secretion system functions, Selenocompound metabolism functions, Sphingolipid metabolism functions, Streptomycin biosynthesis functions, Sulfur metabolism functions, Taurine and hypotaurine metabolism functions, Terpenoid backbone biosynthesis functions, Tetracycline biosynthesis functions, Thiamine metabolism functions, Transcription factors functions, Transcription machinery functions, Translation factors functions, Translation proteins functions, Tryptophan metabolism functions, Tuberculosis functions, Type I diabetes mellitus functions, Type II diabetes mellitus functions, Valine, leucine and isoleucine degradation functions, and beta-Alanine metabolism functions.

16. The method of claim 1, wherein the diet-related condition comprises at least one of a gluten-free and dairy-free diet condition and a vegetarian diet condition, and wherein the microbiome composition diversity features and the microbiome functional diversity features are associated with at least one of: *Flavonifractor* plautii (species), *Bifidobacterium longum* (species), *Parabacteroides distasonis* (species), *Blautia luti* (species), *Bacteroides* vulgatus (species), *Adlercreutzia equolifaciens* (species), *Odoribacter* splanchnicus (species), *Dialister* propionicifaciens (species), *Streptococcus thermophilus* (species), *Collinsella aerofaciens* (species), *Blautia* wexlereae (species), *Blautia* obeum (species), *Bifidobacterium* (genus), *Moryella* (genus), *Intestinimonas* (genus), *Oscillospira* (genus), *Dialister* (genus), *Odoribacter* (genus), *Bilophila* (genus), *Bacteroides* (genus), *Parabacteroides* (genus), *Faecalibacterium* (genus), *Parasutterella* (genus), *Adlercreutzia* (genus), *Streptococcus* (genus), *Butyricimonas* (genus), *Hespellia* (genus), *Clostridium* (genus), *Alistipes* (genus), Bifidobacteriaceae (family), Veillonellaceae (family), Oscillospiraceae (family), Porphyromonadaceae (family), Streptococcaceae (family), Bacteroidaceae (family), Clostridiales Family XIII. Incertae Sedis (family), Desulfovibrionaceae (family), Ruminococcaceae (family), Sutterellaceae (family), Lactobacillaceae (family), Rikenellaceae (family), Bifidobacteriales (order), Desulfovibrionales (order), Bacteroidales (order), Burkholderiales (order), Clostridiales (order), Selenomonadales (order), Actinobacteria (class), Deltaproteobacteria (class), Bacteroidia (class), Clostridia (class), Betaproteobacteria (class), Negativicutes (class), Actinobacteria (phylum), Bacteroidetes (phylum), Firmicutes (phylum), and Proteobacteria (phylum).

17. The method of claim 16, wherein the microbiome composition diversity features and the microbiome functional diversity features are associated with at least one of: Metabolism functions, Carbohydrate Metabolism functions, Translation functions, Genetic Information Processing functions, Transport and Catabolism functions, Neurodegenerative Diseases functions, Lipid Metabolism functions, Xenobiotics Biodegradation and Metabolism functions, Nervous System functions, Endocrine System functions, Energy Metabolism functions, Amino acid metabolism functions, Amino acid related enzymes functions, Aminoacyl-tRNA biosynthesis functions, Aminobenzoate degradation functions, Amyotrophic lateral sclerosis (ALS) functions, Ascorbate and aldarate metabolism functions, Biosynthesis and biodegradation of secondary metabolites functions, Bisphenol degradation functions, Butanoate metabolism functions, Carbohydrate metabolism functions, Carbon fixation pathways in prokaryotes functions, Cellular antigens functions, Chromosome functions, Citrate cycle (TCA cycle) functions, Cysteine and methionine metabolism functions, D-Alanine metabolism functions, Electron transfer carriers functions, Energy metabolism functions, Fructose and mannose metabolism functions, Geraniol degradation functions, Glutamatergic synapse functions, Glycerophospholipid metabolism functions, Glycosaminoglycan degradation functions, Glycosphingolipid biosynthesis—ganglio series functions, Glycosphingolipid biosynthesis—globo series functions, Glyoxylate and dicarboxylate metabolism functions, Huntington's disease functions, Inositol phosphate metabolism functions, Lipoic acid metabolism functions, Lipopolysaccharide biosynthesis functions, Lipopolysaccharide biosynthesis proteins functions, Lysosome functions, Membrane and intracellular structural molecules functions, Naphthalene degradation functions, Nicotinate and nicotinamide metabolism functions, Nitrogen metabolism functions, Other glycan degradation functions, Other transporters functions, Others functions, Oxidative phosphorylation functions, PPAR signaling pathway functions, Penicillin and cephalosporin biosynthesis functions, Pentose and glucuronate interconversions functions, Peptidoglycan biosynthesis functions, Peroxisome functions, Phenylalanine metabolism functions, Phosphatidylinositol signaling system functions, Phosphonate and phosphinate metabolism functions, Photosynthesis functions, Photosynthesis proteins functions, Pores ion channels functions, Protein processing in endoplasmic reticulum functions, Proximal tubule bicarbonate reclamation functions, Pyruvate metabolism functions, RNA polymerase functions, Replication, recombination and repair proteins functions, Ribosome functions, Ribosome Biogenesis functions, Sphingolipid metabolism functions, Terpenoid backbone biosynthesis functions, Thiamine metabolism functions, Transcription machinery functions, Translation proteins functions, Type I diabetes mellitus functions, Type II diabetes mellitus functions.

18. The method of claim 1, wherein the diet-related condition comprises a diabetes-associated condition, and wherein the microbiome composition diversity features and the microbiome functional diversity features are associated with at least one of: Acidobacteria (phylum), Actinobacteria (phylum), Bacteroidetes (phylum), Basidiomycota (phylum), *Candidatus* Saccharibacteria (phylum), Chloroflexi (phylum), Cyanobacteria (phylum), *Deinococcus-Thermus* (phylum), Euryarchaeota (phylum), Fibrobacteres (phylum), Firmicutes (phylum), Fusobacteria (phylum), Gemmatimonadetes (phylum), Lentisphaerae (phylum), Planctomycetes (phylum), Proteobacteria (phylum), Spirochaetes (phylum), Streptophyta (phylum), Synergistetes (phylum), Tenericutes (phylum), Verrucomicrobia (phylum), Acidobacteriia (class), Actinobacteria (class), Alphaproteobacteria (class), Anaerolineae (class), Bacilli (class), Bacteroidia (class), Betaproteobacteria (class), Clostridia (class), Cytophagia (class), Deinococci (class), Deltaproteobacteria (class), Epsilonproteobacteria (class), Erysipelotrichia (class), Exobasidiomycetes (class), Fibrobacteria (class), Flavobacteriia (class), Fusobacteriia (class), Gammaproteobacteria (class), Gemmatimonadetes (class), Lentisphaeria (class), Methanobacteria (class), Methanomicrobia (class), Mollicutes (class), Negativicutes (class), Opitutae (class), Planctomycetia (class), Spartobacteria (class), Sphingobacteriia (class), Spirochaetia (class), Synergistia (class), Thermomicrobia (class), Verrucomicrobiae (class), Acidimicrobiales (order), Actinomycetales (order), Aeromonadales (order), Anaerolineales (order), Anaeroplasmatales (order), Bacillales (order), Bacteroidales (order), Bifidobacteriales (order), Burkholderiales (order), Campylobacterales (order), Cardiobacteriales (order), Caulobacterales (order), Clostridiales (order), Coriobacteriales (order), Cytophagales (order), Deinococcales (order), Desulfovibrionales (order), Enterobacteriales (order), Erysipelotrichales (order), Fibrobacterales (order), Flavobacteriales (order), Fusobacteriales (order), Gemmatimonadales (order), Hydrogenophilales (order), Lactobacillales (order), Malasseziales (order), Methanobacteriales (order), Mycoplasmatales (order), Myxococcales (order), Neisseriales (order), Oceanospirillales (order), Pasteurellales (order), Planctomycetales (order), Pleurocapsales (order), Pseudomonadales (order), Puniceicoccales (order), Rhizobiales (order), Rhodobacterales (order), Rhodocyclales (order), Rhodospirillales (order), Selenomonadales (order), Solanales (order), Solirubrobacterales (order), Sphingobacteriales (order), Sphingomonadales (order), Spirochaetales (order), Synergistales (order), Thermales (order), Thermoanaerobacterales (order), Verrucomicrobiales (order), Xanthomonadales (order), Acetobacteraceae (family), Acidaminococcaceae (family), Actinomycetaceae (family), Aerococcaceae (family), Aeromonadaceae (family), Alcaligenaceae (family), Anaerolineaceae (family), Anaeroplasmataceae (family), Aurantimonadaceae (family), Bacillaceae (family), Bacteroidaceae (family), Beijerinckiaceae (family), Bifidobacteriaceae (family), Bradyrhizobiaceae (family), Brevibacteriaceae (family), Brucellaceae (family), Burkholderiaceae (family), Caldicoprobacteraceae (family), Campylobacteraceae (family), Cardiobacteriaceae (family), Carnobacteriaceae (family), Catabacteriaceae (family), Caulobacteraceae (family), Cellulomonadaceae (family), Christensenellaceae (family), Clostridiaceae (family), Clostridiales Family XI. Incertae Sedis (family), Clostridiales Family XIII. Incertae Sedis (family), Comamonadaceae (family), Coriobacteriaceae (family), Corynebacteriaceae (family), Cytophagaceae (family), Deinococcaceae (family), Dermabacteraceae (family), Dermacoccaceae (family), Desulfovibrionaceae (family), Dietziaceae (family), Enterobacteriaceae (family), Enterococcaceae (family), Erysipelotrichaceae (family), Erythrobacteraceae (family), Eubacteriaceae (family), Fibrobacteraceae (family), Flavobacteriaceae (family), Fusobacteriaceae (family), Geodermatophilaceae (family), Halomonadaceae (family), Hydrogenophilaceae (family), Hyphomicrobiaceae (family), Iamiaceae (family), Intrasporangiaceae (family), Lachnospiraceae (family), Lactobacillaceae (family), Leptotrichiaceae (family), Leuconostocaceae (family), Malasseziaceae (family), Methanobacteriaceae (family), Methylobacteriaceae (family), Microbacteriaceae (family), Micrococcaceae (family), Moraxellaceae (family), Mycobacteriaceae (family), Mycoplasmataceae (family), Neisseriaceae (family), Nocardiaceae (family), Nocardioidaceae (family), Oscillospiraceae (family), Oxalobacteraceae (family), Pasteurellaceae (family), Patulibacteraceae (family), Peptococcaceae (family), Peptostreptococcaceae (family), Phyllobacteriaceae (family), Planctomycetaceae (family), Planococcaceae (family), Polyangiaceae (family), Porphyromonadaceae (family), Prevotellaceae (family), Promicromonosporaceae (family), Propionibacteriaceae (family), Pseudomonadaceae (family), Pseudonocardiaceae (family), Rhizobiaceae (family), Rhodobacteraceae (family), Rhodocyclaceae (family), Rhodospirillaceae (family), Rikenellaceae (family), Ruminococcaceae (family), Solanaceae (family), Solirubrobacteraceae (family), Sphingobacteriaceae (family), Sphingomonadaceae (family), Staphylococcaceae (family), Streptococcaceae (family), Streptomycetaceae (family), Succinivibrionaceae (family), Sutterellaceae (family), Synergistaceae (family), Thermaceae (family), Thermoanaerobacteraceae (family), Veillonellaceae (family), Verrucomicrobiaceae (family), Victivallaceae (family), Xanthobacteraceae (family), Xanthomonadaceae (family), *Abiotrophia* (genus), *Acetanaerobacterium* (genus), *Acetitomaculum* (genus), *Achromobacter* (genus), *Acidaminococcus* (genus), *Acidiphilium* (genus), *Acinetobacter* (genus), *Actinobacillus* (genus), *Actinobaculum* (genus), *Actinomyces* (genus), *Adlercreutzia* (genus), *Aerococcus* (genus), *Aeromicrobium* (genus), *Aggregatibacter* (genus), *Akkermansia* (genus), *Albidovulum* (genus), *Alistipes* (genus), *Alkanindiges* (genus), *Allisonella* (genus), *Alloiococcus* (genus), *Alloprevotella* (genus), *Alloscardovia* (genus), *Altererythrobacter* (genus), *Alysiella* (genus), *Amaricoccus* (genus), *Aminobacter* (genus), *Anaerobacter* (genus), *Anaerococcus* (genus), *Anaerofilum* (genus), *Anaerofustis* (genus), *Anaeroglobus* (genus), *Anaeroplasma* (genus), *Anaerosporobacter* (genus), *Anaerostipes* (genus), *Anaerotruncus* (genus), *Anaerovorax* (genus), *Aquabacterium* (genus), *Aquipuribacter* (genus), *Arcanobacterium* (genus), *Arthrobacter* (genus), *Asaccharospora* (genus), *Asteroleplasma* (genus), *Atopobium* (genus), *Aureimonas* (genus), *Bacillus* (genus), *Bacteroides* (genus), *Barnesiella* (genus), *Bergeyella* (genus), *Bifidobacterium* (genus), *Bilophila* (genus), *Blastocatella* (genus), *Blastococcus* (genus), *Blautia* (genus), *Bosea* (genus), *Brachybacterium* (genus), *Bradyrhizobium* (genus), *Brevibacterium* (genus), *Brevundimonas* (genus), *Brooklawnia* (genus), *Burkholderia* (genus), *Butyricicoccus* (genus), *Butyricimonas* (genus), *Butyrivibrio* (genus), *Caldicoprobacter* (genus), *Campylobacter* (genus), *Candidatus Methanomethylophilus* (genus), *Candidatus Saccharimonas* (genus), *Candidatus Soleaferrea* (genus), *Candidatus Stoquefichus* (genus), *Capnocytophaga* (genus), *Cardiobacterium* (genus), *Catabacter* (genus), *Catenibacterium* (genus), *Catonella* (genus), *Caulobacter* (genus), *Cellulomonas* (genus), *Centipeda* (genus), *Chitinophaga* (genus), *Christensenella* (genus), *Chryseobacterium* (genus), *Chthoniobacter* (genus), *Citrobacter* (genus), *Cloacibacillus* (genus), *Cloacibacterium* (genus), *Clostridium* (genus), *Cobetia* (genus), *Collinsella* (genus), *Comamonas* (genus), *Coprobacillus* (genus), *Coprobacter* (genus), *Corynebacterium* (genus), *Cronobacter* (genus), *Curtobacterium* (genus), *Defluviimonas* (genus), *Deinococcus* (genus), *Delftia* (genus), *Dermabacter* (genus), *Desulfovibrio* (genus), *Devosia* (genus), *Dialister* (genus), *Dielma* (genus), *Dietzia* (genus), *Dolosigranulum* (genus), *Dorea* (genus), *Eggerthella* (genus), *Eikenella* (genus), *Eisenbergiella* (genus), *Enterobacter* (genus), *Enterococcus* (genus), *Enterorhabdus* (genus), *Epulopiscium* (genus), *Eremococcus* (genus), *Erysipelatoclostridium* (genus), *Eubacterium* (genus), *Facklamia* (genus), *Faecalibacterium* (genus), *Fastidiosipila* (genus), *Ferruginibacter* (genus), *Fibrobacter* (genus), *Filifactor* (genus), *Finegoldia* (genus), *Flavobacterium* (genus), *Flavonifractor* (genus), *Frigoribacterium* (genus), *Fusicatenibacter* (genus), *Fusobacterium* (genus), *Gallicola* (genus), *Gardnerella* (genus), *Gelria* (genus), *Gemella* (genus), *Geobacillus* (genus), *Globicatella* (genus), *Gordonibacter* (genus), *Granulicatella* (genus), *Haematobacter* (genus), *Haemophilus* (genus), *Hafnia* (genus), *Helcococcus* (genus), *Herbaspirillum* (genus), *Herbiconiux* (genus), *Hespellia* (genus), *Holdemania* (genus), *Howardella* (genus), *Hydrogenoanaerobacterium* (genus), *Hydrogenophilus* (genus), *Hymenobacter* (genus), *Iamia* (genus), *Intestinibacter* (genus), *Intestinimonas* (genus), *Janibacter* (genus), *Jatrophihabitans* (genus), *Johnsonella* (genus), *Jonquetella* (genus), *Kingella* (genus), *Klebsiella* (genus), *Kluyvera* (genus), *Knoellia* (genus), *Kocuria* (genus), *Kytococcus* (genus), *Lachnoanaerobaculum* (genus), *Blautia* sp. YHC-4 (species), *Flavonifractor plautii* (species), *Faecalibacterium prausnitzii* (species), *Parabacteroides distasonis* (species), *Blautia luti* (species), *Blautia wexlerae* (species), *Blautia obeum* (species), *Bacteroides uniformis* (species), *Bacteroides finegoldii* (species), *Bacteroides fragilis* (species), *Bacteroides vulgatus* (species), *Subdoligranulum variabile*

(species), *Kluyvera* (genus), *Bilophila* (genus), *Moryella* (genus), *Faecalibacterium* (genus), *Subdoligranulum* (genus), *Bacteroides* (genus), *Roseburia* (genus), *Enterobacter* (genus), *Eggerthella* (genus), *Parabacteroides* (genus), *Intestinibacter* (genus), *Anaerotruncus* (genus), *Marvinbryantia* (genus), *Erysipelatoclostridium* (genus), *Dorea* (genus), *Sarcina* (genus), *Akkermansia* (genus), *Anaerostipes* (genus), *Megasphaera* (genus), *Lachnospira* (genus), Enterobacteriaceae (family), Ruminococcaceae (family), Desulfovibrionaceae (family), Bacteroidaceae (family), Lactobacillaceae (family), Porphyromonadaceae (family), Oscillospiraceae (family), Peptostreptococcaceae (family), Verrucomicrobiaceae (family), Enterobacteriales (order), Clostridiales (order), Bacteroidales (order), Desulfovibrionales (order), Verrucomicrobiales (order), Erysipelotrichales (order), Selenomonadales (order), Gammaproteobacteria (class), Clostridia (class), Bacteroidia (class), Deltaproteobacteria (class), Verrucomicrobiae (class), Erysipelotrichia (class), Negativicutes (class), Firmicutes (phylum), and Bacteroidetes (phylum) and Proteobacteria (phylum) and Verrucomicrobia (phylum).

19. The method of claim 18, wherein the microbiome composition diversity features and the microbiome functional diversity features are associated with at least one of: Carbohydrate transport and metabolism functions, Environmental Adaptation functions, Poorly Characterized functions, Signaling Molecules and Interaction functions, Metabolism functions, Transport and Catabolism functions, Cell Motility functions, Glycan Biosynthesis and Metabolism functions, Cellular Processes and Signaling functions, Metabolism of Other Amino Acids functions, Xenobiotics Biodegradation and Metabolism functions, Translation functions, Neurodegenerative Diseases functions, Infectious Diseases functions, Amino Acid Metabolism functions, Transcription functions, Digestive System functions, Replication and Repair functions, Protein folding and associated processing functions, Plant-pathogen interaction functions, Amino acid metabolism functions, Nitrogen metabolism functions, Geraniol degradation functions, Inorganic ion transport and metabolism functions, Penicillin and cephalosporin biosynthesis functions, Pores ion channels functions, Lipoic acid metabolism functions, Lipopolysaccharide biosynthesis proteins functions, Vitamin metabolism functions, Membrane and intracellular structural molecules functions, Huntington's disease functions, Ribosome Biogenesis functions, Ion channels functions, Cytoskeleton proteins functions, Inositol phosphate metabolism functions, Biotin metabolism functions, Other ion-coupled transporters functions, Cellular antigens functions, Bacterial chemotaxis functions, Taurine and hypotaurine metabolism functions, Function unknown functions, Phosphatidylinositol signaling system functions, Glutathione metabolism functions, Chromosome functions, Glycosphingolipid biosynthesis—ganglio series functions, Butirosin and neomycin biosynthesis functions, Polycyclic aromatic hydrocarbon degradation functions, Glycosaminoglycan degradation functions, Folate biosynthesis functions, beta-Alanine metabolism functions, Aminoacyl-tRNA biosynthesis functions, Cell motility and secretion functions, Tuberculosis functions, Lysosome functions, Thiamine metabolism functions, Selenocompound metabolism functions, Photosynthesis functions, Photosynthesis proteins functions, Glycosyltransferases functions, Citrate cycle (TCA cycle) functions, Others functions, Tryptophan metabolism functions, Oxidative phosphorylation functions, Nucleotide metabolism functions, Bacterial toxins functions, Aminobenzoate degradation functions, Phenylalanine, tyrosine and tryptophan biosynthesis functions, Sporulation functions, Terpenoid backbone biosynthesis functions, Pantothenate and CoA biosynthesis functions, Translation proteins functions, Peptidoglycan biosynthesis functions, Glycerophospholipid metabolism functions, Peroxisome functions, Amino acid related enzymes functions, RNA transport functions, Cysteine and methionine metabolism functions, Lysine biosynthesis functions, Biosynthesis of ansamycins functions, Fatty acid metabolism functions, Drug metabolism—cytochrome P450 functions, Glycine, serine and threonine metabolism functions, Ribosome functions, Homologous recombination functions, Nicotinate and nicotinamide metabolism functions, Glyoxylate and dicarboxylate metabolism functions, Metabolism of xenobiotics by cytochrome P450 functions, Lysine degradation functions, Starch and sucrose metabolism functions, Lipid metabolism functions, Valine, leucine and isoleucine degradation functions, Biosynthesis of unsaturated fatty acids functions, Carbon fixation pathways in prokaryotes functions, Biosynthesis and biodegradation of secondary metabolites functions, Insulin signaling pathway functions, Phosphotransferase system (PTS) functions, Type II diabetes mellitus functions, Bacterial secretion system functions, Ribosome biogenesis in eukaryotes functions, Glycolysis/Gluconeogenesis functions, Retinol metabolism functions, Valine, leucine and isoleucine biosynthesis functions, Amino sugar and nucleotide sugar metabolism functions, Pyrimidine metabolism functions, Mismatch repair functions, General function prediction only functions, Propanoate metabolism functions, Naphthalene degradation functions, Limonene and pinene degradation functions, Translation factors functions, Methane metabolism functions, Pentose and glucuronate interconversions functions, Type I diabetes mellitus functions and RNA polymerase functions.

20. The method of claim 19, wherein the microbiome composition diversity features and the microbiome functional diversity features are associated with a concordance score between two treatments, and wherein the concordance score comprises at least one of: relative abundance information, presence and absence combined information, functional information, and microorganism feature information.

21. The method of claim 20, wherein the two treatments comprise a first treatment comprising a diabetes type 2 condition and control, and a second treatment comprising diet style conditions and control, wherein each condition and control can be associated with at least one of the following: halal, kosher, no red meat, omnivore, vegan, vegetarian, pescetarian, paleo, low carb, dairy free, gluten free and raw, and wherein the concordance score is obtained for each analysis.

22. The method of claim 21, wherein the concordance score is used for at least one of diagnostics and therapy determination in association with user personalized diagnostics and treatment processes.

23. The method of claim 1, wherein the diet-related condition comprises a dietary condition associated with microorganisms that are lactose and fermented food-tolerant, and wherein the microbiome composition diversity features and the microbiome functional diversity features are associated with at least one of: Acidobacteria (phylum), Acidobacteria (phylum), Acidobacteria (phylum), Actinobacteria (phylum), Actinobacteria (phylum), Bacteroidetes (phylum), Bacteroidetes (phylum), Bacteroidetes (phylum), Candidatus Saccharibacteria (phylum), Candidatus Saccharibacteria (phylum site), Cyanobacteria (phylum), Cyanobacteria (phylum), Cyanobacteria (phylum), Euryarchaeota (phylum), Euryarchaeota (phylum), Fibrobacteres (phylum), Firmicutes (phylum), Fusobacteria (phylum), Fusobacteria (phylum), Fusobacteria (phylum), Fusobacteria (phylum), Lentisphaerae (phylum), Proteobacteria (phylum), Proteobacteria (phylum), Spirochaetes (phylum), Spirochaetes (phylum), Streptophyta (phylum), Synergistetes (phylum), Synergistetes (phylum), Tenericutes (phylum), Tenericutes (phylum), Verrucomicrobia (phylum), Acidobacteriia (class), Acidobacteriia (class), Acidobacteriia (class), Actinobacteria (class), Actinobacteria (class), Alphaproteobacteria (class), Alphaproteobacteria (class), Alphaproteobacteria (class), Alphaproteobacteria (class), Bacilli (class), Bacteroidia (class), Bacteroidia (class), Bacteroidia (class), Betaproteobacteria (class), Betaproteobacteria (class), Betaproteobacteria (class), Betaproteobacteria (class), Clostridia (class), Clostridia (class), Clostridia (class), Cytophagia (class), Deltaproteobacteria (class), Deltaproteobacteria (class), Epsilonproteobacteria (class), Epsilonproteobacteria (class), Epsilonproteobacteria (class), Erysipelotrichia (class), Erysipelotrichia (class), Erysipelotrichia (class), Erysipelotrichia (class), Fibrobacteria (class), Flavobacteriia (class), Flavobacteriia (class), Flavobacteriia (class), Fusobacteriia (class), Fusobacteriia (class), Fusobacteriia (class), Fusobacteriia (class), Gammaproteobacteria (class), Gammaproteobacteria (class), Lentisphaeria (class), Methanobacteria (class), Methanomicrobia (class), Mollicutes (class), Negativicutes (class), Negativicutes (class), Negativicutes (class), Oligosphaeria (class), Opitutae (class), Sphingobacteriia (class), Sphingobacteriia (class), Spirochaetia (class), Synergistia (class), Synergistia (class), Verrucomicrobiae (class), Acholeplasmatales (order), Acidobacteriales (order), Acidobacteriales (order), Actinomycetales (order), Aeromonadales (order), Aeromonadales (order), Anaeroplasmatales (order), Bacillales (order), Bacteroidales (order), Bacteroidales (order), Bacteroidales (order), Bifidobacteriales (order), Bifidobacteriales (order), Burkholderiales (order), Burkholderiales (order), Burkholderiales (order), Burkholderiales (order), Burkholderiales (order), Campylobacterales (order), Campylobacterales (order), Campylobacterales (order), Cardiobacteriales (order), Caulobacterales (order), Caulobacterales (order), Caulobacterales (order), Caulobacterales (order), Clostridiales (order), Clostridiales (order), Clostridiales (order), Coriobacteriales (order), Coriobacteriales (order), Coriobacteriales (order), Coriobacteriales (order), Cytophagales (order), Deinococcales (order), Deinococcales (order), Desulfovibrionales (order), Desulfovibrionales (order), Enterobacteriales (order), Enterobacteriales (order), Enterobacteriales (order), Enterobacteriales (order), Enterobacteriales (order), Erysipelotrichales (order), Erysipelotrichales (order), Erysipelotrichales (order), Erysipelotrichales (order), Fibrobacterales (order), Flavobacteriales (order), Flavobacteriales (order), Flavobacteriales (order), Fusobacteriales (order), Fusobacteriales (order), Fusobacteriales (order), Fusobacteriales (order), Lactobacillales (order), Lactobacillales (order), Methanobacteriales (order), Mycoplasmatales (order), Neisseriales (order), Neisseriales (order), Neisseriales (order), Neisseriales (order), Oligosphaerales (order), Pasteurellales (order), Pasteurellales (order), Pasteurellales (order), Pasteurellales (order), Pasteurellales (order), Pseudomonadales (order), Pseudomonadales (order), Pseudomonadales (order), Pseudomonadales (order), Puniceicoccales (order), Rhizobiales (order), Rhizobiales (order), Rhizobiales (order), Rhizobiales (order), Rhizobiales (order), Rhodobacterales (order), Rhodobacterales (order), Rhodocyclales (order), Rhodospirillales (order), Rhodospirillales (order), Rhodospirillales (order), Selenomonadales (order), Selenomonadales (order), Selenomonadales (order), Solanales (order), Sphingobacteriales (order), Sphingobacteriales (order), Sphingomonadales (order), Sphingomonadales (order), Spirochaetales (order), Synergistales (order), Synergistales (order), Thermales (order), Thermoanaerobacterales (order), Verrucomicrobiales (order), Xanthomonadales (order), Acetobacteraceae (family), Acidaminococcaceae (family), Acidaminococcaceae (family), Acidobacteriaceae (family), Acidobacteriaceae (family), Actinomycetaceae (family), Actinomycetaceae (family), Actinomycetaceae (family), Aerococcaceae (family), Aerococcaceae (family), Aerococcaceae (family), Aeromonadaceae (family), Alcaligenaceae (family), Anaeroplasmataceae (family), Bacillaceae (family), Bacillaceae (family), Bacillaceae (family), Bacillaceae (family), Bacteroidaceae (family), Bacteroidaceae (family), Bacteroidaceae (family), Bacteroidaceae (family), Bartonellaceae (family), Bifidobacteriaceae (family), Bifidobacteriaceae (family), Bradyrhizobiaceae (family), Bradyrhizobiaceae (family), Bradyrhizobiaceae (family), Bradyrhizobiaceae (family), Brevibacteriaceae (family), Brevibacteriaceae (family), Brevibacteriaceae (family), Brucellaceae (family), Brucellaceae (family), Burkholderiaceae (family), Burkholderiaceae (family), Burkholderiaceae (family), Caldicoprobacteraceae (family), Campylobacteraceae (family), Campylobacteraceae (family), Campylobacteraceae (family), Campylobacteraceae (family), Cardiobacteriaceae (family), Carnobacteriaceae (family), Carnobacteriaceae (family), Carnobacteriaceae (family), Carnobacteriaceae (family), Carnobacteriaceae (family), Caulobacteraceae (family), Caulobacteraceae (family), Caulobacteraceae (family), Caulobacteraceae (family), Christensenellaceae (family), Clostridiaceae (family), Clostridiaceae (family), Clostridiaceae (family), Clostridiaceae (family), Clostridiales Family XI. Incertae Sedis (family), Clostridiales Family XI. Incertae Sedis (family), Clostridiales Family XI. Incertae Sedis (family), Clostridiales Family XI. Incertae Sedis (family), *Flavonifractor* plautii (species), *Bifidobacterium longum* (species), *Parabacteroides distasonis* (species), *Blautia luti* (species), *Bacteroides* vulgatus (species), *Adlercreutzia* equolifaciens (species), *Odoribacter* splanchnicus (species), *Dialister* propionicifaciens (species), *Streptococcus thermophilus* (species), *Collinsella aerofaciens* (species), *Blautia* wexlereae (species), *Blautia* obeum (species), *Bifidobacterium* (genus), *Moryella* (genus), *Intestinimonas* (genus), *Oscillospira* (genus), *Dialister* (genus), *Odoribacter* (genus), *Bilophila* (genus), *Bacteroides* (genus), *Parabacteroides* (genus), *Faecalibacterium* (genus), *Parasutterella* (genus), *Adlercreutzia* (genus), *Streptococcus* (genus), *Butyricimonas* (genus), *Hespellia* (genus), *Clostridium* (genus), *Alistipes* (genus), Bifidobacteriaceae (family), Veillonellaceae (family), Oscillospiraceae (family), Porphyromonadaceae (family), Streptococcaceae (family), Bacteroidaceae (family), Clostridiales Family XIII. Incertae Sedis (family), Desulfovibrionaceae (family), Ruminococcaceae (family), Sutterellaceae (family), Lactobacillaceae (family), Rikenellaceae (family), Bifidobacteriales (order), Desulfovibrionales (order), Bacteroidales (order), Burkholderiales (order), Clostridiales (order), Selenomonadales (order), Actinobacteria (class), Deltaproteobacteria (class), Bacteroidia (class), Clostridia (class), Betaproteobacteria (class), Negativicutes (class) Actinobacteria (phylum), Bacteroidetes (phylum), Firmicutes (phylum), and Proteobacteria (phylum).

24. The method of claim 23, wherein the microbiome composition diversity features and the microbiome functional diversity features are associated with at least one of: carbohydrate Metabolism functions, Carbohydrate Metabolism functions, Translation functions, Genetic Information Processing functions, Transport and Catabolism functions, Neurodegenerative Diseases functions, Lipid Metabolism functions, Xenobiotics Biodegradation and Metabolism functions, Nervous System functions, Endocrine System functions, Energy Metabolism functions, Amino acid metabolism functions, Amino acid related enzymes functions, Aminoacyl-tRNA biosynthesis functions, Aminobenzoate degradation functions, Amyotrophic lateral sclerosis (ALS) functions, Ascorbate and aldarate metabolism functions, Biosynthesis and biodegradation of secondary metabolites functions, Bisphenol degradation functions, Butanoate metabolism functions, Carbohydrate metabolism functions, Carbon fixation pathways in prokaryotes functions, Cellular antigens functions, Chromosome functions, Citrate cycle (TCA cycle) functions, Cysteine and methionine metabolism functions, D-Alanine metabolism functions, Electron transfer carriers functions, Energy metabolism functions, Fructose and mannose metabolism functions, Geraniol degradation functions, Glutamatergic synapse functions, Glycerophospholipid metabolism functions, Glycosaminoglycan degradation functions, Glycosphingolipid biosynthesis—ganglio series functions, Glycosphingolipid biosynthesis—globo series functions, Glyoxylate and dicarboxylate metabolism functions, Huntington's disease functions, Inositol phosphate metabolism functions, Lipoic acid metabolism functions, Lipopolysaccharide biosynthesis functions, Lipopolysaccharide biosynthesis proteins functions, Lysosome functions, Membrane and intracellular structural molecules functions, Naphthalene degradation functions, Nicotinate and nicotinamide metabolism functions, Nitrogen metabolism functions, Other glycan degradation functions, Other transporters functions, Others functions, Oxidative phosphorylation functions, PPAR signaling pathway functions, Penicillin and cephalosporin biosynthesis functions, Pentose and glucuronate interconversions functions, Peptidoglycan biosynthesis functions, Peroxisome functions, Phenylalanine metabolism functions, Phosphatidylinositol signaling system functions, Phosphonate and phosphinate metabolism functions, Photosynthesis functions, Photosynthesis proteins functions, Pores ion channels functions, Protein processing in endoplasmic reticulum functions, Proximal tubule bicarbonate reclamation functions, Pyruvate metabolism functions, RNA polymerase functions, Replication, recombination and repair proteins functions, Ribosome functions, Ribosome Biogenesis functions, Sphingolipid metabolism functions, Terpenoid backbone biosynthesis functions, Thiamine metabolism functions, Transcription machinery functions, Translation proteins functions, Type I diabetes mellitus functions, Type II diabetes mellitus functions.

25. The method of claim 1, wherein the diet-related condition comprises a dairy-allergy diet condition, and wherein the microbiome composition diversity features and the microbiome functional diversity features are associated with at least one of: *Blautia luti* (species), *Collinsella aerofaciens* (species), *Flavonifractor* plautii (species), *Roseburia inulinivorans* (species), *Parabacteroides distasonis* (species), *Faecalibacterium prausnitzii* (species), *Dorea* formicigenerans (species), *Barnesiella* intestinihominis (species), *Subdoligranulum variabile* (species), *Bacteroides fragilis* (species), *Alistipes* putredinis (species), *Bacteroides* vulgatus (species), Odoribacters planchnicus (species), *Streptococcus* thermophiles (species), *Bacteroides* thetaiotaomicron (species), *Bacteroides* caccae (species), *Erysipelatoclostridium ramosum* (species), *Dorea* (genus), *Subdoligranulum* (genus), *Marvinbryantia* (genus), *Bacteroides* (genus), *Intestinibacter* (genus), *Sarcina* (genus), *Terrisporobacter* (genus), *Collinsella* (genus), *Faecalibacterium* (genus), *Moryella* (genus), *Barnesiella* (genus), *Bifidobacterium* (genus), *Sutterella* (genus), *Eggerthella* (genus), *Intestinimonas* (genus), *Anaerosporobacter* (genus), *Hespellia* (genus), *Thalassospira* (genus), *Streptococcus* (genus), *Parabacteroides* (genus), *Roseburia* (genus), *Butyricimonas* (genus), *Akkermansia* (genus), *Anaerotruncus* (genus), *Oscillospira* (genus), *Odoribacter* (genus), Ruminococcaceae (family), Bacteroidaceae (family), Oscillospiraceae (family), Streptococcaceae (family), Coriobacteriaceae (family), Bifidobacteriaceae (family), Clostridiaceae (family), Rhodospirillaceae (family), Peptostreptococcaceae (family), Verrucomicrobiaceae (family), Sutterellaceae (family), Porphyromonadaceae (family), Prevotellaceae (family), Bacteroidales (Order), Clostridiales (Order), Flavobacteriales (order), Coriobacteriales (order), Bifidobacteriales (order), Rhodospirillales (order), Verrucomicrobiales (order), Burkholderiales (order), Bacteroidia (class), Actinobacteria (class), Clostridia (class), Flavobacteriia (class), Alphaproteobacteria (class), Verrucomicrobiae (class), Betaproteobacteria (class), Bacteroidetes (phylum), and Actinobacteria (phylum), Firmicutes (phylum) and Verrucomicrobia (phylum).

26. The method of claim 25, wherein the microbiome composition diversity features and the microbiome functional diversity features are associated with at least one of: Metabolism functions, Carbohydrate Metabolism functions, Biosynthesis of Other Secondary Metabolites functions, Transport and Catabolism functions, Translation functions, Glycan Biosynthesis and Metabolism functions, Genetic Information Processing functions, Cellular Processes and Signaling functions, Replication and Repair functions, Lipid Metabolism functions, Nucleotide Metabolism functions, Signal Transduction functions, Metabolism of Cofactors and Vitamins functions, Cell Growth and Death functions, Signaling Molecules and Interaction functions, Enzyme Families functions, Metabolism of Terpenoids and Polyketides functions, Endocrine System functions, Poorly Characterized functions, Ribosome Biogenesis functions, Sphingolipid metabolism functions, D-Alanine metabolism functions, Pentose and glucuronate interconversions functions, Other glycan degradation functions, Glycosphingolipid biosynthesis—globo series functions, Others functions, Carbohydrate metabolism functions, Galactose metabolism functions, Lysosome functions, Lipoic acid metabolism functions, RNA polymerase functions, Glycosaminoglycan degradation functions, Translation proteins functions, Bisphenol degradation functions, Amino acid related enzymes functions, Cyanoamino acid metabolism functions, Peptidoglycan biosynthesis functions, Penicillin and cephalosporin biosynthesis functions, Inorganic ion transport and metabolism functions, Fructose and mannose metabolism functions, Phenylpropanoid biosynthesis functions, Ascorbate and aldarate metabolism functions, Amino sugar and nucleotide sugar metabolism functions, Ribosome biogenesis in eukaryotes functions, Glycosphingolipid biosynthesis—ganglio series functions, DNA repair and recombination proteins functions, Inositol phosphate metabolism functions, Ribosome functions, Aminoacyl-tRNA biosynthesis functions, Phosphatidylinositol signaling system functions, Nicotinate and nicotinamide metabolism functions, Translation factors functions, "Replication functions, recombination and repair proteins" functions, Pentose phosphate pathway functions, Cysteine and methionine metabolism functions, Cell motility and secretion functions, Sulfur metabolism functions, Chromosome functions, Streptomycin biosynthesis functions, Selenocompound metabolism functions, Terpenoid backbone biosynthesis functions, Benzoate degradation functions, Other transporters functions, Biotin metabolism functions, Pyrimidine metabolism functions, Membrane and intracellular structural molecules functions, Pores ion channels functions, Starch and sucrose metabolism functions, Lipopolysaccharide biosynthesis proteins functions, Amino acid metabolism functions, Homologous recombination functions, Bacterial toxins functions, Cell cycle—*Caulobacter* functions, Signal transduction mechanisms functions, beta-Lactam resistance functions, Huntington's disease functions, Other ion-coupled transporters functions, Type II diabetes mellitus functions, Ion channels functions, Nucleotide excision repair functions, Histidine metabolism functions, Taurine and hypotaurine metabolism functions, Carbohydrate digestion and absorption functions, Peroxisome functions, Purine metabolism functions, Glyoxylate and dicarboxylate metabolism functions, Mismatch repair functions, Insulin signaling pathway functions, Biosynthesis and biodegradation of secondary metabolites functions, DNA replication proteins functions, Function unknown functions, Type I diabetes mellitus functions, Nucleotide metabolism functions, Drug metabolism—cytochrome P450 functions, Propanoate metabolism functions, Polyketide sugar unit biosynthesis functions, Phenylalanine metabolism functions, Protein export functions, Metabolism of xenobiotics by cytochrome P450 functions, Riboflavin metabolism functions, DNA replication functions, "Glycine functions, serine and threonine metabolism" functions, Two-component system functions, Butirosin and neomycin biosynthesis functions, Lipid metabolism functions, Transcription machinery functions, Glycerolipid metabolism functions, Pantothenate and CoA biosynthesis functions, Peptidases functions, Restriction enzyme functions, Plant-pathogen interaction functions, Geraniol degradation functions, Synthesis and degradation of ketone bodies functions, Fatty acid metabolism functions, Glycosyltransferases functions, Alanine functions and aspartate and glutamate metabolism functions.

27. The method of claim 1, wherein providing the health-supporting measure comprises promoting a consumable to the user based on the diet-related characterization for the user, the consumable affecting a microorganism component associated with the diet-related condition for improving health of the user with the diet-related condition.

* * * * *